United States Patent
Regimand et al.

(10) Patent No.: US 6,817,243 B2
(45) Date of Patent: Nov. 16, 2004

(54) METHODS AND APPARATUS FOR SEALING AND ANALYZING MATERIAL SAMPLES INCLUDING UNCOMPACTED BITUMINOUS SAMPLES ACCORDING TO WATER DISPLACEMENT TESTING METHODS

(75) Inventors: Ali Regimand, Raleigh, NC (US); Lawrence H. James, Raleigh, NC (US)

(73) Assignee: InstroTek, Inc., Raleigh, NC (US)

( * ) Notice: Subject to any disclaimer, the term of this patent is extended or adjusted under 35 U.S.C. 154(b) by 0 days.

(21) Appl. No.: 10/462,900

(22) Filed: Jun. 17, 2003

(65) Prior Publication Data

US 2003/0209071 A1 Nov. 13, 2003

Related U.S. Application Data

(60) Division of application No. 09/580,792, filed on May 30, 2000, now Pat. No. 6,668,647, which is a continuation-in-part of application No. 09/340,105, filed on Jun. 25, 1999, now Pat. No. 6,321,589.

(51) Int. Cl.$^7$ ................................................. G01N 9/10
(52) U.S. Cl. ......................................................... 73/437
(58) Field of Search ................................ 73/32 R, 433, 73/437

(56) References Cited

U.S. PATENT DOCUMENTS

| | | | |
|---|---|---|---|
| 4,083,228 A | 4/1978 | Turner et al. | 73/32 R |
| 5,760,293 A | 6/1998 | Orr et al. | 73/32 R |

FOREIGN PATENT DOCUMENTS

| | | |
|---|---|---|
| DE | 2004530 A | 8/1971 |
| EP | 0936451 A1 | 8/1999 |
| JP | 62269040 A | 5/1988 |
| JP | 10010032 A | 1/1998 |

OTHER PUBLICATIONS

Birello et al., "Advance in density measurements by means of an automatic hydrostatic weighing system of 100 g capacity," Measurement, vol. 7, pp. 157–162 (Oct.–Dec. 1989).
Dept. of Defense, "Standard Test Method for Bulk Specific Gravity and Density of Compacted Bituminous Mixtures Using Paraffin–Coated Specimens," ASTM Standards, Designation: D1188, pp. 118–120 (Oct. 1996).
Dept. of Defense, "Standard Test Method for Theoretical Maximum Specific Gravity and Density of Bituminous Paving Mixtures," ASTM Standards, Designation: D2041, pp. 176–182 (Dec. 1995).
Dept. of Defense, "Standard Test Method for Bulk Specific Gravity and Density of Non–Absorptive Compacted Bituminous Mixtures," ASTM Standards, Designation: D2726, pp. 242–244 (Oct. 1996).
Stephens, "Bituminous Mix Density by Coated Specimen," Project No. 67–5, Connecticut Dept. of Transportation (Jan. 1973).
Wolf, B., "Application of hydrostatic weighing to density determination of tiny porous samples," Rev.Sci. Instrum, vol. 66 (3), pp. 2578–2581 (Mar. 1995).
PCT International Search Report, International Application No. PCT/US00/17150 mailed Oct. 20, 2000.

Primary Examiner—John E. Chapman
(74) Attorney, Agent, or Firm—Myers Bigel Sibley & Sajovec PA

(57) ABSTRACT

Methods of determining an apparent density of a sealant used to encase a material specimen during liquid displacement evaluations include: (a) providing a plurality of material reference samples in an assortment of dimensional ranges and geometrical shapes; (b) obtaining a sealant used to encase material specimens undergoing liquid displacement evaluations; and (c) establishing a plurality of apparent density values for the sealant, one apparent density value for each of the plurality of reference samples identified in the providing step.

9 Claims, 30 Drawing Sheets

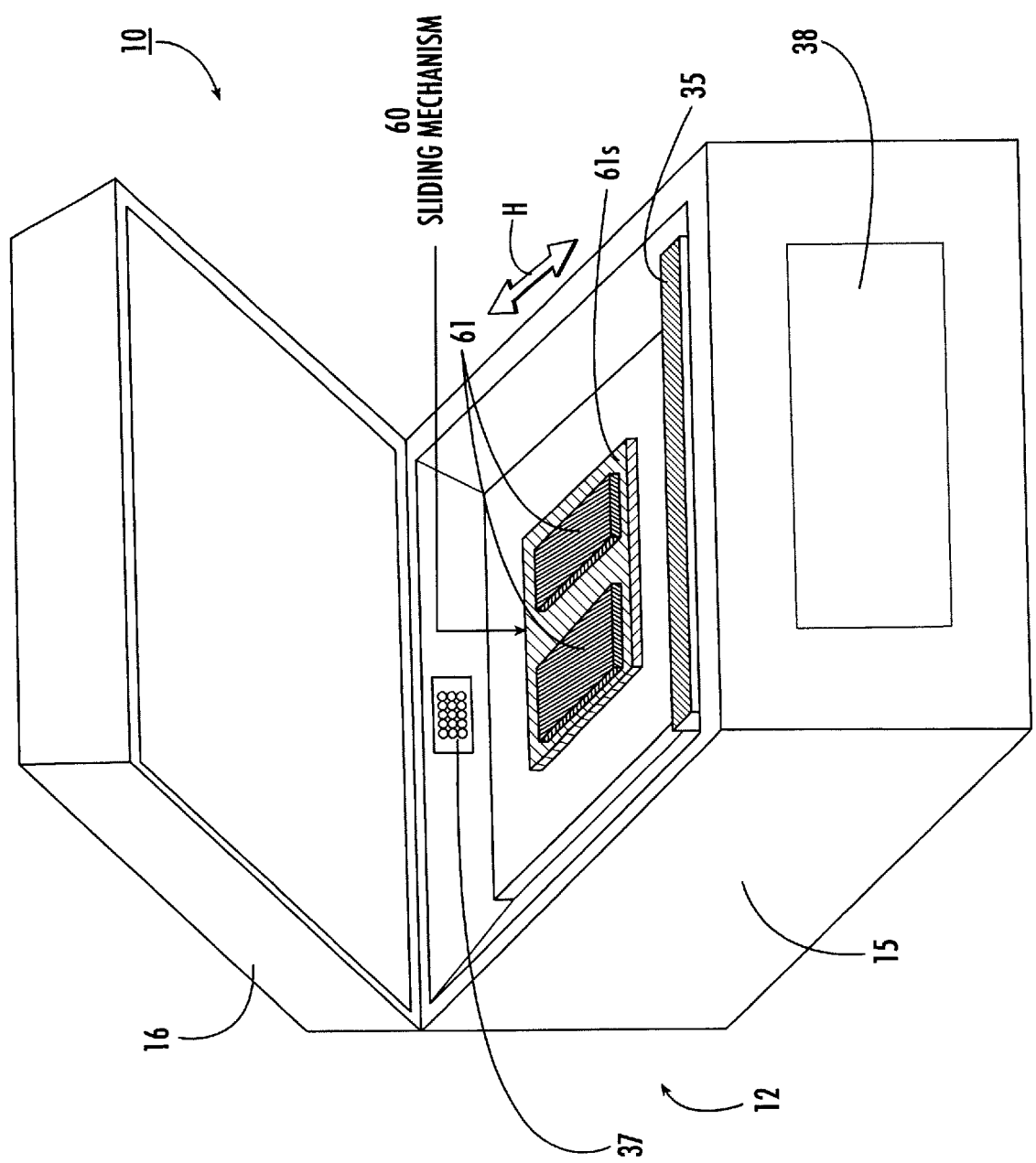

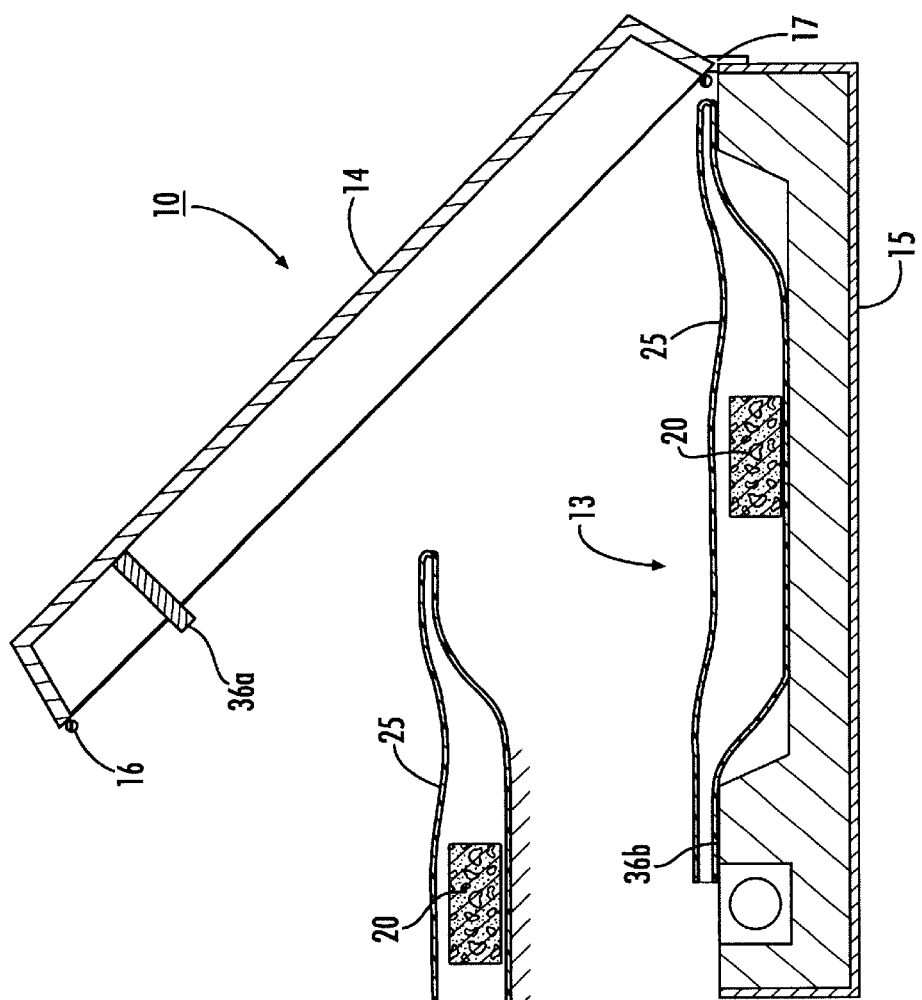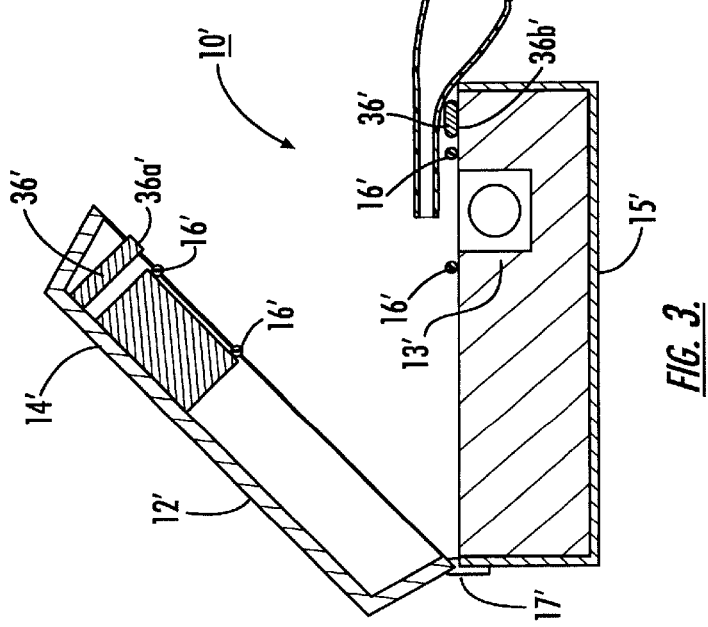

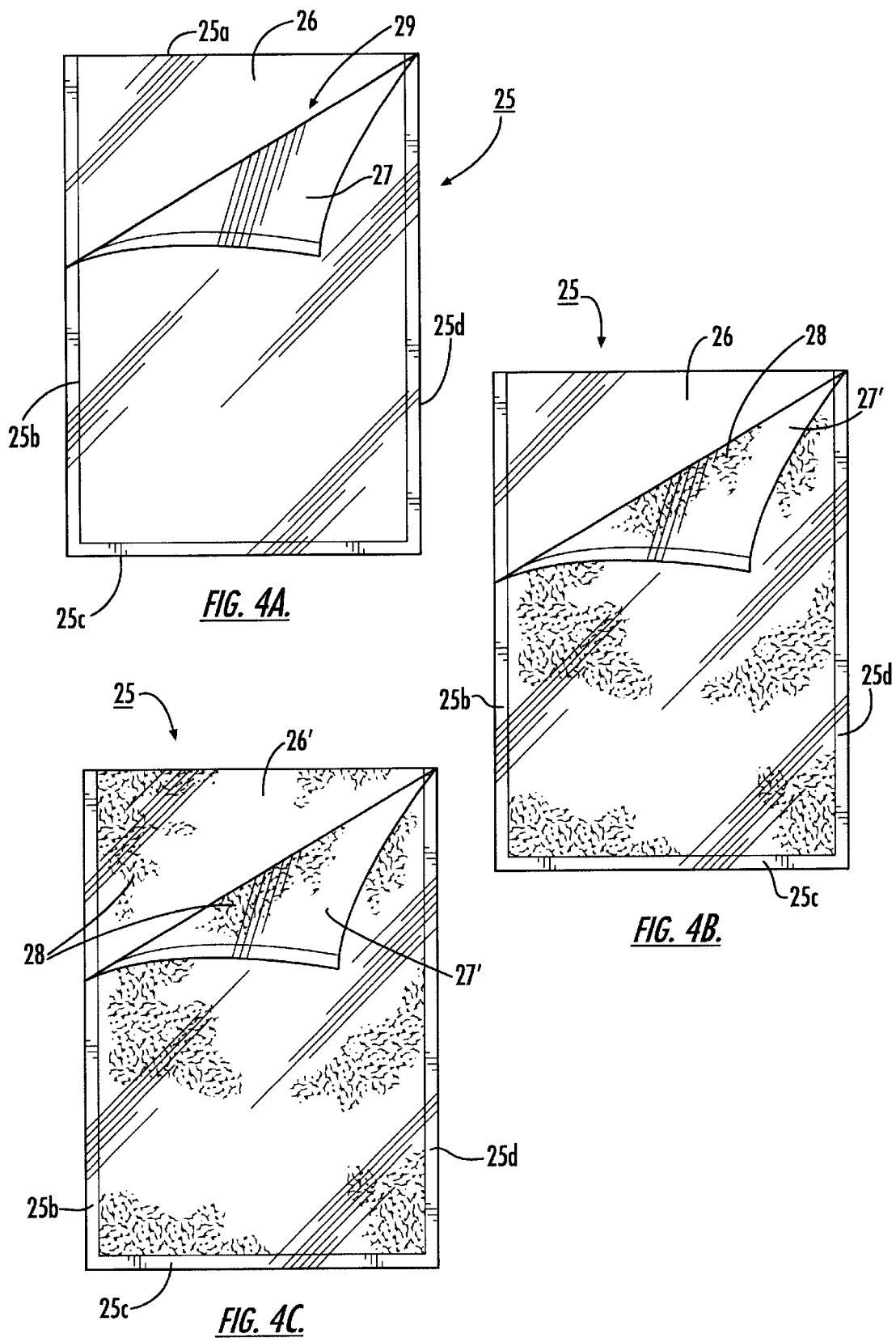

FIG. 21.

CALIBRATION OF BAG DENSITY

| SAMPLE # | STD WT IN AIR | STD WT IN H2O | SEALED IN AIR | SEALED IN H2O | WT OF BAG | VOL OF STD | VOL OF STD+BAG | VOL OF BAG | DENSITY OF BAG |
|---|---|---|---|---|---|---|---|---|---|
| STD1 | 2498.6 | 1576 | 2532.3 | 1565.5 | 33.7 | 925.38 | 969.71 | 44.33 | 0.760 |
| STD2 | 3751.5 | 2365.7 | 3785.2 | 2354 | 33.7 | 1389.97 | 1435.51 | 45.54 | 0.740 |

CALCULATION OF CORE DENSITY

| SAMPLE # | CORE WT IN AIR | SEALED WT IN AIR | SEALED WT IN H2O | TOTAL VOL | VOL OF BAG | VOL OF CORE | DENSITY OF CORE (gm/cm³) | DENSITY OF CORE (pcf) |
|---|---|---|---|---|---|---|---|---|
| SMA-1 | 4501.4 | 4534.6 | 2480.1 | 2060.68 | 44.27 | 2016.42 | 2.232 | 139.4 |
| SMA-2 | 4603.4 | 4636.9 | 2569.5 | 2073.62 | 44.67 | 2028.95 | 2.269 | 141.6 |
| SMA-3 | 4726.9 | 4760.5 | 2612 | 2154.96 | 44.80 | 2110.16 | 2.240 | 139.8 |
| FG-SP-1 | 4680.3 | 4715.2 | 2677.1 | 2044.23 | 46.53 | 1997.70 | 2.343 | 146.3 |
| FG-SP-2 | 4709.2 | 4743.6 | 2680 | 2069.81 | 45.87 | 2023.94 | 2.327 | 145.3 |
| FG-SP-3 | 4728.3 | 4763.7 | 2721.9 | 2047.94 | 47.20 | 2000.74 | 2.363 | 147.5 |
| CG-SP-2 | 4759.2 | 4793.3 | 2679 | 2120.66 | 45.47 | 2075.20 | 2.293 | 143.2 |
| CG-SP-3 | 4771.4 | 4805.7 | 2685.2 | 2126.88 | 45.73 | 2081.15 | 2.293 | 143.1 |
| CG-SP-1 | 4771.1 | 4805.8 | 2683.7 | 2128.49 | 46.27 | 2082.22 | 2.291 | 143.0 |
| CG-SP-1 | 4771.1 | 4805.6 | 2685.8 | 2126.18 | 46.00 | 2080.18 | 2.294 | 143.2 |
| CG-SP-1 | 4771.1 | 4804.6 | 2685.7 | 2125.28 | 44.67 | 2080.61 | 2.293 | 143.2 |
| | | | | | | STD. DEV | 0.001 | 0.074 |
| OGFC-1 | 3531.3 | 3564 | 1849 | 1720.16 | 43.60 | 1676.56 | 2.106 | 131.5 |
| OGFC-2 | 3806.5 | 3839.7 | 2015.2 | 1829.99 | 44.27 | 1785.72 | 2.132 | 133.1 |
| OGFC-3 | 3770.6 | 3805.1 | 1976.5 | 1834.10 | 46.00 | 1788.10 | 2.109 | 131.6 |

DETERMINE Corelok™ SEALANT MATERIAL DENSITY USING ALUMINUM STANDARDS ("As")

| SAMPLE # | A<br>As WEIGHT<br>IN AIR | B<br>As WEIGHT<br>IN WATER | C<br>SEALED As<br>WEIGHT IN<br>AIR | D<br>SEALED As<br>WEIGHT IN<br>WATER | E<br>C-A | F<br>B-A<br>0.997 | G<br>C-D<br>0.997 | H<br>G-F | I<br>E/H |
|---|---|---|---|---|---|---|---|---|---|
| | | | | | | | | | |
| | | | | | | | | | |
| | | | | | | | | | |
| | | | | | | | | | |

DETERMINE CORE DENSITY USING Corelok™ SEALANT TECHNIQUE

| SAMPLE # | J<br>CORE WEIGHT<br>IN AIR | K<br>Corelok™<br>CORE WEIGHT<br>IN AIR | L<br>Corelok™<br>CORE WEIGHT<br>IN WATER | M<br>K-J<br>0.997 | N<br>K-L<br>0.997 | O<br>M-N | P<br>(CORE<br>DENSITY)<br>J/O |
|---|---|---|---|---|---|---|---|
| | | | | | | | |
| | | | | | | | |
| | | | | | | | |
| | | | | | | | |

*FIG. 22.*

SAMPLE SPREAD IN BAG

SEALED SAMPLE IN HOLDER UNDER WATER

FIG. 24.

| SAMPLE# | A<br>CORE WEIGHT IN AIR (gm) | B<br>CORELOK SEALED CORE WEIGHT IN AIR (gm) | C<br>CORELOK SEALED CORE WEIGHT IN WATER (gm) | D<br>$\frac{B-C}{0.997}$ | E<br>B-A<br>BAG DENSITY | F<br>D-E | G<br>CORE DENSITY (gm/cm³)<br>A/F |
|---|---|---|---|---|---|---|---|
| SAMPLE A | 1662.8 | 1689.2 | 982.1 | 709.23 | 33.98 | 675.25 | 2.462 |
| | | | | | | | |
| | | | | | | | |
| | | | | | | | |
| | | | | | | | |
| | | | | | | | |
| | | | | | | | |
| | | | | | | | |
| | | | | | | | |
| | | | | | | | |
| | | | | | | | |
| | | | | | | | |
| | | | | | | | |
| | | | | | | | |

APPARENT BAG DENSITIES:
SMALL BAG: 0.777
LARGE BAG: 0.720

NOTE: APPARENT BAG DENSITIES ARE MEASURED AT THE FACTORY AND PROVIDED WITH EACH BAG SHIPMENT. USE THESE VALUES FOR THE CALCULATION IN COLUMN E.

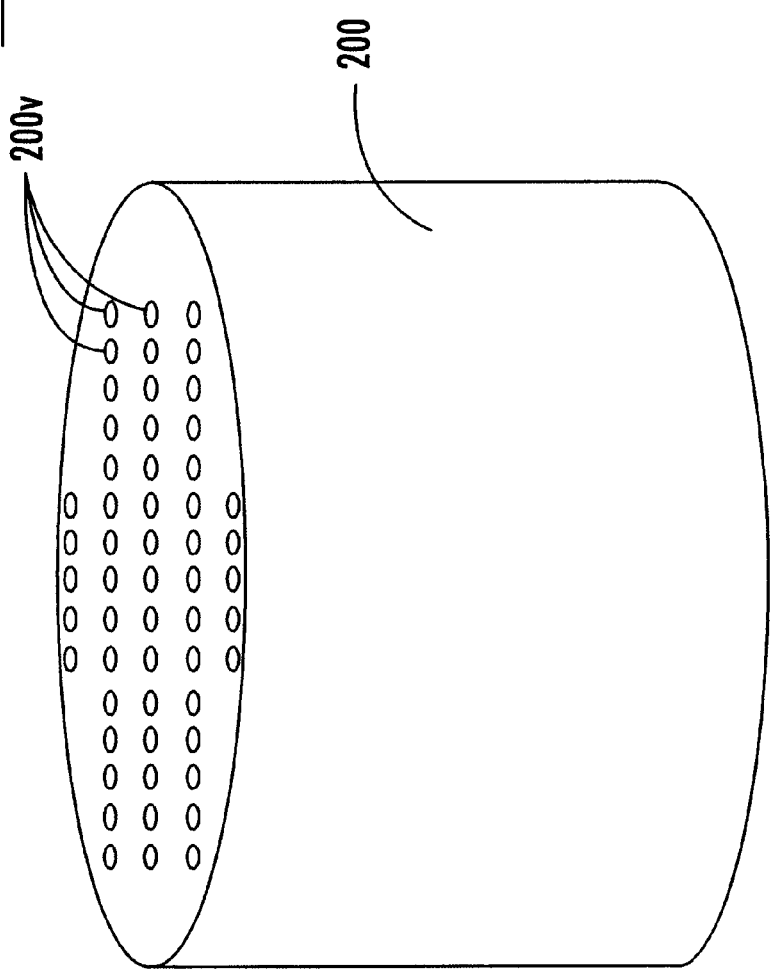

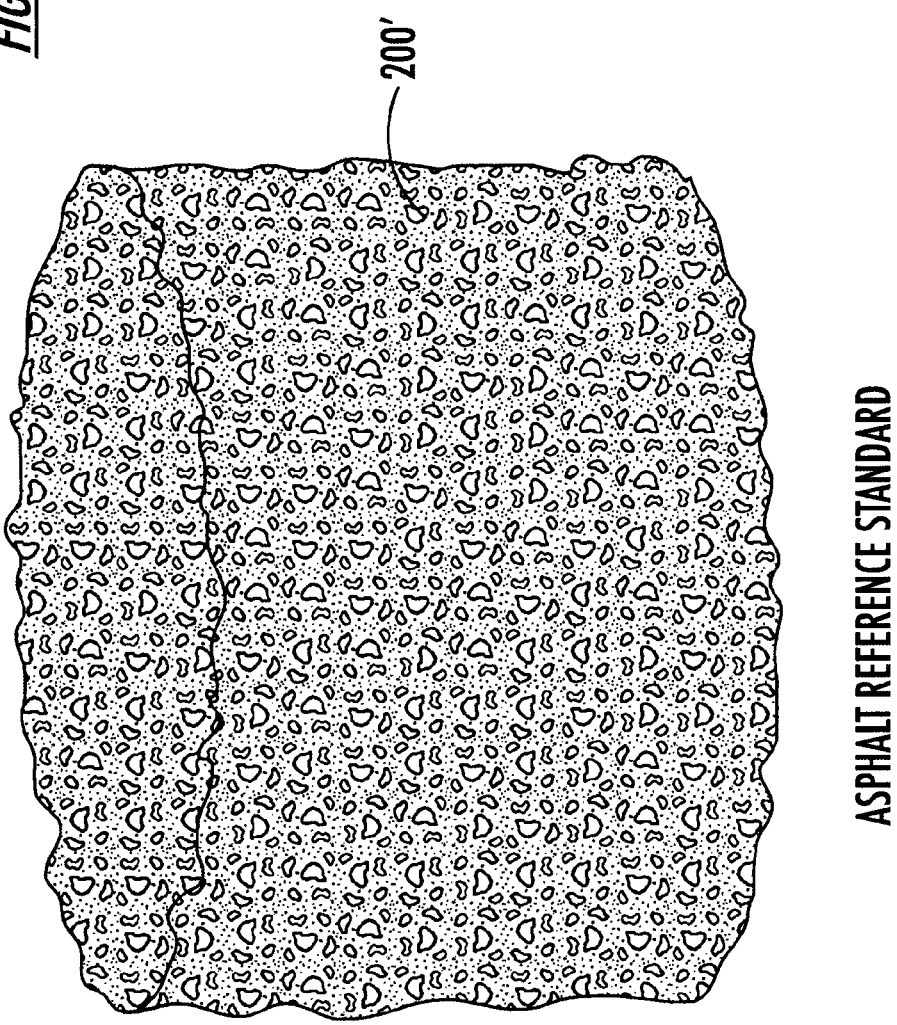

REFERENCE STANDARDS FOR TESTS INVOLVING
CUTTING OF THE SEALANT UNDER WATER

METHODS AND APPARATUS FOR SEALING AND ANALYZING MATERIAL SAMPLES INCLUDING UNCOMPACTED BITUMINOUS SAMPLES ACCORDING TO WATER DISPLACEMENT TESTING METHODS

RELATED APPLICATIONS

This application is a second divisional of U.S. patent application Ser. No. 09/580,792, filed May 30, 2000, now U.S. Pat. No. 6,668,647, which is a continuation-in-part of U.S. patent application Ser. No. 09/340,105, filed on Jun. 25, 1999, now U.S. Pat. No. 6,321,589, the contents of which are hereby incorporated by reference as if recited in full herein. U.S. patent application Ser. No. 10/196,650, filed Jul. 16, 2002, now U.S. Pat. No. 6,629,459, is the first divisional application of U.S. Pat. No. 6,668,647.

FIELD OF THE INVENTION

The present invention is related to methods and devices used to determine the specific gravity or density of material specimens by water displacement methods. This invention is particularly suitable for use with material specimens which exhibit irregular or coarse exterior surfaces and porosity or voids, such as samples of uncompacted, loose, or compacted bituminous mixtures, soil samples, aggregates, and concrete specimens used in the structure, infrastructure, and/or underlayment of many roadways.

BACKGROUND OF THE INVENTION

In the construction industry, a water displacement test is used to establish the material density associated with the acceptability of the material durability used to form the pavement or underlayment of roadways or other construction or building projects. For example, most roadways consist of a plurality of materials and layers including different types of aggregates, rocks, stones, gravel, or other materials which are compacted together to form the foundation and/or structure for the roadway surface and construction structures. These material compositions can be described as "compacted mixtures". The composition of the compacted mixture is generally considered to be an important factor in the service life of the construction project. In order to assure that the construction projects (such as a particular roadway or substructure) exhibit sufficient performance characteristics and useful service lives, most construction projects are constructed to certain minimum build specifications or standards. One important standard used to assess the acceptability of the compacted mixture, particularly in the asphalt and soil industries, is a bulk specific gravity and density measurement of the compacted mixture.

A typical standard test method used to assess the bulk density of the compacted bituminous (asphalt) mixture is ASTM D2726. During evaluation, a field sample or laboratory molded sample is obtained. The pavement specimens are usually taken from pavements in the field with a core drill, diamond or a carborundum saw, and the like. In any event, the core specimen, whether from the field or molded in the laboratory, is typically in the shape of a cylinder. As such, the field specimen typically exhibits a rough uneven exterior surface. In order to preserve the integrity of the core specimen during and after removal from pavements or molds (and during testing), care is taken to avoid distortion, bending, or cracking of the specimens.

Generally described, the ASTM D2726 test method involves measuring the specimen's weight, both in air and in water. More particularly, during this analysis, three different weights of the specimen are measured; a weight in water, a dry weight, and a saturated surface dry weight. The difference between the sample's weight in the air and in the water is equal to the weight of the water displaced (which can be measured, this determines the volume of the water displaced) and saturated surface dry weight can be used to ascertain the amount of water absorbed by the sample. Since the volume of displaced water is known, the specific gravity of the sample can be determined. The test method results can be used to determine the unit weight of compacted construction material (typically dense) mixtures. This method is generally accepted as being accurate for smooth and/or non-porous samples. Indeed, the method is used around the world to determine the conformance to various regulatory specifications, both for prepared laboratory samples and field extracted samples.

The ASTM D2726 test method is not recommended for use with samples that contain open or interconnecting voids or that absorb more than 2% of water by volume, or both, as determined by saturated surface dry weight, e.g., "porous samples". Using this test method for porous samples can provide unreliable density measurements. This is attributed to the variable amount of water absorbed by the porous sample which can result in an inaccurate volume determination and, thus, an inaccurate and unreliable density determination.

Presently, specification standards require that the porous samples be measured differently from the ASTM D2726 test method. Typically, ASTM D1188 is recommended for use if the percent water absorbed by the specimen or sample exceeds 2%. ASTM D1188 is directed to the use of "paraffin-coated specimens" to seal the sample to prevent water infiltration into the porous samples whose specific gravity is to be determined by water displacement methods. In one paraffin application, in order to coat the sample, the sample is submerged into hot-melted paraffin wax and pulled out and cooled allowing the paraffin to solidify and form a shell around the sample. The density is then determined using the water displacement method. Unfortunately, the thickness of the paraffin layer can be inconsistent, which can produce variability in the measurement results. Further, penetration of the wax into the voids themselves can result in inflated density measurements. In addition, paraffin wax is difficult, if not impossible, to completely remove once applied, and the specimen is generally rendered unsuitable for further analysis. Further, the presence of a supply of melted hot wax can introduce safety hazards for laboratory personnel.

ASTM D1188 describes using Parafilm®, an elastomeric self-sealing moisture proof film obtainable from most scientific suppliers. As described, three pieces of Parafilm® are cut from the roll, two 100×100 mm (4×4 in) and one 100×200 mm (4×8 in). The backing is pulled off the backside of one of the 100×100 pieces and opposite sides of the film are grasped to stretch the film (carefully, without creating holes) and then placing the stretched film over one end of the specimen and pressing the sides of the stretched film around the sample. The specimen is turned over and positioned on a cushioned foam mat and the other end is wrapped with another piece of the stretched Parafilm®. Another specimen is used to force the air pockets from both surfaces by pressing against a piece of foam which is positioned on top of the wrapped specimen. A sharp knife is used to trim the excess film, keeping a minimum of 15 mm (0.5 in) on the side of the specimen at each end. The third piece of film is then applied. This elastomeric film method determines the "apparent specific gravity of Parafilm®" by using the specific gravity of an aluminum calibration cylinder before and after it is wrapped with Parafilm® as noted above. Unfortunately, this sealing method is relatively labor intensive. Further, the amount of Parafilm® used during the wrap as well as how it is stretched over the sample can be inconsistent, which can result in measurement inconsistencies. In addition, air can be trapped under the film during the film wrapping process. Still further, the film is susceptible to puncture both during application and during actual testing potentially allowing water to enter through the puncture. Clearly, either the trapped air or puncture can adversely affect the reliability of this method.

Another method for measuring the bituminous mix density by water displacement with coated specimens is proposed by Jack E. Stephens, in a report entitled "Bituminous Mix Density by Coated Specimen," Project Number 67-5, Connecticut Department of Transportation (January 1973). This method proposes using a vacuum pump and two sheets of acetate to wrap the specimen. The first acetate or plastic sheet is apparently heated and held in tension in position while the sample is raised until it contacts the plastic. The rising specimen enters the center of the tensioned sheet and forces the plastic to wrap around the upper surface and the sides of the specimen. The tensioned material provides a surplus of material extending from both sides when the first sheet is released from the tensioning members (plastic clamps). This surplus material is then trimmed, leaving the lower surface and a minor portion of the sides exposed. The sample is then turned such that the lower surface faces upward and a second sheet of acetate is wrapped over the remaining exposed surface, and the second sheet overlaps a portion of the first sheet along the sides. Again, the excess material of the second acetate sheet is trimmed. After trimming, the sample is enclosed in a shrink-wrap acetate material layer with a double layer of the acetate formed along its sides. This method also proposes using a heater when forming the plastic over the specimen, to soften the plastic to facilitate the molding of the (heated) soft plastic to the sample. Unfortunately the heating temperature and time of the plastic can affect the degree of the softness of the plastic, which, in turn, affects the adherence of the plastic to coarse, irregular, and porous samples, thereby undesirably introducing variations into the measurement. Again, this procedure can be relatively cumbersome and the amount of trim removed can vary from sample to sample, introducing possible measurement error. Further, without careful control of the amount of vacuum pulled on the sample, significant variability can occur in the density measurement. Also, the speed at which the sample is raised to contact the plastic can cause the specimen or sample to puncture the sealing material allowing water to leak into the sample during liquid displacement testing. In addition, asphalt softens at approximately 150° F. Heating the plastic can soften the asphalt layer at the surface and thereby change or alter the composition or condition of the sample during the water displacement test and also for any subsequent tests conducted subsequent to the liquid displacement density determination.

In recent years, the Federal Highway Administration ("FHA") has worked to improve the service life of bituminous pavements. As a result of a recent 5-year test, the FHA has recommended using compacted bituminous mixtures with larger aggregate size proportions. This larger aggregate size is believed to improve pavement performance and service life. Unfortunately, due to the use of larger aggregates, the asphalt specimens now prepared in the lab or extracted from the field have coarse and porous compositions. Typically, the coarse and porous compositions include a larger than 2% variation in air weight compared to saturated surface dry weight. However, the true absorption rate into the material is not possible with porous samples. The rapid water infiltration into the sample when placed in the tank and water drainage out of the sample after removal from the tank can mask the "true" absorption rate and, adversely influence the density measurement results. This variation will make these samples unsuitable for the unsealed evaluation, potentially requiring that such samples be evaluated by sealed water displacement methods.

An additional test, known by those in the art as the "Rice Test" or the "Rice Gravity Test", has conventionally been used to determine the maximum theoretical specific gravity of a loose (uncompacted) sample of asphalt or bituminous paving mixtures. This value is used to establish the intrinsic properties of the composition of the paving mixture which varies sample to sample depending, inter alia, on the types and amounts of aggregates and/or bituminous materials used therein. This pre-compacted theoretical specific gravity value can be used to evaluate the suitability of the mixture, and can also be used to analyze the subsequent compacted bituminous material to determine if the proper mix design compaction level is obtained.

Generally described, in the Rice Test method, one first positions the loose uncompacted bituminous sample in a flask. The flask is then filled with water to a predetermined level sufficient to cover the sample. A vacuum is then applied to the flask to attempt to remove all the air from the pores of the aggregate and/or other materials in the sample. Typically, after about 15 minutes, the flask is submerged and evaluated by the amount of water displaced inside a water tank. The water displacement test uses the known air weight and the evacuated weight of the sample undergoing analysis to calculate the sample maximum specific gravity. See e.g., ASTM D2041. This procedure generally takes about 20–30 minutes.

Unfortunately, the Rice method can cause performance problems with the associated vacuum systems. The performance of the vacuum systems degrade because, during the evacuation procedure, water from the flask can enter the pump and reduce its operating life. In addition, with more absorptive aggregates, water can be drawn into the pores of the components of the uncompacted mixture more readily during the initial 15 minutes of vacuum operation masking the true measurement. Unfortunately, a relatively lengthy correction test for water absorption must then be performed to compensate for the measurement errors attributed thereto. This correction test method can take 2–3 hours. In addition, in operation, the vacuum level introduced onto the sample undergoing analysis is very important to the test measurements. However, due to the performance degradation of the pump, the vacuum level introduced onto the sample can change with time, potentially causing repeatability problems with the tests.

OBJECTS AND SUMMARY OF THE INVENTION

It is therefore an object of the present invention to provide a reliable and easy to use method for determining the specific gravity and/or density of uncompacted and/or compacted material samples with water displacement evaluation techniques.

It is another object of the present invention to provide an improved method and device for sealing material specimens, including those exhibiting coarse surfaces and porous properties, to inhibit water infiltration into the sample when measuring specific gravity of that sample by water displacement methods.

It is an additional object of the present invention to provide a consistent and repeatable sealing method which minimizes laboratory labor efforts and can be easily used.

It is yet another object of the present invention to seal porous samples for water displacement evaluation in a manner which is relatively quick, provides accurate testing measurements, and which preserves the integrity of the sample such that it is suitable for further post-sealing test evaluation.

It is another object of the present invention to provide a reliable and easily used method for determining the maximum specific gravity and/or density of uncompacted or loose bituminous material samples with water displacement evaluation techniques.

It is an additional object of the present invention to provide a water displacement maximum specific gravity and/or permeability test method which reduces the likelihood that water will be drawn into the vacuum pump during testing procedures.

It is another object of the present invention to provide an easy method of transferring a sample undergoing evaluation from a vacuum apparatus to a testing apparatus while the sample is maintained within a sealant material in an evacuated state.

It is yet another object of the present invention to provide an evaluation method for assessing the permeability or porosity of asphalt.

It is an additional object of the present invention to provide a vacuum apparatus configured to reduce the likelihood that the bag will puncture during the sealing process.

It is another object of the present invention to provide improved methods of establishing apparent bag density values suitable for use in measurements employing water displacement tests.

It is yet another object of the present invention to provide improved reference samples and/or reference standard configurations for use in density measurements.

It is an additional object of the present invention to provide vacuum sealing systems and methods which handle samples for maximum density testing that can reduce errors which can be introduced by operational variation in vacuum pumps and/or vibration equipment used for conventional Rice Test evaluations.

These and other objects of the present invention are provided by methods, encased samples, and systems which employ at least one preformed precision-manufactured sealable bag which is sized and configured to hold a compacted material sample therein. The preformed resilient bags are manufactured to be consistent in size (or sizes), and, thus, are configured to reliably displace a constant volume of water, without relying on an operator's shaping of the material onto the sample. The method and encased samples provide predictability in the sealing application and thus, more reliable water displacement measurement evaluations. During operation, the material specimen sample is conveniently inserted into the bag at the use point and the bag is then conformed to rest against the surface of the sample in a controlled manner, i.e., such as by manipulating the bag to a surface conformal configuration (the walls of the bag substantially conform to the sample's external perimeter surface profile) and sealed. Preferably, a vacuum apparatus with a preset time and/or pressure is used to collapse or deflate a chamber holding the bag (remove the excess air) and then the chamber is also preferably controllably exhausted (returned to atmospheric pressure) in a manner which gradually introduces the air therein to collapse the bag against the sample and, thus, provides an automatic and consistent sealed sample configuration corresponding to the sample type. The controlled exhaust rate can inhibit punctures as the bag walls conform to the side of the specimen gradually (as opposed to abruptly). Advantageously, no trimming of excess material is required and the variability due to operator input is minimized. Also, after the water displacement test, the sample's composition and structural integrity remains intact and the sample is thus available for further evaluation.

More particularly, a first aspect of the present invention is a sample specimen configuration for a dense material sample to inhibit liquid contacting the sample during liquid displacement tests. The sample specimen configuration comprises at least one preformed resilient bag having at least one sealed side and one opening formed therein and defining a holding chamber. The system also includes a material sample having an exterior surface contour positioned in the chamber of the preformed resilient bag. The preformed bag has a first non-sealed configuration and a second sealed configuration. In the second sealed configuration, the preformed bag is configured to substantially conform to the sample's exterior surface contour. In a preferred embodiment, the configuration is provided by a system which includes a vacuum apparatus used to encase and conform the bag to the surface of the sample and a heater element used to seal the open edge of the bag while the bag is under vacuum.

Another aspect, of the present invention is a method for preparing a compacted sample for liquid displacement testing. The method comprises the steps of providing a preformed resilient bag with predetermined dimensions, the bag having a perimeter with a portion of the perimeter having an open portion formed therein. A material specimen is subsequently inserted into the bag and the bag open portion is sealed. The method also includes the step of encasing the material specimen within the bag such that a portion of the bag substantially conforms the exterior profile of the material specimen held therein to thereby form an encased specimen suitable for liquid displacement evaluation.

An additional aspect of the present invention is an apparatus for sealing a specimen. The apparatus comprises a preformed resilient bag defining a holding chamber therein and a compacted material sample having an exterior surface contour positioned in the chamber of the resilient bag. The bag has a first non-sealed configuration and a second sealed configuration. In the second configuration, the bag is configured to encase and substantially conform about the sample's exterior surface contour. The apparatus also includes a vacuum apparatus which is operably associated with the preformed bag holding the compacted material sample. In a preferred embodiment, the apparatus includes an air chamber with an air flow channel with an adjustable flow rate. In operation, and the bag collapses to conform to the exterior contour responsive to the controlled introduction of air into the air chamber after evacuation of same.

An additional aspect of the present invention is a reproducible puncture resistant water jacket for a compacted material specimen for use in water displacement density or specific gravity tests. The water jacket includes a preformed resilient bag structure having at least two co-joined sides. The structure is sized and configured to receive a compacted material specimen therein. As such, the bag structure has a first open configuration and a second sealed configuration. The bag structure core is conformal to the profile of the specimen in the second sealed configuration (i.e., a portion of the bag conforms to rest against the exterior of the specimen while the portions of the bag structure away from the specimen contacts the opposing wall surface). The bag structure is produced at a first site and completely sealed at a second site remote from the first site. Preferably, the bag structure is defined by a preformed bag with a single open side. It is also preferred that the bag structure be configured for puncture resistance such as with reinforcement regions, patches, or double bags.

Yet another aspect of the present invention is directed to a method for immersing a compacted mixture in a liquid displacement bath for determining the specific gravity of specimens. The method comprises the steps of inserting a material specimen having an exterior surface into a bag having at least one open side and encasing the specimen by collapsing a portion of the bag to substantially conform to the material specimen exterior surface. The method also includes sealing the bag to enclose the material specimen therein and placing the sealed collapsed bag with specimen in a liquid displacement bath. The volume of displaced water associated with the placing step is then measured. Preferably, the method also includes the step of establishing bag density values associated with a particular bag type and specimen type across a plurality of specimen thicknesses. This establishing step can be performed by using a plurality of reference standards with known densities (aluminum blocks) and different thicknesses to determine a mathematical model or relationship which can be programmed into a computer. This established relationship can be provided at the factory and not require an operator to determine the value at the point of test for each specimen in the laboratory.

An additional aspect of the present invention is a resilient container for a porous sample. The resilient container comprises a first layer of a first material. The first layer includes a first perimeter portion. The resilient container also includes a second layer of a second material configured to overlay the first layer. The second layer includes a second perimeter portion corresponding to the first perimeter portion. The first and second perimeter portions are co-joined along a major portion thereof defining an internal compressible chamber therebetween and edge portions which extend laterally outward from the chamber. A compacted material specimen is held in the chamber. The first and second layers are formed of a resilient material such that the chamber has a first collapsed position and a second non-collapsed position, the collapsed position corresponds to the chamber being sealed with the compacted material specimen positioned therein. Preferably, the first and second layer materials are selected to provide oxygen resistant shielding and/or puncture resistance.

Another aspect of the present invention is a method of preparing a porous sample for use in a water displacement testing. The method comprises the steps of inserting a porous sample having an exterior profile into a preformed bag and collapsing the preformed bag to contact the exterior profile of the porous sample. The preformed bag is sealed to enclose the porous sample therein, thereby providing a sealed sample.

Yet an additional aspect of the present invention is directed to a method and computer program product for sealing a material specimen in a preformed bag. The computer program product comprises a computer readable storage medium having computer readable program code means embodied in the medium, the computer-readable program code means comprises computer readable program code means for accepting user input information associated with identifying the material specimen and computer readable program code means for comparing the identified material specimen with predetermined operating parameters for directing the operation of a vacuum apparatus operably associated with the preformed bag holding the material specimen. The product also includes a computer readable program code means for directing the operation of the vacuum apparatus corresponding to the operating parameters associated with the identified material specimen to compress the preformed bag to substantially conform to the exterior shape of the material specimen. Preferably, the computer program product also includes a computer readable program code means for accepting user input information associated with the identification of the preformed bag being sealed (i.e., product identification number which relates to bag design parameters such as size, material type, etc.). In a preferred embodiment, the computer program product further includes a computer readable program code means for providing a preformed bag adjustment number for use in specific gravity or density measurement calculations associated with water displacement tests and a computer readable program code means for printing information to a printer.

It is an additional aspect of the present invention to provide a semi automated system for establishing specific gravity in compacted specimens using liquid displacement testing. The system includes a vacuum apparatus with an internal vacuum chamber and a first scale positioned integral to the vacuum apparatus such that it can provide a dry weight measure of a sealed specimen held therein. The system also includes a liquid displacement bath and a second scale operably associated with the liquid displacement bath. The system further includes a computer means operably associated with the first scale, the second scale, and the vacuum apparatus. The computer means includes a computer program product which has a computer readable program code means for calculating the specific gravity of a compacted material specimen corresponding to data directly input into the computer means from the first and second scales.

An additional aspect of the invention is directed to an alternative Rice Test evaluation. These methods analyze the density of a paving mixture or an uncompacted or loose material sample. The methods include the steps of measuring the weight of an uncompacted material sample in air and encasing the uncompacted material sample in a vacuum-sealed bag such that the bag substantially conforms to the material sample held therein. The weight of the sealed bag with the material sample held therein is weighed in air. The sealed bag with the material sample is then immersed in a liquid displacement bath. An opening is introduced or inserted into the sealed bag with the material sample as the material sample in the bag is immersed in the liquid displacement bath. The weight of the opened bag in liquid is measured subsequent to the forming step while the sample (in the bag) is immersed in the liquid displacement bath. The weight is obtained after water substantially fills the voids of the sample within the bag. The density of the uncompacted material sample is determined based on the weights obtained during the measuring steps.

In a preferred embodiment, the sealed bag with the sample therein is submerged completely in the liquid displacement bath and the scales are allowed to stabilize before the immersed bag is cut open. If holes have been introduced prior to this step (sometimes occurring because the specimens are coarse and can puncture the bag during handling), the scales will not stabilize during the first 120–240 seconds as water is seeping into the bag. If the scales stabilize during the first two minutes or so, this affirms that the integrity of the bag is maintained and the procedure can continue. If, on the other hand, the water immersion scales fail to stabilize, a leak in the bag is indicated. The non-stabilized scales can alert the operator to abort the test and reinitiate the test with a new sealed bag (with the specimen dried), or risk compromised data.

Preferably, the method also includes the step of distributing the uncompacted sample within the bag prior to the second measuring step (during the encasing step) such that the material sample is substantially uniformly spread across a major portion of the bag. In one embodiment, the loose mixture is held in a sub-container which is itself held encased and sealed in the bag. The sub-container is configured to allow water to enter during the immersion step after the opening is introduced in the bag or after the seal integrity is destroyed. The method can result in the calculation of the maximum theoretical specific gravity based on the sub-container and bag density value determined during the density determination step.

Another aspect of the present invention is a method for analyzing the density of a bituminous paving mixture comprising one or more of an uncompacted or loose material sample. The method includes the steps of inserting the bituminous paving mixture material sample into a sub-container having at least one aperture formed therein and encasing the paving mixture material sample in a sealant such that the sealant substantially conforms to the sub-container with the-material sample held therein. The encased sub-container is then immersed with the paving mixture material sample held therein in a liquid displacement bath. An opening is introduced into the sealant and liquid from the liquid displacement bath is allowed to enter the sub-container and contact the paving mixture material sample held therein as the sub-container with the paving mixture material sample is immersed in the liquid displacement bath. The weight of the opened sealant with the sub-container and the paving mixture material sample while immersed in the liquid displacement bath is obtained subsequent to the introducing step and the density of the paving mixture material sample is determined by correction of the previously determined sub-container and sealant density.

In a preferred embodiment, the sealant is a bag and the material sample comprises uncompacted bituminous materials and/or loose aggregates and/or asphalt mixture.

It is yet another aspect of the invention to provide a method of evaluating the density of material specimens using a liquid displacement bath. The method includes the steps of: encasing a material specimen in a conformable sealant material; evacuating the encased material specimen; and immersing the encased material specimen in a liquid displacement bath while the encased material specimen is held in an evacuated state within the sealant material.

In a preferred embodiment, the conformable sealant material is a bag. It is also preferred, particularly for material specimens comprising uncompacted paving mixtures or loose aggregates, that the method also include the step of inserting the (loose) material specimen into a sub-container prior to the encasing step; the sub-container is configured and sized to hold the material specimen therein and/or to reduce compaction of the loose sample by the sealant's contact with the material specimen.

Another aspect of the present invention is a sealable, uncompacted material sample used for evaluations involving liquid displacement tests. The sealed material sample includes a quantity of uncompacted material forming a material sample which is selected from a larger mixture quantity such that it is representative of the larger mixture's composition. The sealed sample also includes a preformed resilient bag having a sealed edge portion and a predetermined apparent density value associated therewith. The bag is configured and sized to hold the quantity of uncompacted loose material sample therein. The quantity of loose material sample is sealed within the resilient bag such that a region of the bag proximate to the sealed edge is free of the uncompacted loose material sample. The preformed bag is configured to sealably encase the loose material such that the bag outer walls substantially conform to the sample's exterior surface contour and prevent the migration of water therein (while the bag remains sealed) during immersion in a liquid water bath. The predetermined apparent density value is used to establish the density of the uncompacted loose material sample.

In a preferred embodiment, during analysis, the sample specimen has a first sealed configuration and a second unsealed configuration. In the sealed configuration, the sample is evacuated of substantially all air therein. Voids are created in the bag resulting from irregularities (coarse, non-congruent or uneven profiles and shapes) of the constituents comprising the sample and the degree of conformance of the evacuated collapsed bag to the sample. The second unsealed configuration is defined by an opening introduced or formed into the sealed bag (the opening introduced therein while the sample and bag are held completely immersed in the liquid bath). During liquid displacement based analysis, the opening destroys the integrity of the sealed encased bag holding the bituminous material sample and allows fluid to enter therethrough to contact the quantity of uncompacted bituminous material (and thus, fill the remaining voids within the bag).

In a preferred embodiment, the uncompacted loose material sample comprises paving mixtures of asphalt and/or a plurality of different types and size aggregates.

Another aspect of the present invention is a vacuum system for preparing and sealing in a pre-formed bag an uncompacted or compacted material specimen for liquid immersion evaluation. The vacuum system comprises a vacuum apparatus with a vacuum receiving chamber having a perimeter defining an internal holding region with a floor. The holding region is configured and sized to receive a preformed bag with a coarse material sample held therein. The vacuum apparatus comprises a sealing ledge located in the vacuum chamber along a perimeter portion thereof. In operation, the sealing ledge is configured to apply heat to and seal an edge of the preformed bag together. The vacuum apparatus also includes an air channel and a vacuum pump in fluid communication with the vacuum chamber. The vacuum apparatus additionally includes a support member positioned or residing on the floor (either directly or indirectly). The support member is configured and sized to hold the specimen in the preformed bag. In operation, the support member is configured and held within the vacuum chamber so that it can translate toward the sealing ledge. As such, the support member is mounted to the vacuum chamber or held therein such that it is substantially free to move in the direction of the sealing means or ledge to help support the weight of the specimen in the bag to inhibit the introduction of punctures or tears during the evacuation or sealing process.

The present method is easily adaptable to specimens having different (increased sizes). This facilitates the laboratory analysis of many different types and sizes of compacted specimens. Indeed, due to the sizes of aggregates used in recent mixtures, it is desirable to increase the size of the specimen undergoing evaluation, whether the specimen is prepared in the laboratory and/or extracted from the field. Typically, the size is increased from conventionally sized specimens having about a 100 mm (4 inch) diameter to specimens having about a 150 mm (6 inch) diameter for different thicknesses.

The present invention also provides methods for determining apparent bag (or other conformable sealant) density with a plurality of different reference specimens of varying size and/or geometry in order to provide improved apparent bag density reference values (more accurately reflecting the behavior of the sealant during specimen measurement). These values can conveniently be predetermined at a production site, saving labor time at the laboratory-testing site. The bag density values are then useable to calculate material density of field material samples measured with sealed bags used according to the present invention. For example, the present invention provides solid reference samples, reference samples with predetermined void configurations formed on the surface thereof, asphalt samples with known void content/thickness, and loose reference samples mixture comprising a plurality of loose non-absorbent articles such as spherical solid material balls (such as marbles), and the like. For the loose reference mixture, a sub-container with water entry ports configured thereon can also be used to hold the loose mixture within the bag (the bag encases the sub-container which holds the mixture).

Advantageously, the present invention provides a reliable and easily used method for determining the maximum specific gravity and/or density of uncompacted or loose bituminous material samples with water displacement evaluation techniques. This technique can also be used to assess asphalt permeability or porosity. Further, unlike conventional test techniques, the methods of the instant invention evacuates the sample in the absence of water and, thus, does not draw water into the vacuum pump during testing procedures.

BRIEF DESCRIPTION OF THE DRAWINGS

The accompanying drawings, which are incorporated in and constitute a part of the specification, illustrate embodiments of the invention and, together with description, serve to explain principles of the invention.

FIG. 1B is a perspective view of a system according to the present invention similar to that shown in FIG. 1A, illustrated without the specimen therein to show a sliding support mechanism upon which the specimen in the bag is positioned during the evacuation/sealing process.

FIG. 2 is a side section view of the specimen in the preformed bag positioned in the apparatus of FIG. 1A.

FIG. 3 is a side section view of an alternative embodiment of a vacuum apparatus and sealing means according to the present invention.

FIGS. 4A, 4B, and 4C are plan views illustrating preferred embodiments of preformed resilient bags according to the present invention.

FIG. 21 is a tabular display of actual bag density determinations and core density calculations for a plurality of samples (including four different material types) which were sealed with the same vacuum setting (about 25 in Hg) according to the present invention.

FIG. 22 is a tabular display of a suitable data sheet for collecting and manipulating the raw data to establish core density according to the present invention.

FIG. 24 is an exemplary tabular data sheet for collecting and manipulating the raw data to establish the maximum theoretical specific gravity according to the present invention.

FIG. 26 is a schematic illustration of a substantially solid reference standard configured according to the present invention with a predetermined air void pattern defining a known air void content.

FIG. 27 is a schematic illustration of a reference standard configured from asphalt according to the present invention.

DETAILED DESCRIPTION OF PREFERRED EMBODIMENTS OF THE INVENTION

Figure 1A:
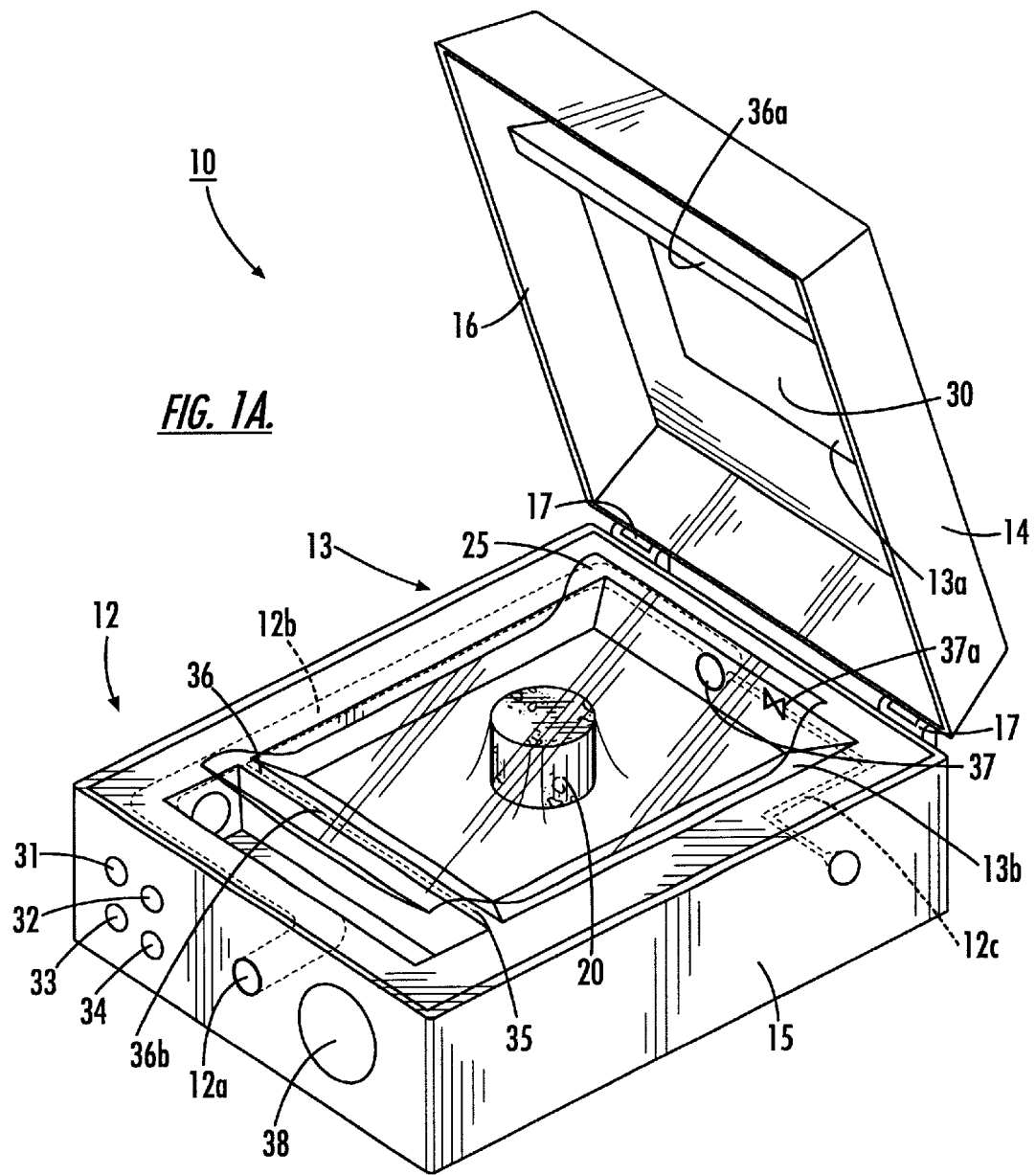
FIG. 1A is a perspective view of a system for sealing a dense material specimen to inhibit liquid contacting the specimen during liquid displacement tests according to the present invention. The figure illustrates a porous material specimen in a resilient preformed bag positioned in a vacuum apparatus with an internal chamber and internal sealing means and controls for vacuum settings and exhaust speed adjustment according to a preferred embodiment of the present invention.

The present invention will now be described more fully with reference to the accompanying drawings, in which preferred embodiments of the invention are shown. This invention may, however, be embodied in many different forms and should not be construed as limited to the embodiments set forth herein; rather, these embodiments are provided so the this disclosure will be thorough and complete, and will fully convey the scope of the invention to those skilled in the art. Like numbers refer to like elements throughout. In the drawings, layers or regions may be exaggerated for clarity.

Generally described, the present invention is directed to a method, system, apparatus, and water resistant jacket (which is preferably configured as a preformed bag) which acts to seal a porous sample from water infiltration in such a way that the sealing material is consistent over many samples and displaces a constant volume of liquid when used in liquid displacement tests, thereby improving the operator-reliant methods used at evaluation laboratories in the past. As used herein, the term "liquid" includes water, oils, aqueous mixtures, and preferably miscible blends thereof. In a preferred embodiment, the liquid displacement test is a water displacement test.

FIG. 1A illustrates a preferred embodiment of a system 10 for sealing a coarse porous material specimen in preparation for liquid displacement tests according to the present invention. As shown, the system 10 comprises a vacuum apparatus 12 with an internal (encloseable) vacuum chamber 13 having corresponding upper and lower and recesses 13a, 13b. The vacuum chamber 13 includes an upper lid 14 and a base 15, the upper recess 13a being formed in the lid 14 and the lower recess 13b being formed in the base 15. The upper and lower recesses 13a, 13b are sized and configured to receive a material specimen 20 positioned in a preformed bag 25 therein. In operation, the lid 14 is operably associated with a hinging portion 17 and pivots about the base 15 and closes to contact the base 15 and enclose the bag 25 and specimen 20 in the vacuum chamber 13. Preferably, as shown, the lid 14 includes a gasket 16 positioned around the rim to facilitate proper sealing of the apparatus 12 during use. Also as shown, the apparatus 12 includes a viewing port 30 which allows an operator to view the status of the contents during use.

As is also shown, the vacuum apparatus 12 also includes a vacuum pump 12a in fluid communication with a vacuum channel 12b which extends to an exhaust port 37. The exhaust port 37 is operably associated with an air channel 12c control rate adjustment means such as a valve 37a. The vacuum apparatus 12 also preferably includes a vacuum pressure adjustment 31, a timer adjustment 32 for the heater strip 36, an on/off switch 33, a stop button 34, and a gauge 38 to indicate the actual vacuum pressure in the chamber 13.

It is also preferred that system 10 include sealing means 35. As shown, in this embodiment, the vacuum apparatus 12 is configured with internal sealing means 35. In the illustrated embodiment, the sealing means 35 is shown as a heating element or strip 36 in alignment with two opposing bag clamps 36a, 36b. The sealing means 35 is mounted in the vacuum chamber 13 and includes the two opposing longitudinally extending clamps 36a, 36b which are configured to contact when the lid is closed over the base 15 and a heater strip 36. The internally mounted heater strip 36 can be incorporated into or positioned adjacent to one or both of the opposing heater clamps 36a, 36b. Alternatively, the heating and clamping means for sealing the edge portions of the bag 25 can be configured to extend around the perimeter of the bases 14 and 15 in a manner which allows the apparatus 12 to seal more than one side (or portion of one side) of the bag, such as two, three or even all sides of the bag, while the bag and specimen are held within the chamber 13 of the vacuum apparatus 12 (not shown).

As shown, in position, the front (open or unsealed portion) of the preformed bag 25 overhangs the surface of the lower clamp 36b. In operation, vacuum is pulled on the chamber 13 via vacuum pump 12a, vacuum channel 12b, and the exhaust port 37 until the vacuum chamber 13 reaches an appropriate vacuum level, or the air is evacuated or forced from the bag 25. The heater element 36 is preferably positioned in the bottom clamp 36b. After the vacuum reaches the appropriate level, the bottom clamp 36b is elevated and the heater element 36 activated. Thus, the clamps 36a, 36b exert a sealing force pinching against the opposing walls of the bag while the heater element is activated to securely seal the open edge portion of the bag while the bag 25 is held inside the vacuum apparatus 12 (i.e., prior to removal from the chamber 13). After the bag 25 is sealed, air is allowed into the chamber 13 through the exhaust port 37 which forces the sealed bag 25 to conform to the surface of the specimen 20. Preferably, the air enters through a restricted air channel 12c associated with the exhaust port 37. That is, the exhaust port 37 opening is controlled via valve 37a so as to control the rate of airflow into the chamber. This rate control helps control the force at which the bag walls conform to the specimen surface, thereby reducing the likelihood that the walls of the bag will puncture due to an abrupt return to atmospheric conditions attributed to an accelerated or uncontrolled exhaust rate or to forces associated with the re-introduction of air.

FIG. 2 illustrates the system 10 with the material specimen 20 and bag 25 positioned in the vacuum chamber 13 and the lid 14 with respect to the base 15. A suitable vacuum apparatus can be obtained from Ary Corporation, Kansas City, Mo. The commercially available apparatus is preferably modified to add vacuum and air exhaust controls according to the present invention. A modified vacuum system identified as a CoreLok™ System can be obtained from InstroTek, Inc., of Raleigh, N.C.

In order to reduce the likelihood that the bag 25 will puncture during the sealing process, the specimen 20 in the bag 25 is positioned on a support member 60 as shown in FIG. 1B. During operation, the specimen 20 in the unsealed bag 25 is held by the underlying support member 60. The support member 60 is positioned in the vacuum chamber 13 such that it is able to translate toward the sealing means 35. As shown by the arrow designated by the letter "H", the support member 60 can translate in a horizontal direction. In a preferred embodiment, the support member 60 is a non-complex support plate comprised of a low-friction material such as DELRIN® resin. In one embodiment, the support member 60 is about ¼ inch thick and is sized and configured to be able to support the specimen 20 thereon inside the vacuum chamber 13. Preferably, the support member 60 is about 8 inches long by 7 inches wide (amply able to hold a 6 inch diameter specimen, and preferably providing a surface larger than the sample for easy alignment by an operator thereon). As is shown, a gasket material 61 can be attached to the upper surface of the support member 60 so as to provide a cushion contact interface for the bag 25. An example of a suitable gasket material is a high-density rubber. Thus, in position, the specimen 25 presses against a portion of the wall of the bag and both the bag and the specimen are supported by the underlying support member 60. In operation, in the vacuum chamber 13, the bag 25 is pulled or drawn against the coarse exterior of the specimen held therein as the bag is pulled forward toward the sealing ledge 35, during which the bag is one or more of evacuated, sealed, and reintroduced to ambient conditions. The exposure of the bag 25 to forces during the process potentially introduces an opportunity for the bag 25 to puncture proximate the coarse exterior of the specimen 20 as the bag is pulled thereagainst. The support member 60 cushions the weight of the specimen 20 as it presses against the bag 25 and also translates concurrently with the bag 25 to hold the weight of the specimen as it moves which reduces the forces acting on the bag and the likelihood that the bag will puncture.

Although the support member 60 is shown as a relatively non-complex component, i.e., a slidable substantially planar support plate, it will be appreciated by those of skill in the art that a number of alternative support member configurations and mechanical attachment means can be employed according to the present invention. For example, a side-mounted slidable platform (similar to a drawer) can be mounted to the chamber inner walls so as to provide the requisite support and allow horizontal movement to support the specimen during the process. Alternatively, rollers or other rotating or sliding surfaces or components can be formed on or attached to the bottom or sides of the support member 60 (not shown). The support member can also be provided by an electro-mechanical sliding mechanism which is controllable by a computer programmable controller. For example, the electro-mechanical sliding mechanism can be configured with a motor, drive means, and controller which operates to automatically move the sliding mechanism (and thus, the sample) at appropriate times during the evacuation/sealing/collapsing procedure (facilitating the movement thereof) to further reduce forces introduced on the bag (particularly for heavy samples).

In addition, the top surface 61s can be configured in a number of alternative configurations. Although shown with a top cushion surface formed of two gasket strips 61, a single strip or a plurality of strips or other shapes of cushions can be employed. Alternatively, the top surface 61s can be configured as a receiving channel sized to correspond to the particular specimen undergoing evaluation (typically a plurality of this type of support members would be needed, each corresponding to the specimen size under evaluation). Of course, care should be taken to inhibit any sharp edges formed thereon which would contact the bag and specimen during operation to reduce the likelihood that punctures will occur.

In a preferred embodiment (not shown), the system 10 is configured such that a scale is integrated into the bottom base 15 of the vacuum apparatus 12 thereby allowing an automatic measure of the air weight of the specimen 20 to reduce the number of steps needed to be taken by an operator to establish the density of the specimen undergoing evaluation. This automatic weight measure can then be directed into a computer memory or computer program to allow easy semi-automatic computation of the density based on the input measurement parameters. Of course, the automatic input of the air weight can also reduce the separate listing of data needed to be input by laboratory operators thereby reducing operator clerical errors.

FIG. 3 illustrates an alternative (direct pull) system 10' with a vacuum apparatus 12' and a bag and specimen held external to the vacuum apparatus 12' during operation. The front portion of the bag 25 is positioned to overhang a portion of the vacuum chamber 13' while a major portion of the bag 25 is held external to the vacuum apparatus 12' during operation. The bag 25 may be held in position by a fixture or manually via lab personnel. In any event, in order to provide proper operation, the bag 25 is preferably held static while the vacuum apparatus 12' is engaged with the front edge of the bag. Indicia of depth may also be formed or positioned on the surfaces of the front portion of the bag 25 to help an operator positionally align the bag to a desired vacuum chamber entrance depth across the open edge of the bag to facilitate proper engagement (not shown).

As shown in FIG. 3, opposing upper and lower gaskets or seals 16' facilitate the sealing of the vacuum apparatus 12' when the lid and base 14', 15' are closed. In this embodiment, the sealing means is a laterally extending strip heater 36' which includes an upper clamping surface 36a' and a lower clamp support surface 36b' positioned in the apparatus 12' but mounted external to the vacuum chamber 13' (closer to or adjacent the receiving edge of the apparatus 12'). This heater arrangement allows the seal to be applied substantially contemporaneous with the vacuum to maintain the bag in its de-pressurized state, or in its surface collapsed or conformal shape (after the bag has been exposed to the desired pressure for the desired time but before the pressure or substantially immediately after the pressure has been removed). Preferred processing times and pressures will be discussed further below. A suitable vacuum apparatus can be obtained from Ary Corporation in Kansas City, Mo.

Other vacuum systems can be employed, such as for example, a direct connect or nozzle type vacuum system. In this embodiment, a vacuum pump and hose are in communication with a nozzle which is insertable into an opening formed in the bag 25 with the bag clamped securely therearound. Of course, the bag can be modified to configure the bag to accept the nozzle in manner which can facilitate the airtight seal between the nozzle and the bag during the vacuum step. For example, the open edge of the bag can be pre-sealed to along a major portion of the bag to provide a smaller opening to accept the nozzle during the air removal step. In operation, the nozzle directs the vacuum into the chamber of the bag and removes the air (not shown). Thus, similar to the externally held bag and specimen shown in FIG. 3, the direct-connect nozzle can be conveniently inserted into a bag to conform the bag to the shape of the specimen. An external sealing means can then be applied such as a manual sealing method or a sealing device such as is used in the commercial food preparation industry.

FIGS. 4A, 4B, and 4C illustrate preferred embodiments of a preformed resilient bag 25 according to the present invention. The preformed bag 25 includes two opposing walls 26, 27 which define the holding chamber 29 for the material specimen 20. Preferably, the preformed bag 25 is manufactured at a production facility remote from the laboratory or evaluation site such that it has three co-joined sides and a single open end when it is received at the evaluation site. The preformed configuration provides a ready-to-use bag 25 which the technician can employ with minimal preparation time at the laboratory test site.

Figure 14:
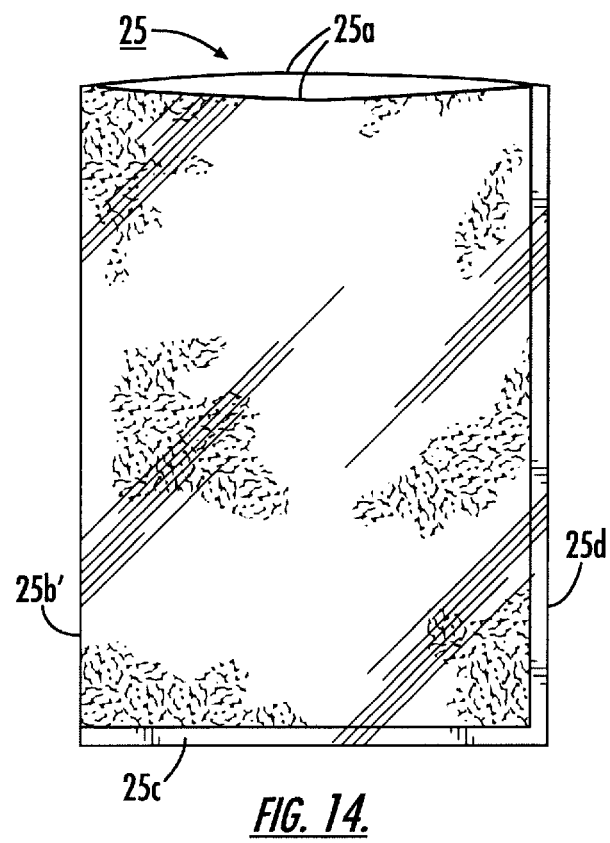
FIG. 14 is a top view illustrating a preformed bag having three co-joined sides, two of which are sealed together and one of which is provided by the unitary fold line of the material layer according to the present invention.
Figure 14A:
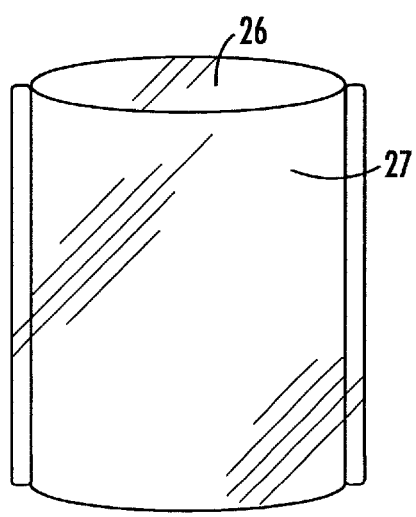
FIG. 14A is a perspective view of an alternate embodiment of a preformed bag having a preformed extruded bag forming a cylindrical bag where the two open ends can be joined at a laboratory evaluation use site.

FIGS. 4A–4C illustrate a preferred embodiment of a preformed bag 25 wherein the two opposing walls 26, 27 are co-joined on three sides by attaching the opposing sides 26, 27 at three corresponding sealing edges 25b, 25c, 25d. The three sides 25b, 25c, 25d thereby provide a continuous sealed edge perimeter. The fourth side 25a is left open so that a material specimen 20 can be inserted at the laboratory or use site (remote from the production site). FIG. 14 illustrates that the three co-joined sides 25b', 25c, 25d can be alternatively attached or formed. As shown, the first co-joined side 25b' is formed by a use of a folded unitary (single sheet of one or more material layers). Of course, the unitary portion of the bag (not requiring a sealed edge) can be alternatively configured on the bag such as on the end 25c opposing the open end 25a.

Figure 15A:
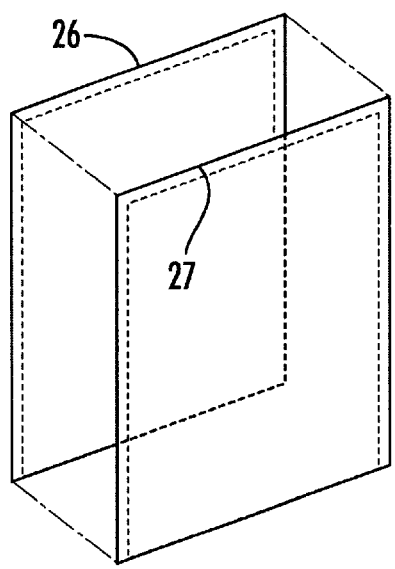
FIG. 15A is an exploded perspective view illustrating a resilient compressible bag which is formed by overlaying and sealing two pieces of material around the perimeter according to the present invention.
Figure 15B:
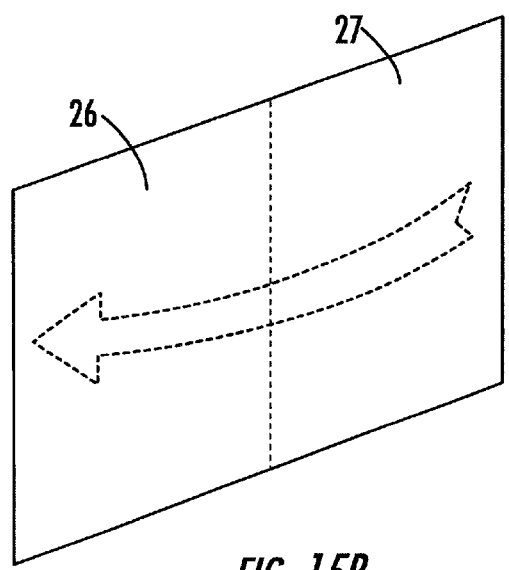
FIG. 15B is a perspective view of a unitary material bag according to the present invention illustrating fold lines therefor.

Alternatively, the "preformed bag" 25 of the present invention can be provided as a preformed bag structure which is joined along less than three sides 25b, 25c, 25d at a remote production site, such as along one or two sides, and still minimize the amount of trimming or even prevent the step of material trimming at the evaluation site at all. When two sides are joined, preferably two opposing sides such as those shown by sides 25b, 25d, the preformed bag 25 structure provides a "bag core" with a chamber 29 which can allow the technician to assemble the specimen 20 into the chamber 29 of the water jacket with the addition of one or two more supplemental or "side" sealing steps at the evaluation site, but still without requiring the operator to trim off unknown amounts of material and undesirably potentially degrading the reliability of the test results. FIGS. 15A and 15B illustrate two preferred fabrication configurations. FIG. 15A illustrates two separate sheets of material with one or more sides sealed at a production site. FIG. 15B illustrates a unitary pre-cut material sheet which can be folded along the fold lines to define one co-joined side (shown in dotted lines) and preferably sealed along the other two edges at a production site.

Figure 15C:
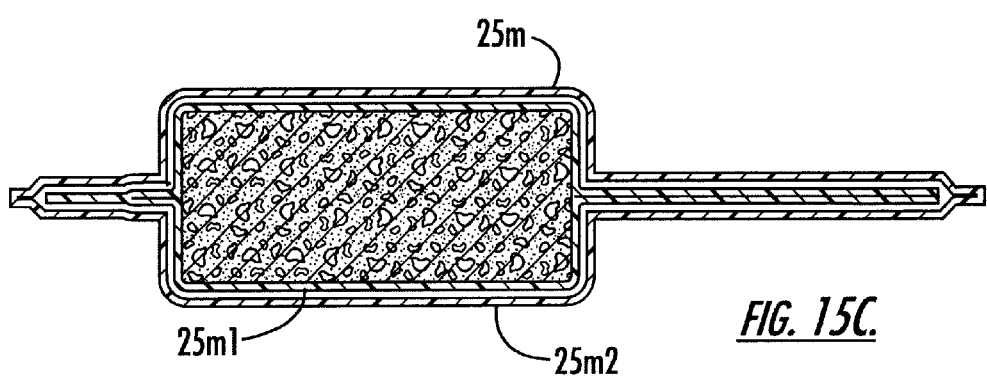
FIG. 15C is side section view of a specimen sealed in a multi-bag embodiment according to the present invention.

FIG. 15C illustrates a multi-bag embodiment 25m of a water jacket according to the present invention. As shown, the specimen is held inside a first bag 25m1 which is positioned within an outer second bag 25m2. The first bag 25m1 can be formed of a different material than the second bag 25m2. Preferably, the inner or first bag 25m1 is formed of a durable resilient material to resist punctures as it conforms to and rests against the exterior contours of the specimen 20. It is also preferred that the first bag 25m1 be sized and configured to be enclosed within the second bag 25m2. The first bag 25m1 does not need to be separately sealed or indeed, as shown, sealed at all.

In one embodiment, as illustrated in FIG. 4B, at least one of the inner surfaces of the two opposing walls 26, 27' includes a series of air channels 28 formed thereon. Preferably, the air channels 28 are coextensive with one of the walls 26, 27'. The air channels 28 are configured such that air can more easily escape from the bag as the chamber 29 deflates to rest against the exterior surface of the internally held specimen 20 and thus facilitate the surface conformal collapse of the bag against the exterior surface of the specimen (FIG. 9D). FIG. 4C illustrates that the air channels 28 can be formed onto the inner surface of both walls 26', 27'. Air channels 28 can be formed in a number of suitable configurations and are preferably configured to interconnect to the open edge portion of the bag 25. It is preferred that bags 25 with air channels 28 be used with the externally held bags used with direct pull vacuum equipment such as that shown in FIG. 3 while the bags 25 which are free of air channels 28 (such as those shown in FIGS. 4A, 5A, and 6A) be used with the vacuum apparatus of FIGS. 1A and 1B. Bags 25 of either type may be used with direct connect or nozzle type vacuum systems as described above.

In a preferred embodiment, the material specimen 20 is a porous compacted material specimen typically having interconnecting voids such as a compacted soil, concrete, aggregate, and bituminous samples. As such, the density measurement methods of the present invention are preferably used to analyze compacted material specimens which comprise, either alone or in combination, one or more of compacted soil, concrete, aggregate (loose and/or compacted), and compacted asphalt and/or bituminous material samples. Typically, the compacted material specimen 20 is a cylindrically extending dense core extracted from a roadway pavement or molded in a laboratory with mixed material samples representative of materials used in the field and, as such, this type of core includes a rough or coarse exterior surface. Of course, the specimen is not limited thereto as discussed above. Further, the material specimen 20 can be an aluminum block which typically has a smooth surface and a known density. As such, the aluminum block can act as a standard reference and can be used to determine the standard density for each type or size bag 25. Of course, other solid materials and configurations can also be used to provide the known standard reference.

Preferably, the compacted material specimen 20 has a four or six inch width or diameter and is on the order of from about 1–6 inches thick. Because, the compacted material specimens 20 are typically formed in standardized sizes, a set of bag 25 sizes can be conveniently be provided to allow a technician to select one from a collection of several preformed sizes. The particular bag selected is configured and sized to contain the particular size (or a range of sizes including that size) material specimen 20 and/or porosity or coarseness of the specimen undergoing analysis.

Preferably, the diameter of the cylindrically molded or field obtained specimens 20 (or length of sawed specimens) is at least equal to about four times the maximum size of the aggregate used therein. It is also preferred that the thickness of the specimen 20 is at least one and one half times the maximum size of the aggregate used therein. For example, for many roadway compacted mixtures, it is recommended that the specimen 20 be configured with about a 150 mm (6 inch diameter) specimen 20 having a thickness of at least about two inches.

For specimens having an exterior surface which is coarse, the preformed bag 25 is preferably configured to be puncture-resistant, as the bag 25 collapses to contact and conforms to the exterior surface of the material specimen during the sealing operation. A preferred embodiment of the present invention is therefore a puncture-resistant bag which is conformable to the exterior surface of the specimen. The puncture resistance can be provided by one or more of, material selection (type, size, and thickness), use of multiple layers of materials, use of multiple numbers of bags, and the use of reinforcement patches in areas of high-contact force. Preferably, the puncture resistance is also provided by a method which controls the rate of exhaust into and and/or evacuation out of the vacuum chamber 13 at the exhaust port 37 in a manner which is sufficient to slow the abrupt introduction of air back into the chamber 13 after sealing.

Figure 5A:
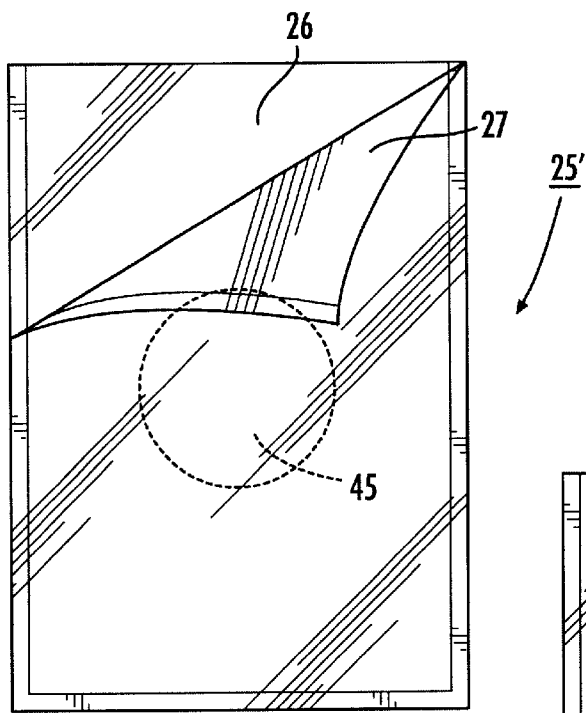
FIGS. 5A, 5B, and 5C are plan views illustrating the preformed resilient bags of FIGS. 4A, 4B, and 4C with integral reinforcement patches according to the present invention.
Figure 5B:
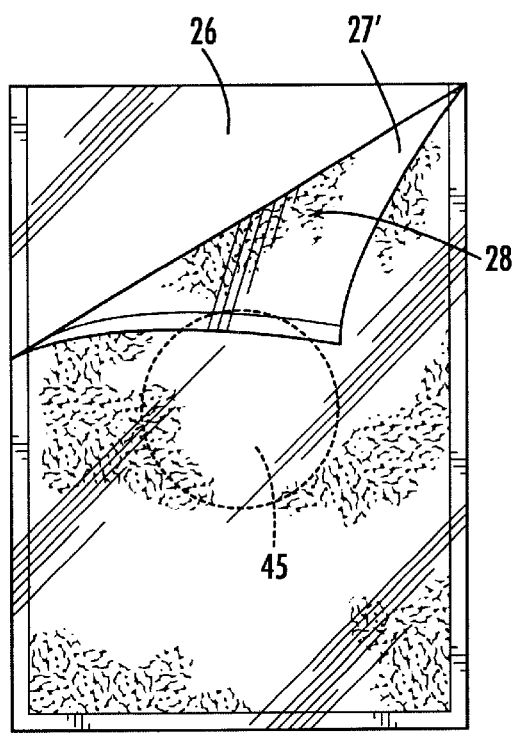
Figure 5C:
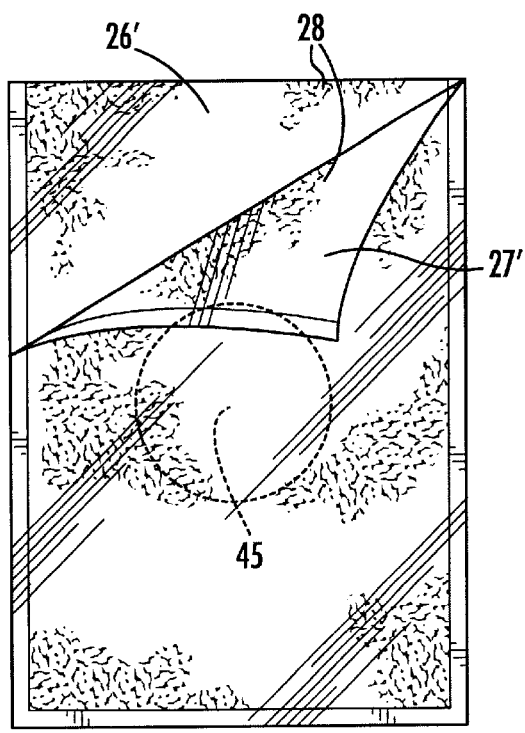

FIGS. 5A, 5B, and 5C illustrate preformed bags 25' with at least one integral reinforcement patch 45. Preferably, the reinforcement patches 45 are formed onto opposing internal surfaces of the first and second walls 26, 27. It is further preferred that the reinforcement patch 45 is configured to correspond to the shape of the upper or lower surface of the material specimen. Inasmuch as many of the bituminous material specimens used in construction are cylindrical, it is preferred that for this application, the reinforcement patch 45 be configured substantially as a circle and positioned on the bag 25 such that it overlies the specimen when the material specimen 20 is positioned therein. Of course, the reinforcement patch configuration will preferably correspond to the particular specimen undergoing analysis. In addition, other configurations side reinforcement patches may also be used and are preferably sized to correspond with the thickness and shape of the sides of the particular specimen undergoing analysis.

Figure 6A:
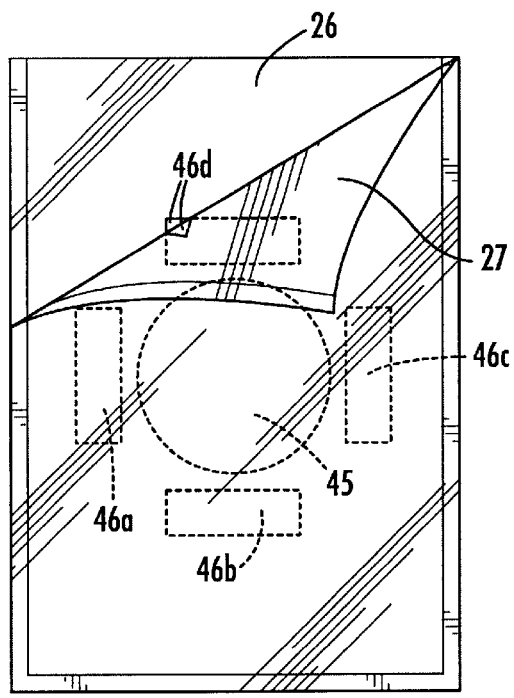
FIGS. 6A, 6B, and 6C are plan views illustrating additional embodiments of integral reinforcement patches according to the present invention.
Figure 6B:
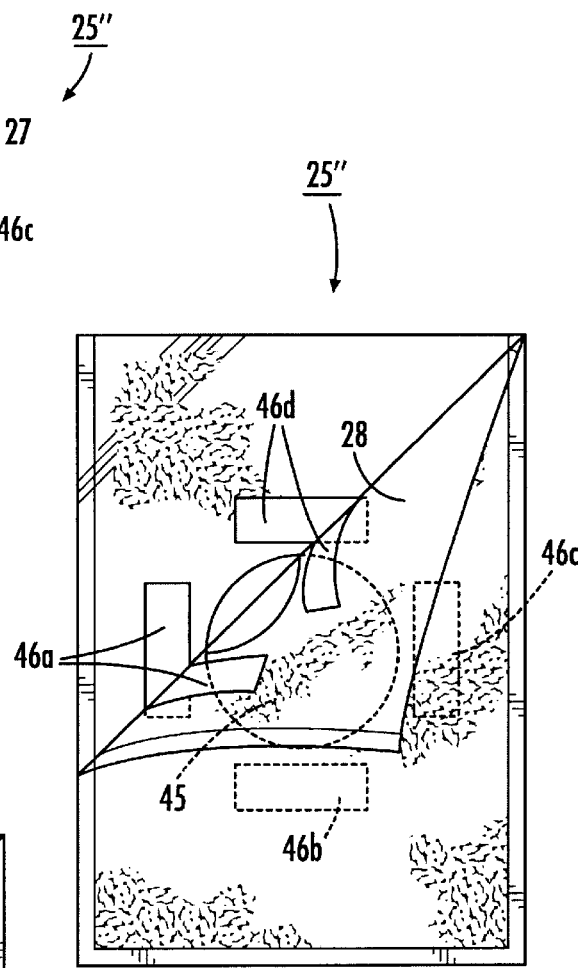
Figure 6C:
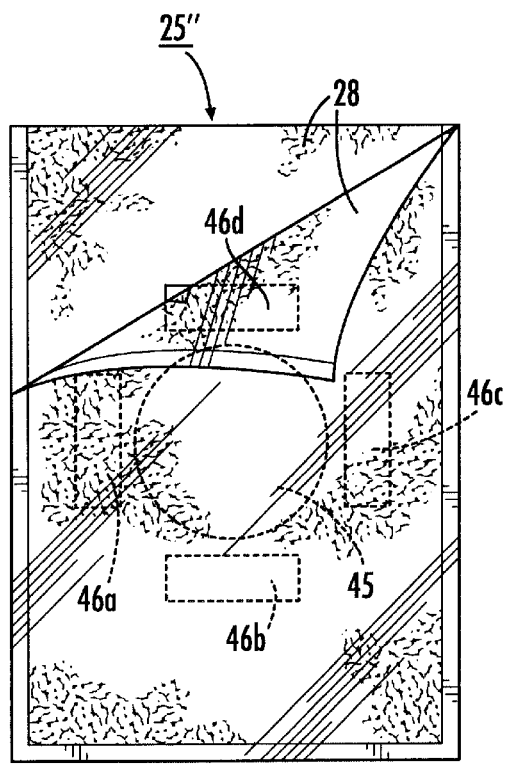

FIGS. 6A, 6B, and 6C illustrate preformed bags 25" with alternate embodiments of integral reinforcement patches according to the present invention. As shown, the preformed bags 25" include at least one wall of the bag 26, 27 with a centrally positioned circular patch 45 and a plurality of peripheral reinforcement patches 46a, 46b, 46c, 46d positioned on or formed into the bag to provide additional strength in predetermined regions of the preformed bag 25". Preferably, the peripheral reinforcement patches 46a, 46b, 46c, 46d, are positioned on the walls of the bag 26, 27 such that they fold over a portion of the sides of the specimen 20 as the bag 25 collapses to conform to the exterior shape of the specimen (FIG. 9D). Of course, other reinforcement patch configurations can also be employed within the scope of the present invention and the present invention is not intended to be limited to the exemplary reinforcement configurations shown herein. For example, circular patches can be applied to the top and bottom of the specimen and also applying cylindrical or linear wrapped patches onto the specimen to wrap around the sidewalls of the specimen. In this example, substantially all of the exterior surfaces can have reinforcement patches applied before sealing in the bag.

Figure 7:
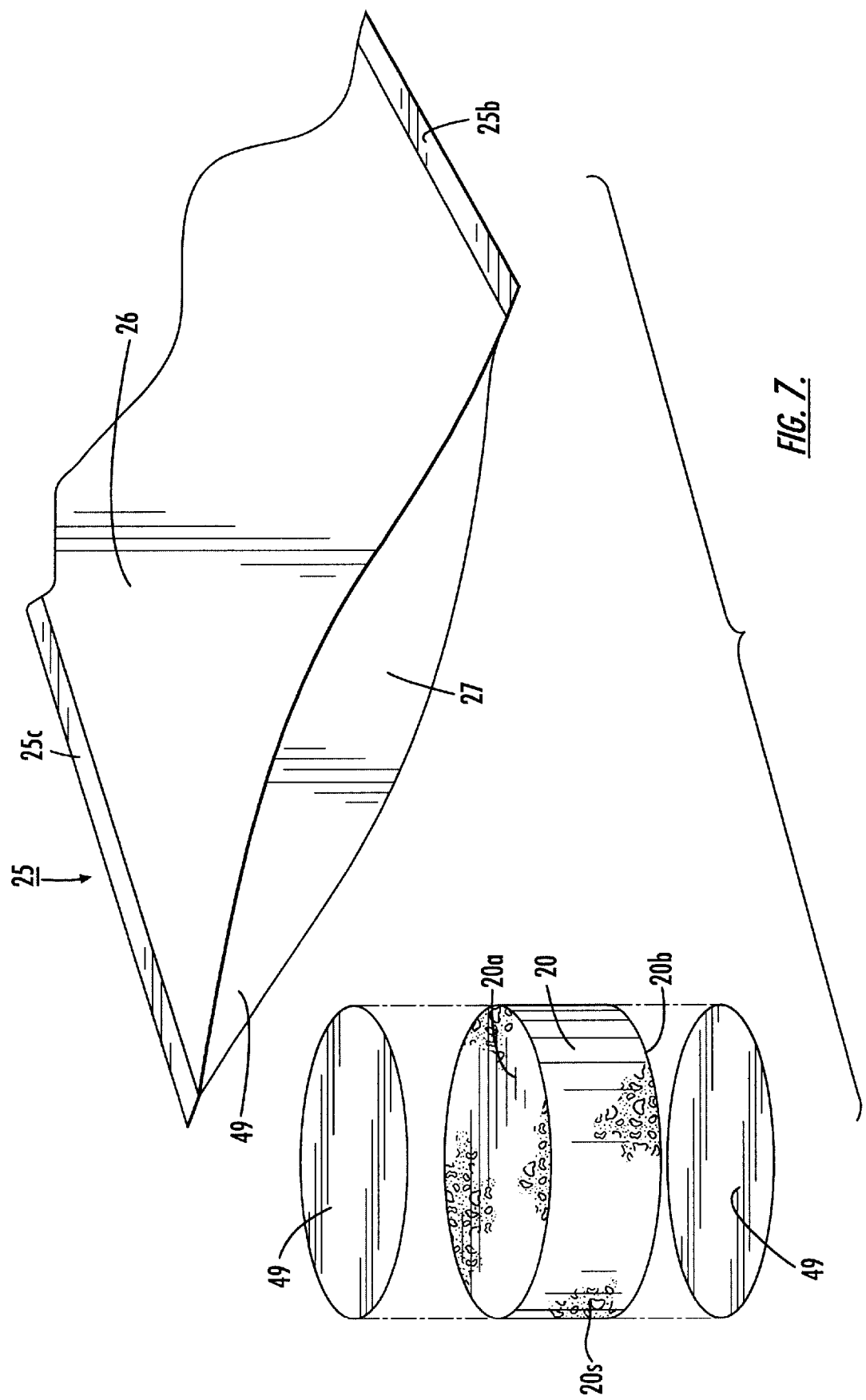
FIG. 7 is a partial exploded perspective view illustrating supplemental reinforcement patches positioned over a specimen prior to insertion into a preformed bag according to another embodiment of the present invention.

FIG. 7 illustrates an alternate embodiment of supplemental reinforcement patches 49. As shown, these supplemental reinforcement patches 49 are substantially flat circular patches which are positioned onto the top and bottom exterior surfaces 20a, 20b of the specimen 20 itself before the specimen 20 is inserted into the chamber 29 in the preformed bag 25. Of course, a single supplemental patch or portion of a patch can also be used for a corresponding selected single surface or portion of a single surface. In addition, small amounts of adhesive, or, preferably, a single-sided adhesive material can be used to attach to the surface of the specimen to hold the supplemental patch 49 in position during the insertion step. In operation, as the walls 26, 27 of the bag 25 collapse to contact the exposed coarse top and bottom surfaces 20a, 20b of the specimen, the supplemental reinforcement patches 49 act much like the integral reinforcement patches 45 to inhibit the puncture of the walls 26, 27 due to the contact with the coarse exterior surface. In addition, the supplemental reinforcement patches 49 can be configured to cover the sides and the top and/or bottom surfaces of the material specimen 20 and are preapplied to the specimen prior to insertion of the specimen 20 into the preformed bag 25.

Figures 9A, 9B:
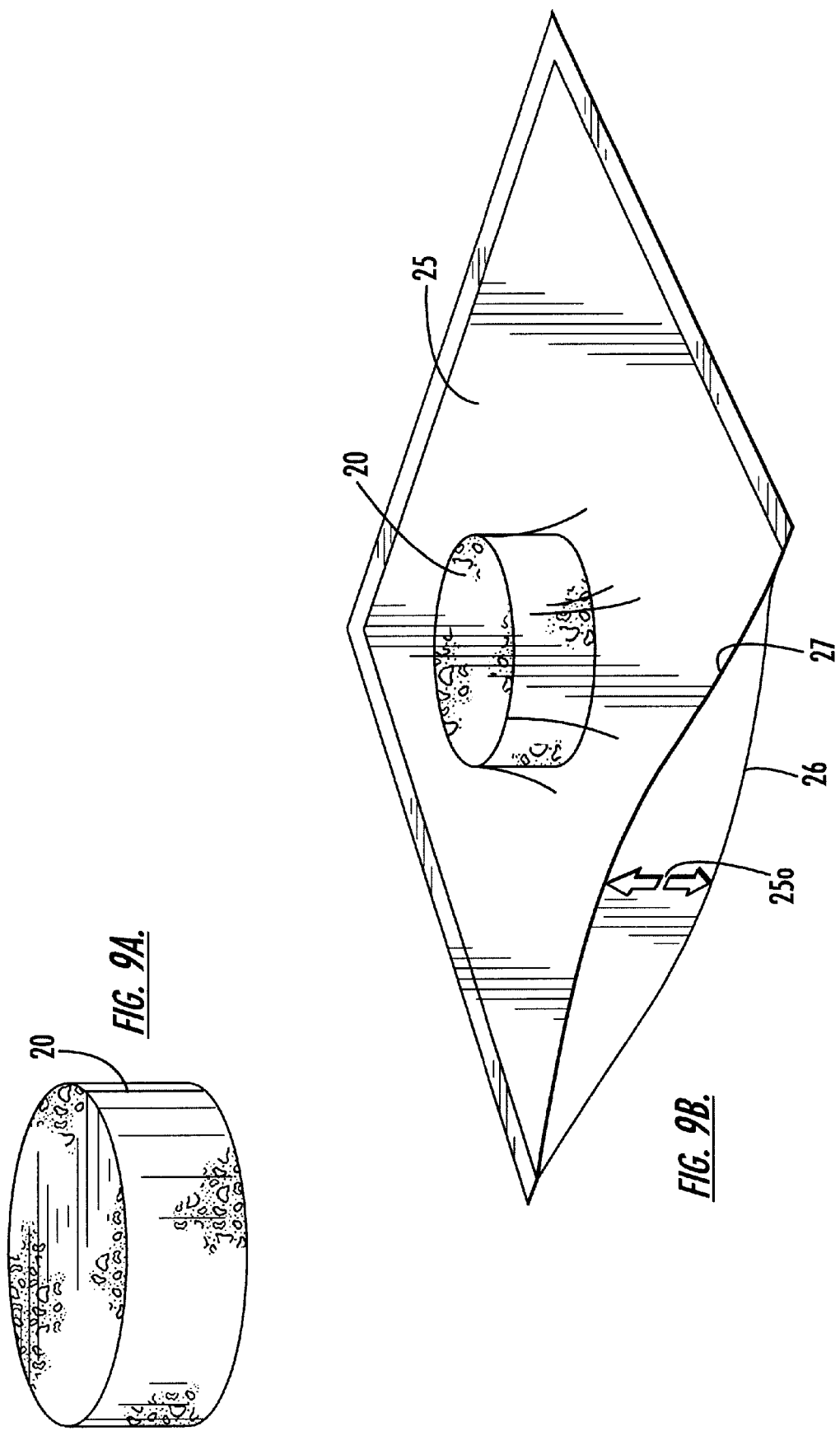
FIG. 9A is a perspective view of a porous specimen.
FIG. 9B is a perspective view of the porous specimen shown in FIG. 9A positioned in a preformed bag according to the present invention.
Figure 9C:
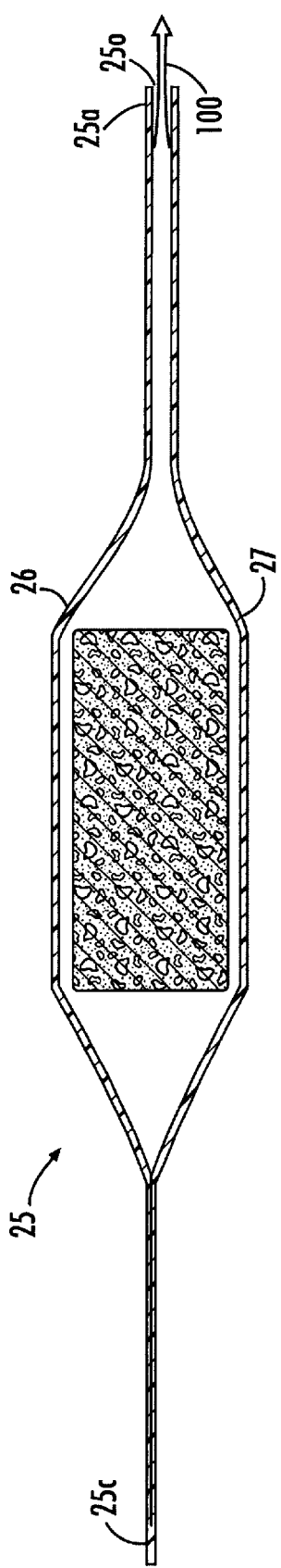
FIG. 9C is a side section view of the specimen and bag shown in FIG. 9B illustrating air being directed out of the bag opening.
Figure 9D:
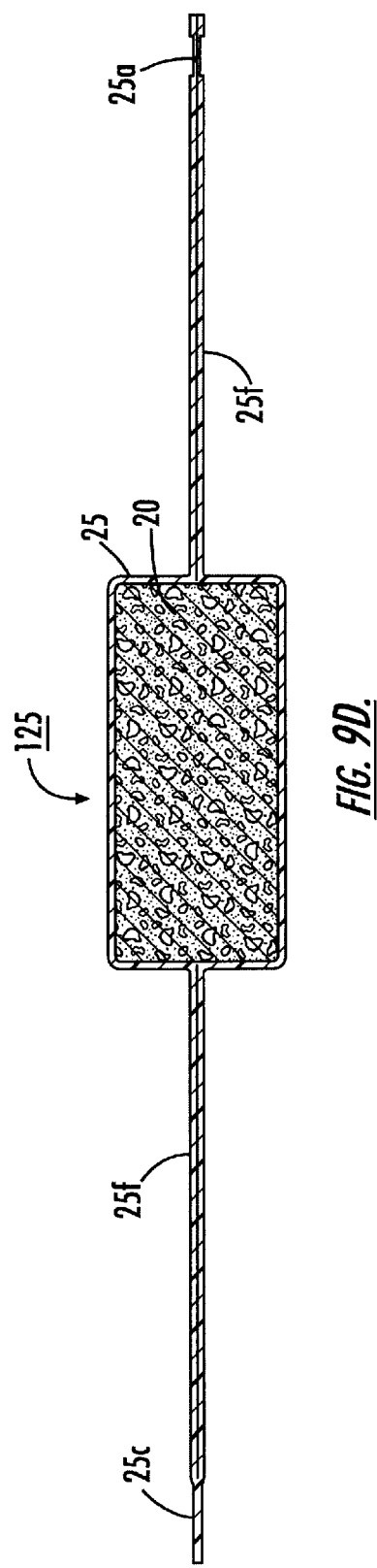
FIG. 9D is a side section view of the specimen and bag shown in FIG. 9B, illustrating the bag sealed such that the bag is collapsed to conform to the exterior of the specimen.
Figure 18:
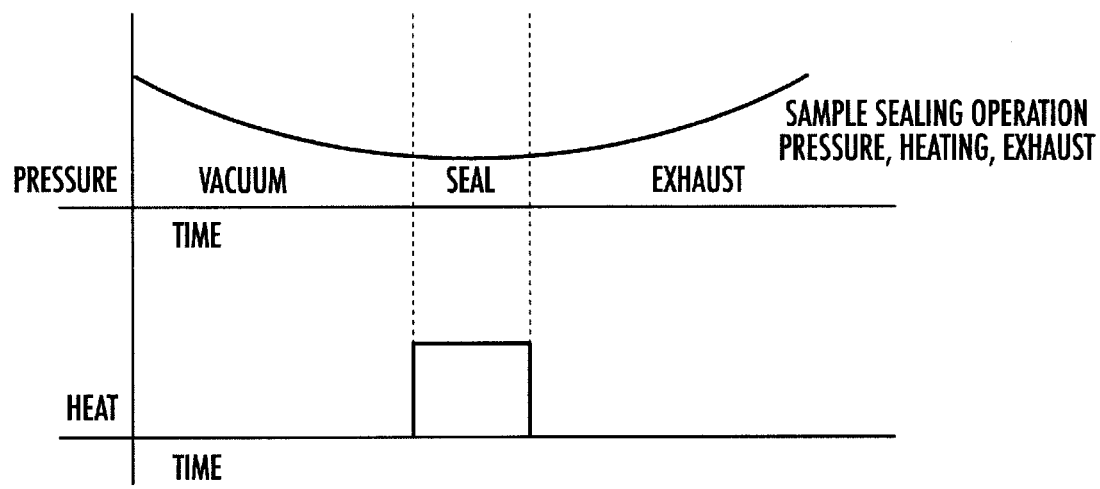
FIG. 18 is a timing chart of an apparatus with an integrated pressure and heating element control according to one embodiment of the present invention.

FIGS. 9A–9F schematically illustrate the sealing method of the present invention. FIG. 9A illustrates a specimen 20 which will be analyzed in a liquid displacement test. As shown in FIG. 9B, the specimen 20 is inserted into the preformed bag 25 having one opening 25o formed therein. Preferably, as shown, the opening 25o is defined by an non-joined segment or side of overlaying first and second walls 26, 27. As shown in FIG. 9C, the bag 25 is configured to define a fluid (i.e., gas) exit path 100 through the opening 25o responsive to a decrease in pressure. This decrease in pressure can be provided in several ways, such as by positioning a vacuum or pressure source in fluid communication with the fluid exit path 100 or the outside of the bag providing a pressure differential thereacross. When used with the vacuum apparatus 12 of FIG. 1A, the bag is positioned in the chamber 13 such that the opening 25o of the bag extends across the sealing element 36. The vacuum pressure is selected (preferably automatically or semi-automatically as will be discussed further below), the sealing time is indicated (with a vacuum response delay time), the lid 14 is closed, and the vacuum apparatus 12 is activated via on/off switch 33. Once the pressure in the vacuum chamber 13 has reached the desired level, the heating element 36 is activated and the mouth or opening of the bag 25o is sealed. Air is then allowed to enter the chamber 13 at a controlled rate which causes the collapse of the bag against the sealed specimen. FIG. 18 illustrates a preferred pressure timing chart (evacuation, seal, and exhaust) according to the present invention. Preferably the exhaust time is greater than about 30 seconds, and more preferably about 35 seconds.

After the lid 14 is opened or, preferably, during the controlled exhaust introduction, the vacuum chamber is exposed to atmospheric or ambient pressure producing, as shown in FIG. 9D, substantially surface conformal bag-sealed specimen 125. The bag-sealed specimen is easy to handle, puncture resistant, and is configured to inhibit water from affecting the specific gravity measurements for porous samples. In operation, the air pressure forces the bag 25 to conform or press against the exterior contour or surface of the specimen, i.e., collapses the bag against the top and bottom surfaces as well as sides 20a, 20b, 20s. Also as shown, the method of the instant invention also preferably causes portions of the first and second walls 26, 27 to align and collapse to produce flat end portions 25f away from the specimen 20. This repeatable configuration advantageously allows the sealing method to yield a water jacket for a plurality of specimens in a manner which provides a substantially constant water displacement volume irrespective of operator material application (trimming, stretching and the like). It will be appreciated that removing the air (substantially all) from the bag prior to sealing is preferred while simply pressing the material layers 26, 27 together is not preferred.

Figure 9E:
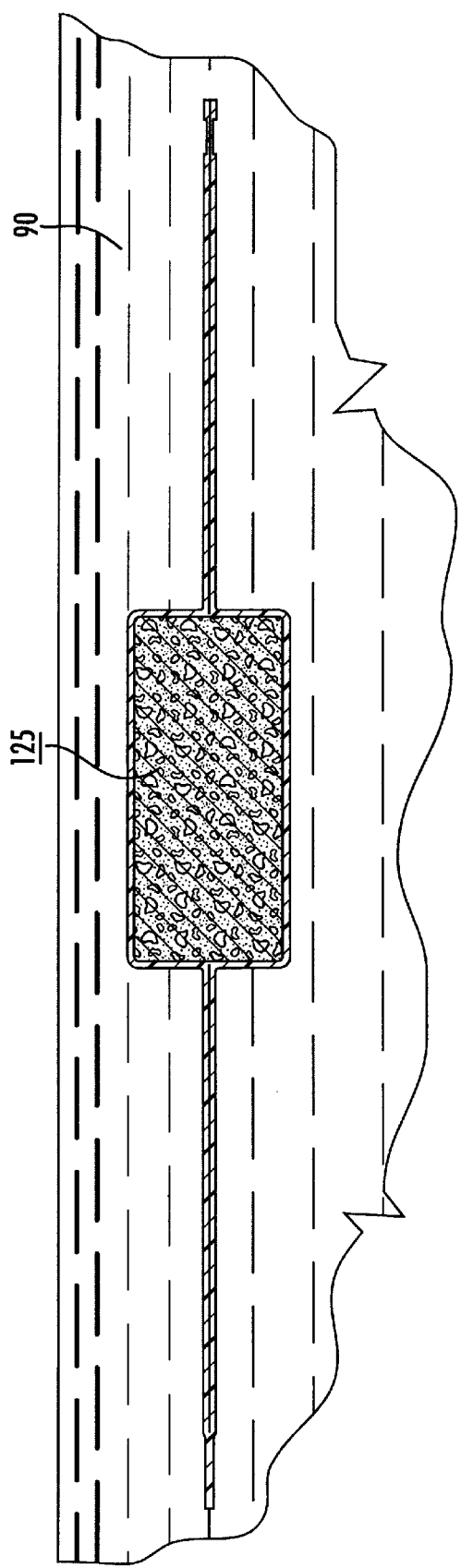
FIG. 9E is a side section view of the sealed specimen of FIG. 9D illustrating its use in a water bath for a water displacement evaluation.
Figure 9F:
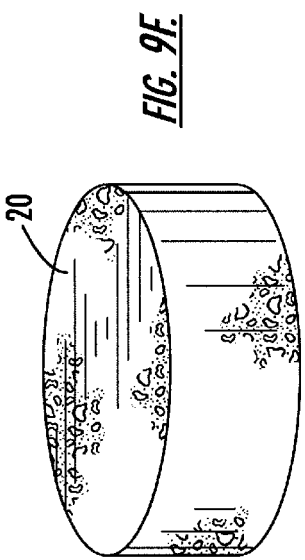
FIG. 9F is a perspective view of a porous specimen subsequent to the water bath step shown in FIG. 9E, illustrating that after removing the specimen from the sealed bag, the specimen's material composition and structure are intact.

FIG. 9E illustrates the sealed specimen 125 is positioned in a water bath 90 for water displacement test evaluation. The bulk specific gravity or density of dense porous specimens by water displacement calculations can now be reliably determined. FIG. 9F illustrates that the specimen remains structurally intact after the bag is removed (simply by destroying the seal and removing the specimen from the bag). Advantageously, this specimen can still undergo additional evaluation.

Preferably, in operation, the vacuum apparatus 10, 10' is preset to operate at predetermined vacuum pressures and times corresponding to the particular specimen type undergoing sealing as well as the type of bag being used therewith. For example, the apparatus 10, 10' can be configured to receive operator input information regarding one or more of the size, configuration, density, and material composition of the specimen as well as the type of preformed bag (usually a product identification number will suffice as it will define the material type, dimensions, standard density correction factor, etc). Typically, the specimens 20 evaluated or processed in a laboratory are presented in one of several standard configurations and material mixtures; allowing advance pressure operational parameters to be predetermined and pre-programmed for automatic operation at the laboratory site. It is expected that a standard vacuum setting will be acceptable for use in the methods of the present invention across a wide range of material specimens including specimens with different thicknesses and textures. The vacuum setting may need to be periodically adjusted for optimum performance so as to account for equipment drift such as may occur over time with the age and use of the vacuum pump.

Preferred vacuum pressures used to conform the bag 20 to the specimen's exterior surface contour can depend on the particular specimen 20. However, it has been found that a single vacuum pressure and/or controlled exhaust rate can be suitable for a number of specimen types and sizes for a particular bag. One preferred bag is a polymer material (preferably a polyolefin) produced by a metallocene catalyzed reaction. In another preferred embodiment, the bag material is formed of polyethylene which includes at least about 20% nylon (this polyethylene/nylon combination is known in certain circles as "polynylon"). Dimensionally, for relatively large specimens, preferred embodiments configure the wall thickness at about a 6.0 mil thickness and a bag width×length of about 16×16 inches or 10×16 inches. A preferred vacuum setting is a vacuum which is above about 20 in Hg, and more preferably, at or above 25 in Hg, and, even more preferably at or above 28 in Hg. Also preferably, the exhaust time (the time it takes to reach atmospheric conditions) is set at about at least 30 seconds, and more preferably, at least about 35 seconds. These parameters have been confirmed as being suitable for compacted material specimens from the construction field, i.e., coarse, porous 6-inch diameter compacted bituminous cores. Indeed, this vacuum pressure is believed to be suitable for across many bag materials. The preferred vacuum calibration method can adjust the vacuum pressure and/or exhaust rate used to seal the compacted specimen 20 corresponding to one or more of the density of the bag (which can vary depending on the material type, thickness, and bag dimensions) and the type of material specimen 20 placed in the preformed bag. The vacuum pressure and evacuation, exhaust times may also vary depending on the material composition and thickness of the walls or number of layers and/or bags used to form the walls of the bag.

Figure 17:
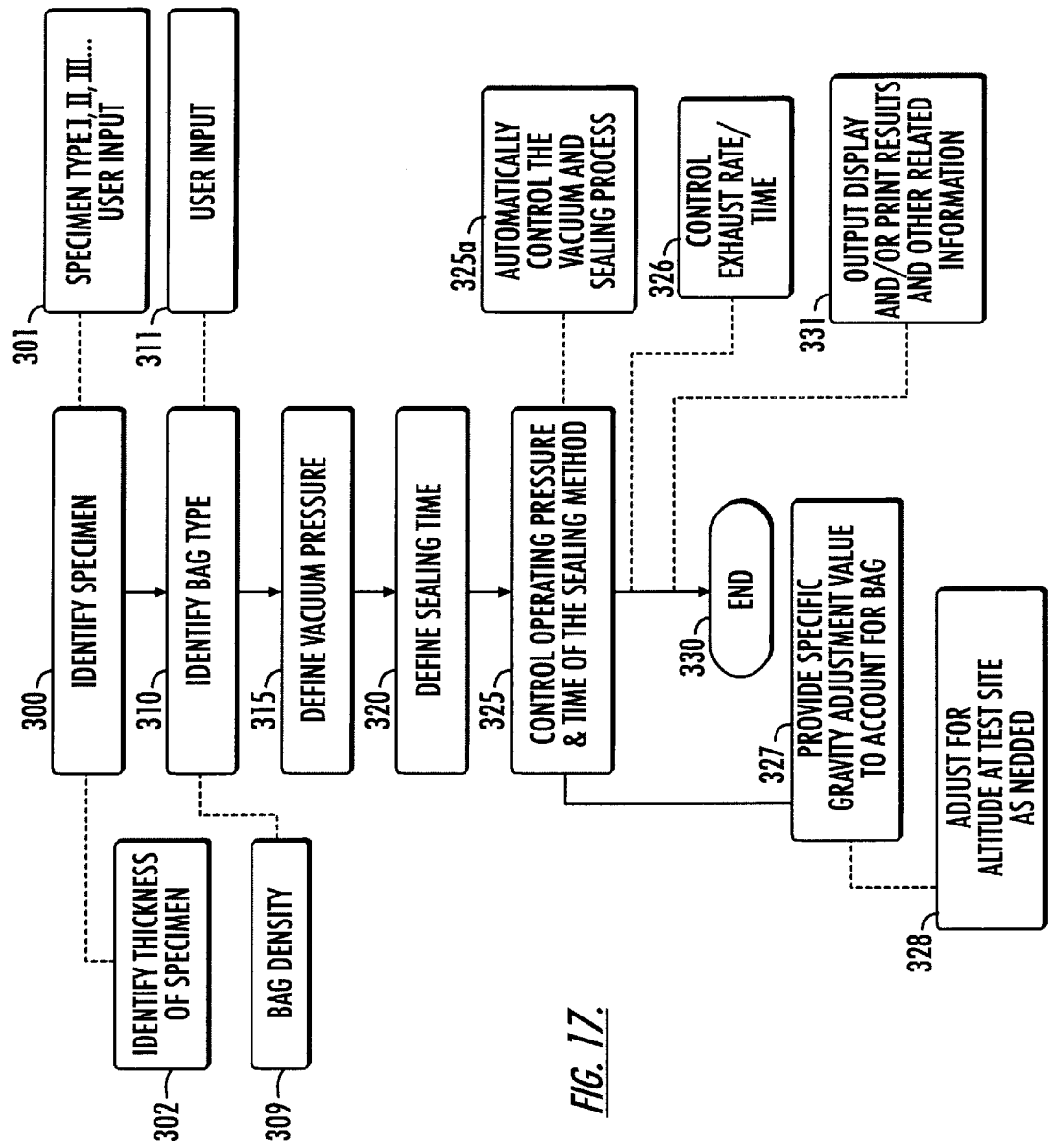
FIG. 17 is a flow chart of a method for sealing a material specimen which can reduce operator-induced variation on the sealed configuration according to the present invention.

FIG. 17 illustrates a flow chart of methods, apparatus (systems) and computer program products according to the invention. It will be understood that each block of the flowchart illustration, and combinations of blocks in the flowchart illustrations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks.

Accordingly, blocks of the flowchart illustrations support combinations of means for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

Figure 19:
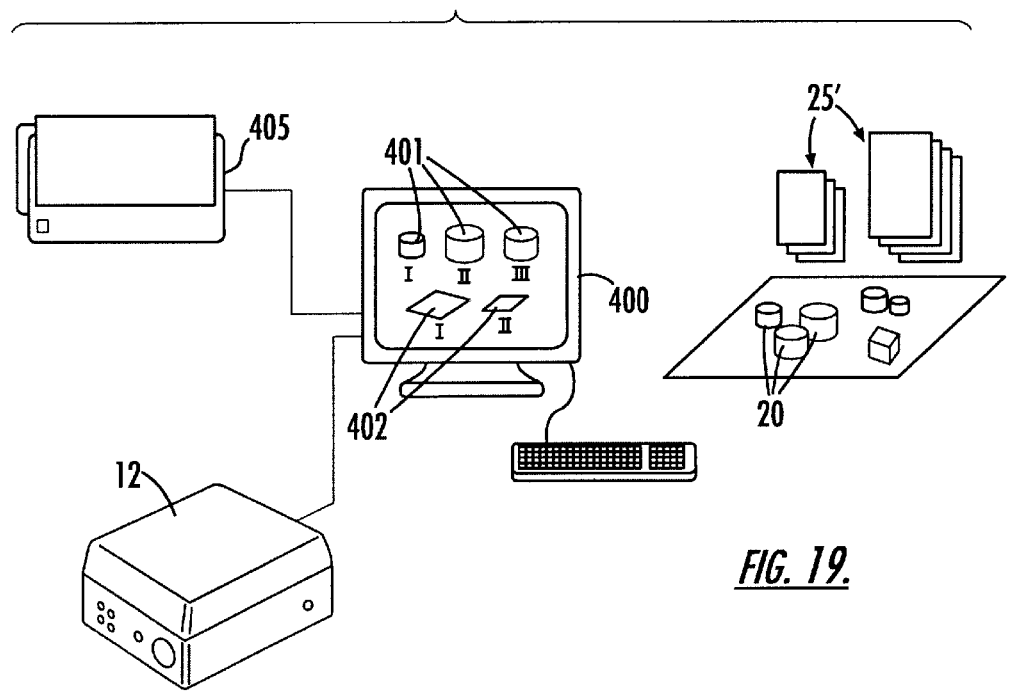
FIG. 19 is a schematic diagram illustrating a machine-controlled embodiment of a sealing system according to the present invention.

As shown in FIG. 17, the operator identifies the specimen undergoing evaluation and classifies it via predetermined criteria (Block 300). For example, the specimen can be classified by one or more of its surface roughness, size (width and/or thickness), configuration, material composition, or approximate composite or bulk density. Preferably, the vacuum apparatus 12 is preferably operably associated with a computer control input (FIG. 19) which controls the operational vacuum of the vacuum pump 12a as well as the exhaust rate. Further, the computer has computer program code means which is configured to accept a user's input to let an operator select the specimen type having those identified criteria, i.e., specimen type I, II, III etc. (Block 301). Optionally, as shown in FIG. 19, a computer 400 operably associated with a vacuum apparatus 12 can be configured to display computer generated icons or digital pictures representing specimen types 401 in a manner which allows a user to easily select the specimen type 401 being sealed according to the present invention. Block 302 further illustrates that a user may input the thickness of the specimen independent of the core size (typically standardized cores with a 4 inch or 6 inch diameter in the construction industry). In any event, the operator selects the specimen type corresponding to the identified criteria. As is also shown in FIG. 19, the system or method preferably includes a printer 405 which automatically calculates the measurement results for the operator.

The operator can also identify the type of bag being used (Block 310). For example, the operator can identify or classify the preformed bag type according to predetermined evaluation criteria or product identification number which is associated with information such as one or more of its density (Block 309) size (dimensions, thickness), material, reinforcement patch configuration, air channels, or bag configuration. Alternatively, an operator can merely enter the product identification number which the computer program can associate with established manufacturing standards, i.e., bag type I, II, III or select it via a visual display of bag types 402 shown in FIG. 19. In any event as for the specimen identification, the method preferably allows user input of the bag type being used (Block 311). Because the preferred vacuum pressures and times are identified and pre-programmed corresponding to certain criteria such as one or more of the specimen thickness or type, or bag type or configuration, the computer program product can then proceed to calculate the optimum vacuum pressures and times for the particular procedure (Block 315). Indeed, in a preferred embodiment the operational pressures and times are automatically directed to the vacuum apparatus to automatically control the operational parameters of the apparatus, thereby minimizing the chance for operator error or variability.

Preferably, the method and/or computer program product is also configured to preset sealing or heating times to (semi) or automatically control the sealing step at the appropriate point and for the appropriate time during the pressure application and for a particular bag type thereby providing repeatability and consistency to the evaluation process (Block 325). It is also preferred (for chamber type vacuum systems such as shown in FIGS. 1A, 1B) that the method control the exhaust rate and/or time of the air (the entry of air back into the chamber) (Block 326). That is, for a particular type specimen 20 and bag 25, the method and automatic (or semi-automatic) operational control provides a sealed specimen 125 which will have substantially the same shape over a plurality of sealed specimens. The method then preferably provides the appropriate reference adjustment for the specific gravity determination (such as a calculated or measured bag density value) to offset the effect of the bag on the measurement (Block 327). Preferably, the method can adjust the bag reference adjustment value according to altitude variations which may be present at the test site (Block 328). Accordingly, the methods and bags of the instant invention thereby displace a constant water or liquid volume in the liquid displacement test to correspond with a known specific gravity adjustment value to minimize test variation attributed to the use of the bag to seal the specimen. Preferably, the test results are then output such as to a display monitor, or printer. The test results can include the test information for the specimen such as the specific gravity, porosity, density, sample type, bag type, date of test, and other pertinent information.

Figure 20:
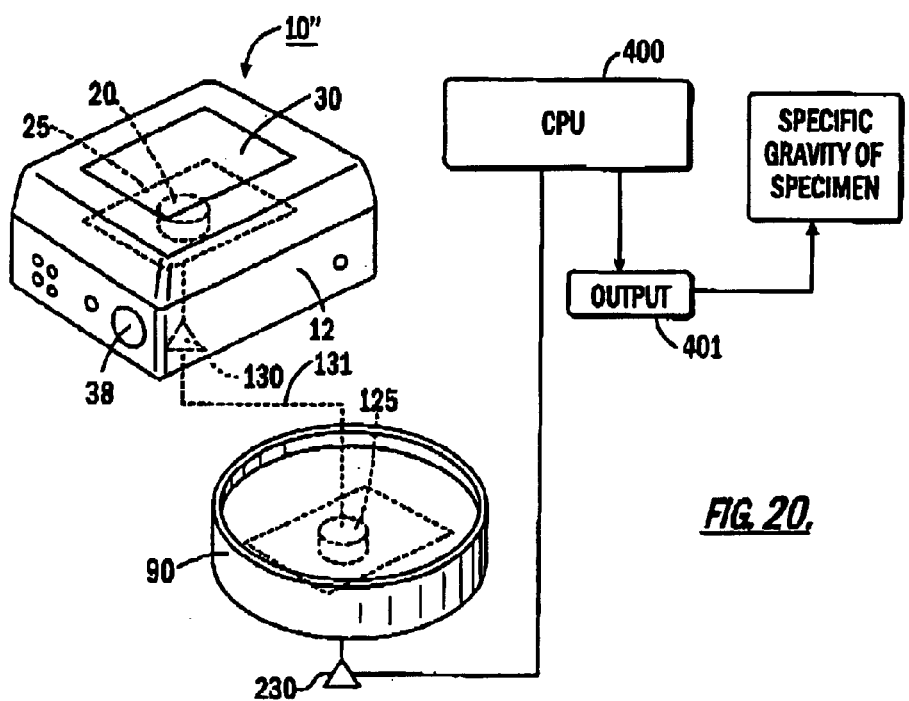
FIG. 20 is a schematic diagram of an additional embodiment of the present invention illustrating an integrated scale apparatus and feedback system configured to provide measurement data to a central processor unit to semi-automatically calculate the specific gravity of a material specimen.

FIG. 20 illustrates a preferred controlled substantially automatic measurement system according to another embodiment of the present invention. As discussed above, the vacuum system 10" preferably includes a scale 130 integrated into the interior of the chamber 13 to measure the weight in air (once the exhaust process has been completed such that the chamber is at ambient atmospheric conditions). This measurement is then relayed to a CPU such as a computer 400 which includes this value in the density calculations as discussed above. As also shown, it is also preferred that the water bath be operably associated with a scale 230 which is connected to the CPU 400. The direct input of this measurement can further automate the test procedure and reduce clerical errors. In one preferred embodiment, the scale 130 can be structurally associated with the water bath to provide a unitary scale used for both the vacuum measurement and the water bath measurement (indicated by dotted line 131). For example, a platform can be suspended from the scale into the water bath, the platform being configured to receive the sample and thus, automatically provide the measurement weight for this step into the CPU (not shown). As shown, the CPU can process the measurement data and calculate and output (401) the specific gravity or density of the specimen The output can be a printer, a display, and even an electronic message reporting the test result based on a coded serial number to a customer's desktop (providing faster test results).

In order to determine the adjustment factor for the bag, a test reference standard, such as a conventional aluminum calibration cylinder, can be used. Other methods for determining encasing sealant or bag apparent densities are discussed further below. For the conventional procedure, as is known to those of skill in the art, the specific gravity adjustment factor for the preformed bag 25 can be provided by determining the difference in liquid displacement for the aluminum cylinder alone and the aluminum cylinder sealed according to the present invention. The difference in the volume of water displaced is the volume attributed to the bag 25. Knowledge of the volume and weight of the porous specimen thus allows for calculation of the specific gravity of the porous sample. The initially determined displaced volume of the bag alone therefore provides a reliable adjustment factor to be applied to calculations used to determine the specific gravity of a plurality of specimens sealed according to the instant invention.

More particularly described, the specific gravity of the cylindrical aluminum calibration standard ($G_{al}$) at a predetermined temperature (25° C.+/−1° C.) is determined by first determining the mass in air and under water. The specific gravity is represented by the equation:

$$G_{al} = A_{al}/(A_{al} - B_{al}),$$

where $A_{al}$ is the dry mass of the aluminum cylinder in air (grams), and $B_{al}$ is the mass of aluminum under water (grams).

Next, the aluminum cylinder is dried and sealed in a preformed bag 25 as described herein. The volume of additional water displaced is determined. Of course, this process can be performed by sealing the aluminum in the bag, measuring the submerged weight of the aluminum and bag, and then removing the bag to submerge the aluminum alone to obtain the submerged weight attributed to the aluminum alone. In any event, during subsequent analysis, this established correction value (amount) is subtracted off the volume of each sealed specimen using similar preformed bag configurations or types leaving the water displacement value for the specimen alone.

Alternatively, the dry sealed mass of the cylinder and mass of the sealed cylinder under water is determined. The "apparent" specific gravity of the preformed bag 25 is determined at the 25° C. temperature by the equation:

$$\frac{D_{al} - A_{al}}{\left[D_{al} - E_{al} - \left(\frac{A_{al}}{G_{al}}\right)\right]}$$

where $D_{al}$ is the dry mass of the sealed specimen in grams, and $E_{al}$ is the mass of the sealed specimen under water in grams. The bulk specific gravity of the sealed specimen 125 of the instant invention can then be determined by the equation:

$$\frac{A}{\left(D - E - \left(\frac{D-A}{F}\right)\right)}$$

where A is the weight of the dry specimen in air (grams), D is the weight of the dry, sealed specimen (grams), E is the weight of the sealed specimen under water (grams) and F is the "apparent" specific gravity of the preformed bag determined at 25° C. Thus, the density of the specimen can be calculated as the bulk specific gravity value multiplied by the density of water (γ) (or other liquid used) at 25° C.

In an alternate embodiment, the actual density of the bag can be determined by measuring the bag's width, length and thickness to establish a bag volume and by obtaining the weight of the bag (such as via a scale) and then mathematically computing the bag density.

The present invention recognizes that correct and accurate determination of the bag density value can be particularly important in obtaining reliable measurements, as the value is used in the calculation of the material density evaluated according to the sealed bag liquid displacement methods of the present invention. The conventional method, described in ASTM D1188 and also described above, uses a single known reference standard (typically made from a cylindrical shape solid core of aluminum) to calculate the density of the sealing material. As noted above, the density of the reference standard can be obtained by water displacement, and, thus, the density of the sealing material (or bag) can also be derived once the reference and the sealing material are water displaced together.

However, using only one reference sample may not accurately provide a "true" apparent density value. For example, if the reference has a geometry, shape, or size which is different from the specimen undergoing analysis, the apparent density value obtained with the former may not be accurately representative of the latter. Thus, the differences between the two can undesirably effect the liquid displacement-based sample density results used to calculate the sealant or bag density. While the use of one reference standard may be sufficient if the sealant or bag conforms substantially the same for all different material samples, this is most likely not the case where there is a wide variation in sample shapes, sizes, or geometry. Thus, it is preferred that the reference standard used to calculate the density of the sealing material be selected so that it is similar in geometry and/or size to the sample to be tested or analyzed.

Further, particularly for specimens prepared with vacuum sealing procedures, it is also preferred to configure reference samples with residual voids (i.e., with surface dimples or indentations versus a solid/smooth peripheral surface) to allow the sealing material or bag to conform tightly around the reference sample for use in the determination of the sealant or bag density. That is, asphalt samples or specimens obtained from the field, as well as laboratory prepared samples, can have different sizes. Typically, these samples are generally cylindrical in shape, although they may have different diameters and thickness. Square or other shaped samples with different dimensions can also be analyzed for density from time to time. Asphalt samples are designed to have a desired level of voids. The voids can help with appropriate drainage and allow for movement of liquid asphalt and aggregates during field compaction and while exposed to traffic. The residual voids in the sample also can help the bag substantially collapse against and conform to the sample's profile during the vacuum sealing process described herein. Unfortunately, employing a single solid continuous outer surface reference sample (representing only one cylinder shape with one diameter and/or thickness or length) as described above to establish an apparent bag density can be problematic, as it may not be representative of the various geometrical conditions/shapes of the asphalt samples and can, thus, negatively impact the density determination of the specimen.

Therefore, a preferred method for determining the apparent bag density is to use a standard or reference sample which closely resembles the specimen that is to be tested or analyzed. Further, for vacuum sealing encasing procedures, it is preferred that a reference sample configured with residual voids thereon, which may or may not be interconnected, be used to establish the apparent density value of the sealant (allowing the sealant material to collapse and snugly adhere against the reference sample and, thus, behave more like an actual field or laboratory specimen).

As used herein, the term "apparent bag density" is the density of the bag as determined by water displacement methods using a known or standardized reference sample. The term "residual voids" represents the amount of air voids configured into the reference sample or test sample. The term "reference sample" indicates a sample that can be used as a reference for determining the apparent density of an encasing sealant or bag material. The reference sample must be able to undergo water displacement evaluations without absorbing water, or, alternatively, its volume measurement must be able to be established by other conventional means as is well known to those of skill in the art (such as by calculating volume based on dimensions).

Thus, the present invention preferably determines the apparent density of the encasing sealant or bag by using a value which is established corresponding to a standard that resembles, or is similar to, the sample, and more preferably relatively closely resembles both the shape and thickness of the sample that is to be analyzed or tested. As noted above, for vacuum sealed compacted specimen analysis, it is further preferred that the reference sample also be configured with residual voids to emulate voids present in the test sample and/or to allow the encasing sealant or bag material to adhere tightly around the reference sample as it is processed as described herein. It is noted that, although a sealable bag is preferably used, the improved methods and test reference samples of the present invention for providing apparent density determinations are not limited thereto. Thus, the term "encasing sealant" preferably means conformable or elastomeric sealable bags but can also include other sealant materials which are configured to encase the material specimen undergoing analysis.

Generally described, the first step in determining the sealant or bag apparent density is to select a known reference standard sample or to water-displace a reference sample and then calculate the density thereof as generally described above. A predetermined set of apparent density values can then be established across an assortment of varying reference samples representing typical specimen geometries, thickness, and diameters. For sealants or bags used to analyze asphalt specimens, a similar set of apparent density values can be established across an assortment of voids, geometries, and sizes. In addition, the present invention can also provide a range of apparent density values for even loose specimen mixtures (the latter will be discussed further below). In any event, the assortment of established apparent density values can be used to define a range of apparent density values that can be provided electronically as a computer readable program with input data or a computer readable "look-up" chart, or an equation, or as laboratory provided or determined "plug-in" numbers for an operator to easily determine the appropriate density for use in conjunction with the specimen undergoing analysis.

Preferably, the assortment of apparent density values is established at a manufacturing site and supplied for use at the testing facility. The operator at the testing facility need only weigh the bag to determine that it is within predetermined limits. For example, for each shipment lot or even for each approved bag design for a particular supplier (a defined material, thickness, size, and controlled production process), an assortment of values can be established. An operator at the testing site need only weigh the bag to affirm that it is within tolerance, such as that the bag weighs within about +/−1.0 gram from a defined weight. Once confirmed, the operator can rely on the predetermined set of apparent density values (or discard the bag if outside the tolerance range), look up the value for the reference standard resembling the actual specimen (or input the specimen type into the computer), and receive an apparent density value corresponding to the specimen. Similarly, for non-bag sealants, a range of apparent density values can be established for a particular approved supplier or by inspection of each shipment/production lot, and those values can be provided in computer readable format.

In any event, to establish a suitable range of apparent density values, a plurality of reference samples of known density are employed or the density for each is calculated or determined for the selected reference standards. The plurality of reference samples are selected such that they are representative of field—or laboratory—prepared specimens so as to have geometries similar to the specimens to be analyzed.

Once the density of the reference sample(s) is calculated, the apparent bag or sealant density can be determined (of course, the second value can be established first). To calculate the apparent density value of the sealant, or preferably the bag for a particular specimen geometry, the representative reference sample is encased in the sealant, or more preferably, vacuum-sealed within the bag as described herein. The encased sealed reference sample is water-displaced again, and the sealant or bag apparent density can be calculated based on the density value of the reference standard. That is, based on the density calculated for the reference standard with and without the sealant, the bag or sealant apparent bag density can be determined by the mathematical equations given for calculation of the apparent density using a single reference standard.

In one embodiment, a plurality of solid reference samples, each of which has a continuous outer surface, are used to determine an associated range of apparent density values. Preferably, as noted above, an assortment of solid reference standards, each having a different size and geometry representative of typical specimens, are used. For example, for analyzing 4.0 inch diameter asphalt specimens, a plurality of solid (continuous outer surface) aluminum cylinders of 4.0 inch diameter are obtained with the thickness ranging from about 1.0 inches to about 5.0 inches. Then, for each aluminum reference sample, the apparent bag density is calculated. The laboratory operator, when testing a 4.0 inch material specimen, determines the thickness of the specimen and then selects the apparent bag density provided for the reference standard thickness corresponding to the specimen. Table I below provides typical apparent density values for a 4.0 inch diameter reference at different thickness.

TABLE I

| 4.0 inch Aluminum Cylinder Thickness (inches) | Apparent Density (g/cm$^3$) |
|---|---|
| 1.0 | 0.820 |
| 1.5 | 0.760 |
| 3.0 | 0.658 |
| 4.0 | 0.644 |
| 5.0 | 0.625 |

As noted above, to calculate specimen density, the operator can select the appropriate apparent density value corresponding to the thickness of the specimen. A similar table (such as via a computer readable program or operator calculable based equation) can be established for other configurations, such as for a 6.0 inch diameter cylinder or other shape samples.

Figure 8:
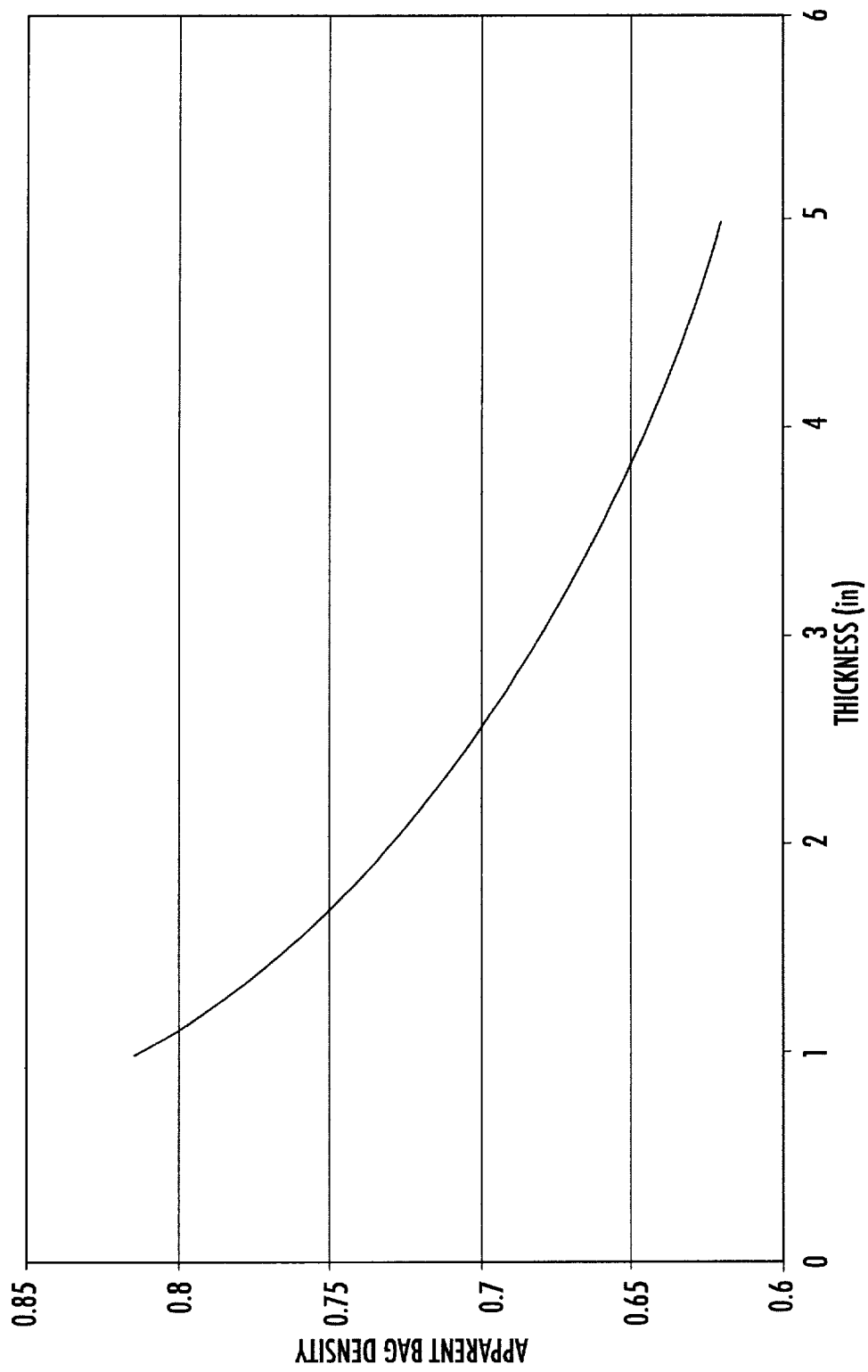
FIG. 8 is a graph of apparent bag density versus thickness of a 4-inch diameter cylindrical material reference standard sample. In operation, a suitable apparent density value of a preformed bag or sealant used to encase the material specimen is chosen based on the apparent density value corresponding to the reference sample size (and shape) similar to the material specimen undergoing evaluation according to the present invention.

Alternatively, a mathematical relationship can be used to establish the apparent bag density based on an input characterization of thickness (and shape, size and the like). Thus, for a 4.0 inch diameter cylindrical specimen, the operator can input the thickness value and then receive a number representative of the sample. For example, the mathematical relationship can be exponential over a wide range of thickness (such as between 0.5–6.0 inches) as shown in FIG. 8, or linear between a smaller thickness range (such as a 2–3 inch range). Thus, one or more equations can be established and used to calculate the apparent bag density value for the specimen undergoing analysis. For example, for a wide thickness range such as for thickness range of between 1–6 inches, the equation, AD=E exp (−FX), can be used, where "AD" is the apparent density, "X" is the sample thickness, and "E" and "F" are constants derived by computational methods during calibration by using different thickness reference samples. For smaller thickness ranges, such as between about 1–3 inches, a linear equation can be suitable. For example, the equation AD=A+BX can be used for calculation of apparent density ("AD"), where "A" is the intercept and "B" is the slope of the line. Thus, one exponential equation can be provided for a wide thickness range, or two or more linear equations can be provided for smaller ranges. In another alternative embodiment, one or more "average" or "mean" apparent density values can be established across one or more thickness ranges for a particular geometry and that value used for all specimens corresponding to that geometry and thickness range.

In any event, the calculation of apparent density as explained above as well as the geometry-selected value appropriate for the specimen undergoing evaluation can be accomplished by manual means or by computer-readable means, whether the computer is embedded in the system or vacuum equipment or in a stand-alone laptop or other external computer.

In another apparent density determination embodiment (which is particularly suitable for asphalt samples), the present invention employs reference samples which are configured with air voids. As is known to those of skill in the art, asphalt specimens are configured or generally designed to contain about 4% air voids. When vacuum-sealing asphalt samples, the sealant or bag conforms tightly around the sample (collapses against the sample). This can be at least partly attributed to the fact that any air remaining proximate the sample in the bag after evacuation can escape or enter the sample or specimen voids. In contrast, in the case where there are no voids in the sample, air can affect how tightly the bag conforms to the sample. Therefore, it is preferred that, in order to more representatively simulate the condition of the sealed asphalt samples, reference samples having known amounts of voids, which may or may not be interconnected, are used.

One example of a suitable reference sample 200 which is configured with air voids 200$v$ is shown in FIG. 26. In this embodiment, an aluminum cylinder of known diameter and thickness with air voids 200$v$ can be formed by drilling holes (or dimples) into the exterior surface of the reference cylinder. For density determinations in water displacement tests, it is preferred that the air voids be positioned on one surface (this will become the upper surface when oriented in the liquid bath) so that the air voids can retain water during the liquid displacement tests and, thus, accurately account for absorbed water in the reference sample. Liquid displacement tests with and without the sealant or bag as described above allow for calculation of apparent bag density. Of course, the air voids 200$v$ can be introduced onto more than one surface if the density is determined by other conventional means, such as by calculating the volume of the sample by calculating the dimensions of the solid cylinder.

Preferably, the dimples or voids 200$v$ are formed into the outer surface of the reference sample 200 at a depth which is sufficient to simulate an air void while also being not overly wide so as to inhibit the sealant or bag 25 from being distorted by the bag wall being pulled into cavities created by unduly wide or large air voids during evacuation. More preferably, the voids 200$v$ or dimples are formed (i.e., drilled or cast) into the cylinder with a diameter of about ⅛ inch (3.2 mm) or less. Thus, to provide an air void content which is much above about 3.2%, the dimples or voids 200$v$ may need to be introduced onto more than one surface. It is also preferred that any sharp or rough edges associated with the voids be filed or formed with a radius to inhibit punctures during evacuation or handling. Although the void pattern shown in FIG. 26 is generally symmetrical and non-interconnecting, the present invention is not limited thereto as other patterns can also be used to simulate air void content. Table H below illustrates typical apparent bag density values for 6.0 inch diameter aluminum cylinder specimens having a thickness in the range of between 1–5 inches with differing amounts of air voids (0.5–3.2%) formed thereon. As for the embodiment described above, similar data can be developed for other specimen geometry and/or diameter cylinders such as for a 4.0-inch diameter cylinder.

TABLE II

| 6.0 inch Aluminum Cylinder Thickness (inches) | % Air Voids | Apparent Density (g/cm$^3$) |
| --- | --- | --- |
| 1.0 | 1.5 | 0.798 |
| 1.5 | 2.3 | 0.867 |
| 4.5 | 3.2 | 0.474 |
| 5.0 | 0.5 | 0.676 |
| 5.0 | 0.8 | 0.703 |
| 5.0 | 1.2 | 0.736 |
| 5.0 | 1.9 | 0.807 |

For calculation of the specimen density, the appropriate apparent density value can be selected from the table based on the parameters most resembling the specimen thickness and the specimen air void content (the air void content of the asphalt specimen undergoing analysis is typically designed into the asphalt composition or predetermined by the site/application). As before, a mathematical relationship can also be established to represent the value of the apparent bag density based on an input of specimen thickness and air void content. As also discussed for the embodiment above, an average or mean value can be established across all typical thickness and air void content.

In yet another embodiment, the apparent bag or sealant density can be determined based on an asphalt reference sample of known density and air void content. For example, an asphalt reference sample 200' can be prepared as shown in FIG. 27, and encapsulated or vacuum-sealed in a bag as described above. Once the asphalt reference sample 200' is sealed, the density of the reference sample and the bag can be determined by water displacement as described above. The density of the reference sample 200' can be calculated by other conventional means, such as by measuring the dimensions of the reference sample to calculate a volume and obtaining the weight of the sample to provide a mass or by a water displacement method if the sample is designed as a close composition (dense graded) non-absorbent mixture. The density can be determined by taking the ratio of the mass over volume. Thus, using the density obtained by the conventional means and the vacuum-sealed density, the bag apparent density can be calculated. This apparent bag density can be used to measure the density of unknown asphalt specimens using the encasing or vacuum-sealed preparation methods of the instant invention. As before, one or more reference samples can be used as needed, depending on one or more of the particular application, asphalt mixture design, asphalt mixture specimen thickness, void structure, and other known relevant design parameters.

Figure 28:
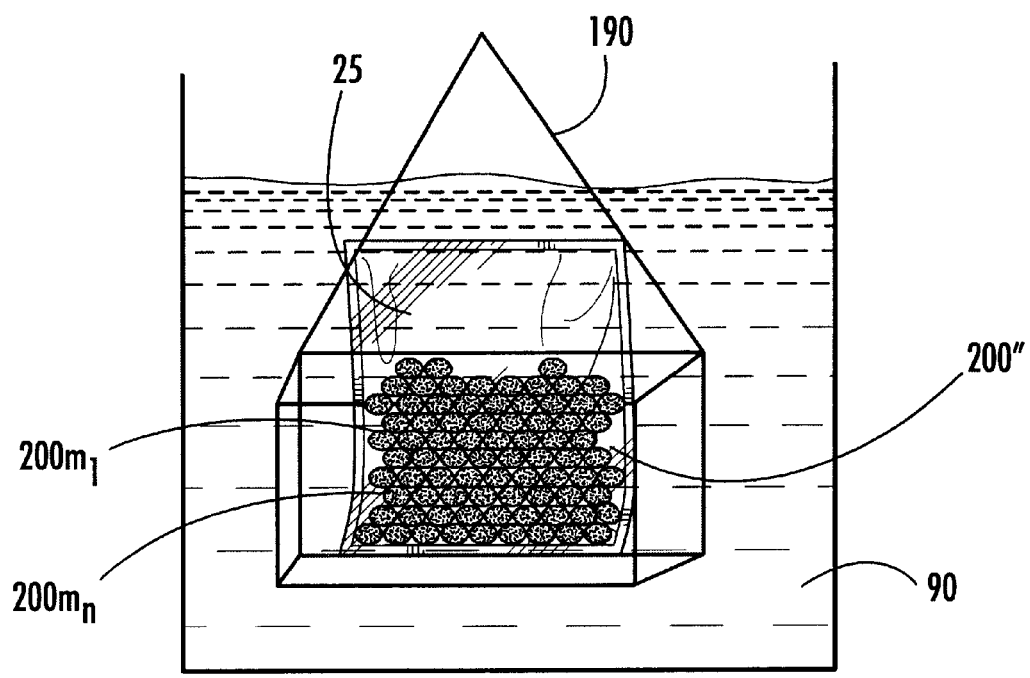
FIG. 28 is a schematic illustration of a reference standard comprising loose articles according to the present invention.

For loose mixture specimens, the present invention provides a reference sample 200" configuration as shown in FIG. 28, which is representative of loose mixtures and which can provide improved apparent bag density values for same. This apparent density determination method is particularly suitable for loose mixture specimens which are sealed in a sealant or bag which is subsequently opened to allow water to enter therein once the bag with the sample is immersed in a liquid displacement bath (as will be discussed later in the application). As will be discussed more particularly below, during measurement of maximum specific gravity or permeability, the bag with the loose specimen is vacuum-sealed, immersed in the liquid displacement bath, and then opened to allow water to enter therein. Since water fills the bag in this process, the contribution of the bag to the displaced volume in the tank can be different from the bag that is completely sealed around the sample and held therein with its seal integrity uncompromised. Therefore, it is preferred that an apparent bag density be determined using the open bag condition under water.

In order to determine the apparent bag density using the open bag condition under water (or liquid), a plurality of loose articles $200m_1$–$200m_n$ are used as the reference sample 200" to simulate the loose specimen. It is preferred that the loose articles are non-absorbent and configured with smooth contours to inhibit puncturing of the sealant or bag during sealing or handling.

In a preferred embodiment, marbles are used as the loose reference sample 200". In operation, the density of the plurality of marbles is determined by water displacement evaluation methods as described above. The plurality of marbles are then dried and inserted into the bag 25 which is then vacuum sealed as also described above. The sealed bag is immersed in a liquid displacement bath 90 and an opening 226 is introduced into the bag to allow water to enter therein. After the scales stabilize (the weight will fluctuate until the water fills the bag), the weight of the water filled immersed bag holding the loose reference sample 200" is obtained. Based on this weight and the weight obtained in air, the combined density of the bag and marbles can be established. Taking into account the density of the loose marbles calculated above and the combined density of the marbles and the bag opened in the water, the apparent bag density can be determined. Metal objects or other non-absorbent material articles can also be used.

In one embodiment, a sub-container $25_{sub}$ is employed to hold the loose specimen 20 undergoing analysis and the loose marbles or articles 200" as shown in FIGS. 25A–25C and FIGS. 25D–25F in establishing the apparent bag density values. As will be discussed further below, the sub-container $25_{sub}$ is configured to hold the loose specimen 20 within the bag 25 (the bag 25 encases the sub-container $25_{sub}$ which holds the loose specimen mixture 20 therein) and is configured with a series of apertures 225 to allow water to enter therein once the integrity of the bag has been compromised. The density of the sub-container $25_{sub}$ can be calculated by conventional means as described above so that it's contribution to the density of the combined bag, reference sample, and sub-container can be offset therefrom. If a non-absorbent material is used to form the sub-container $25_{sub}$, a liquid displacement test can be used to establish the density. During sealing of loose mixtures, if a sub-container $25_{sub}$ is not used, the pressure induced by the bag 25 conforming to the mixture 20 can cause varying levels of compaction depending on the mixture composition. Excessive compaction of the mixture 20 can cause increased amounts of air voids within the sample 20 which, in turn, can cause higher volume readings and unreliable maximum density results. Advantageously, the sub-container $25_{sub}$ can facilitate more repeatable sealant configurations and test results.

Preferably, for tests opening the sealant or bag in the water, apparent density values are determined in this manner. As above, additional apparent density values can be established for different size articles or marbles or different quantities of marbles or articles according to the aggregate or loose specimen undergoing analysis.

Turning now to preferred vacuum operation, in one preferred embodiment, a relationship is established between the specific gravity of the preformed bag (for bags of different sizes and thickness) and a range of different standard reference block thicknesses for a given vacuum operation time. For example, the apparent specific gravity of the preformed bag 25 is determined for an aluminum reference block specimen having a diameter of 6 inches (150 mm) and thicknesses ranging from about 1–6 inches. A similar relationship can be established for other compacted material specimen sizes or configurations, such as for a 4 inch (100 mm) diameter core.

Preferably, the apparent bag density versus specimen thickness relationship (i.e., the calibration evaluation factor) for a plurality of different specimen configurations is predetermined at a first use point, or more preferably, at the original equipment manufacturer (OEM) which may display different mathematical models depending on the variables involved. Either way, the factory or first use calibration relationship model can eliminate the requirement for the laboratory technician to perform the aluminum standardization bag density test prior to each compacted material specimen 20 measurement. It is also preferred that the elevation of the test site be taken into consideration when establishing the calibration factors because the relationship can be affected by elevation when testing is performed. Further, it is preferred that the vacuum level and exhaust rate be set such that normal variations in elevation does not affect the density measurement. The bag density relationship for a compacted specimen across a range of specimen sizes and shapes can yield a reliable calibration factor which can be applied by a computer look up table or program to automatically adjust the calculation of the specimen density based upon the user input regarding the compacted material specimen 20 configuration under evaluation. Further, it is believed that the vacuum setting and the bag density relationship for a specimen size and thickness will be substantially independent of the type of material used to form the compacted material compositions.

As discussed above, it is preferred that the bag be precision manufactured such that its dimensions and configuration are suitably controlled to minimize the variability in the bulk specific gravity and density determinations. As used herein, the term "high precision" or "precision" manufactured means producing the bags such that for a particular type, they have minimal variation across a statistically representative population. As such, it is preferred that the tolerances used to produce the bag be about at least +/−0.0002 inches in the thickness dimension and +/−0.1 inches in the other dimensions. Stated differently, it is preferred that the tolerances of the material thicknesses for each product type are predictably and reliably reproducible over mass production. It is also preferred that the bags be produced according to six sigma manufacturing standards to reduce process variation particularly in the thickness dimension.

Figure 10:
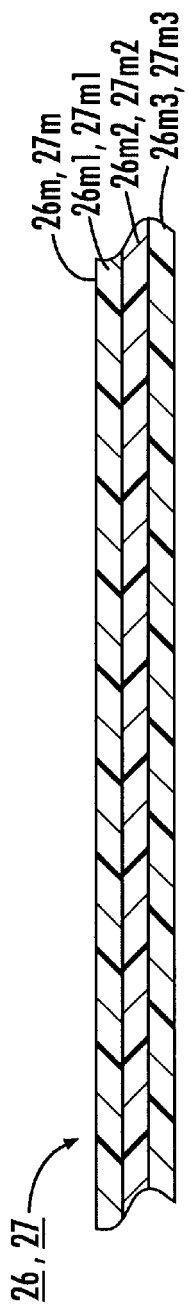
FIGS. 10 and 11 are enlarged partial section views of multi-layer walls for a bag according to the present invention.
Figure 11:
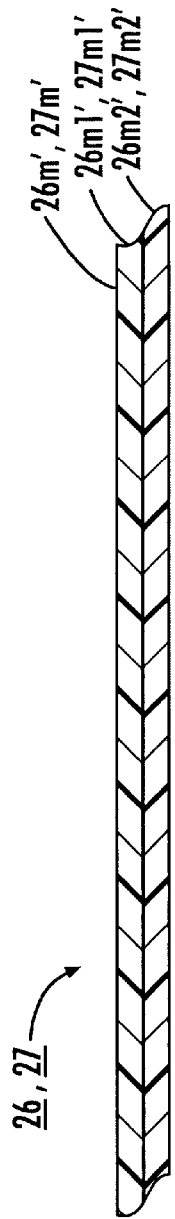
Figure 16A:
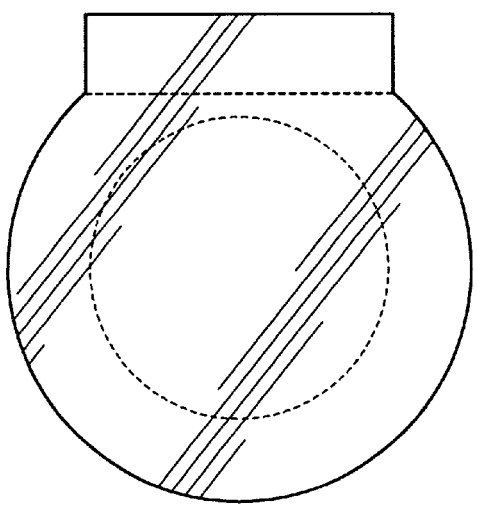
FIGS. 16A–16C are top views illustrating alternative configurations for the preformed bag according to the present invention.
Figure 16B:
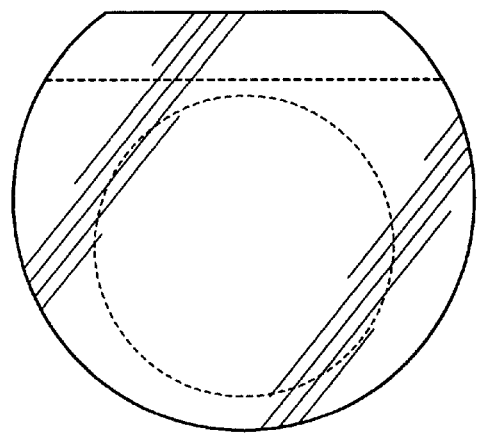
Figure 16C:
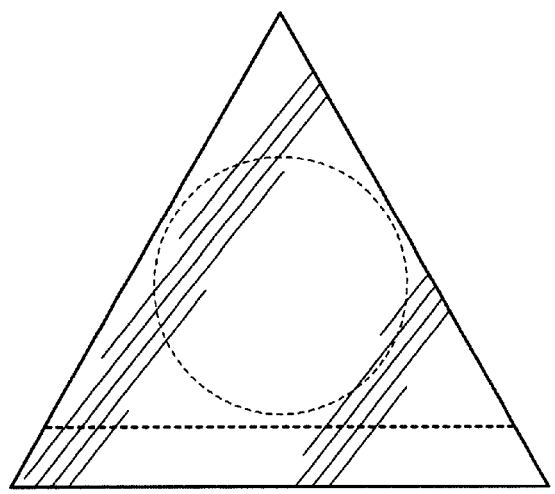

As shown by FIGS. 10 and 11, one or more walls 26, 27 of the bag can be formed of more than one layer of material. FIG. 10 illustrates a three-layer configuration 26m, 27m with three separate layers of material 26m1, 26m2, 26m3, and 27m1, 27m2, 27m3, respectively (the layers can be formed of the same material or materials which are different from each other). FIG. 11 illustrates a dual layer configuration 26m', 27m' with layers 26m1', 26m2', and 27m1', 27m2'. The multi-layer configurations 26m, 26m', 27m, 27m' can be used in lieu of or in addition to the reinforcement patches 45, 49 described above. Although illustrated for clarity throughout as a rectangular shaped bag, the present invention is not limited thereto. Indeed, many additional shapes and configurations can be employed according to the present invention. For example, but not limited thereto, FIGS. 16A, 16B, and 16C illustrate additional shapes or configurations of a preformed bag 225, 225', 225", respectively.

In sealing coarse construction type compacted material specimens 20, the bag selected to seal the specimen is preferably selected to meet two functional parameters. More particularly, the material used for the bag is preferably selected such that it is sufficiently strong and/or durable to be puncture resistant and also sufficiently flexible to conform to the irregular contours of the surface of the coarse specimen when processed as described herein. As discussed above, during the sealing process, the walls of the bag collapse to substantially conform to the exterior of the specimen 20. This easy conformation with the contours of the specimen will provide a predictable repeatable sealed shape which, in turn, allows for a constant water volume displacement and a constant reliable adjustment factor for the specific gravity analysis.

It is also preferred that the bag 25 be configured with respect to the material specimen 20 undergoing evaluation such that width of the bag 25 (i.e., the opening along one side) is about at least twice the diameter or width of the compacted material specimen 20. It is additionally preferred that the maximum width of the bag be less than about three times the diameter or width of the compacted material specimen 20 to reduce excess amounts of sealant (bag) material which can potentially result in measurement inaccuracies attributed to one or more of air bubbles being trapped by the additional material or stretching that can occur during vacuum operation which can result in short term drift in weight measurements during water displacement evaluations.

It is also preferred that the size of the bag be configured such that it closely corresponds to the size of the specimen undergoing evaluation to reduce the amount of excess material employed and thereby reduce the potential for entrapping residual air therein.

Suitable bag materials include, but are not limited to, elastomeric and plastic materials and polymers. For the purposes of the inventions herein, the term "polymer" to be broadly construed to include homopolymers, copolymers, terpolymers and the like. Similarly, the terms "blends and mixtures thereof" include both immiscible and miscible blends and mixtures. Examples of suitable materials include, but are not limited to, polyoelfins (e.g., polyethylenes, polypropylenes), polystyrenes, polymethacrylates, polyvinyls, polydienes, polyesters, polycarbonates, polyamides, polyimides, polynitriles, cellulose, Tyvak® and cellulose derivatives and blends and mixtures thereof. Two preferred bag materials are noted above.

FIG. 21 is a table of measured parameters according to the present invention. The top portion of FIG. 21 provides data associated with two standard aluminum with known densities. The bag densities determined from this portion of the test were averaged for subsequent determination of the density of the asphalt core samples given in the lower portion of the table. The lower portion of the table is a listing of results or calculations and measurements used to determine core density according to the present invention.

FIG. 22 is a sample of a data intake sheet suitable for determining core density of a compacted specimen according to the instant invention. As shown, each column has an "alpha" identifier which in subsequent blocks may be mathematically manipulated with other values to finally provide the core density (identified as "p"-block-or Col. "p" of the bottom table) or bag density (identified as Col. "I", top table). Accordingly, FIG. 22 illustrates a preferred computational method and method steps for determining core densities and/or the bag densities according to the present invention.

The following examples are meant to provide a listing of parameters which can facilitate the sealing method of the present invention. Many of the bag/specimen parameters can be identified and the corresponding operational parameters (vacuum pressure setting, time, etc.) can be automatically input to the sealing system via a relational database to limit the amount of steps which are required to be taken by an operator at the laboratory evaluation site.

EXAMPLE 1

| 4 inch diameter core (fine aggregate composition) | |
|---|---|
| Parameter | Value |
| Specimen thickness | |
| Vacuum pressure setting | |
| Vacuum time | |
| Sealing time | |
| Exhaust time | |
| Bag thickness | |
| Bag material | |
| Overall bag size | |
| Reinforcement type | |
| Bag density correction factor | |
| Material specimen specific gravity estimate | |

EXAMPLE 2

| 4 inch diameter core (coarse aggregate composition) | |
|---|---|
| Parameter | Value |
| Specimen thickness | |
| Vacuum pressure setting | |
| Vacuum time | |
| Sealing time | |
| Exhaust time | |
| Bag thickness | |
| Bag material | |
| Overall bag size | |
| Reinforcement type | |
| Bag density correction factor | |
| Material specimen specific gravity estimate | |

Figure 12:
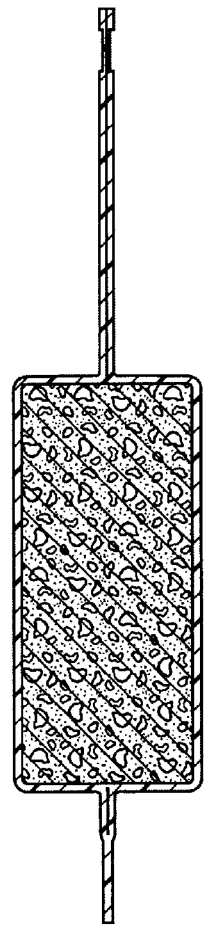
FIG. 12 is a side section view of a porous material specimen having a surface conformal jacket provided by a compressible resilient bag with one end having a longer length from the sealing edge to the specimen compared to the other end according to the present invention.
Figure 13:
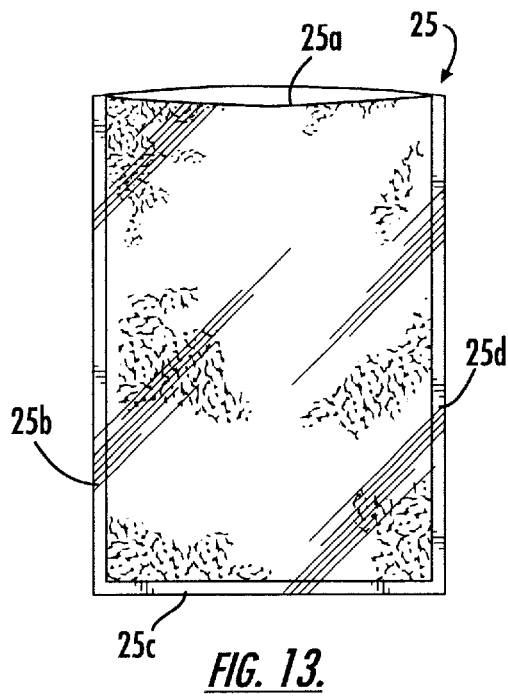
FIG. 13 is a top view illustrating a preformed bag having three pre-sealed edges or sides according to the present invention.

If the sealed specimen 125 (FIG. 12) will be stored prior to water displacement evaluation, especially for extended periods, it is preferred that the material be selected to provide an oxygen resistant barrier to minimize the oxygen migration into the chamber 29 or porous channels of the specimen. Because of the pressure differential, air may migrate across the walls of the bag into the sealed specimen 125 over time. This oxygen-resistant barrier can be provided by one or more of sizing the thickness of the wall of the material sufficiently thick to inhibit the migration of oxygen thereacross, using several layers of material, or using material to form the walls which is resistant to the migration of oxygen therethrough. Examples of oxygen resistant materials include, but are not limited to, metallized bags an/or nylon bags.

Figure 23A:
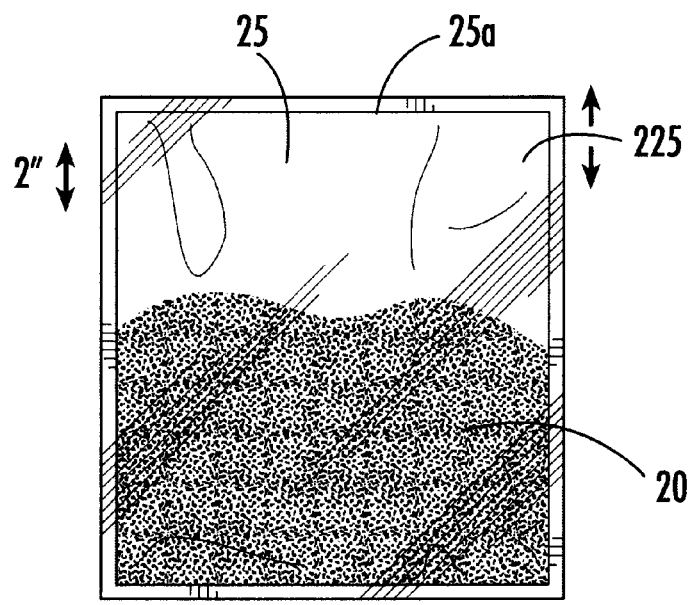
FIG. 23A is a front view of a loose (preferably uncompacted bituminous) material sample sealed in a bag according to the present invention.
Figure 23B:
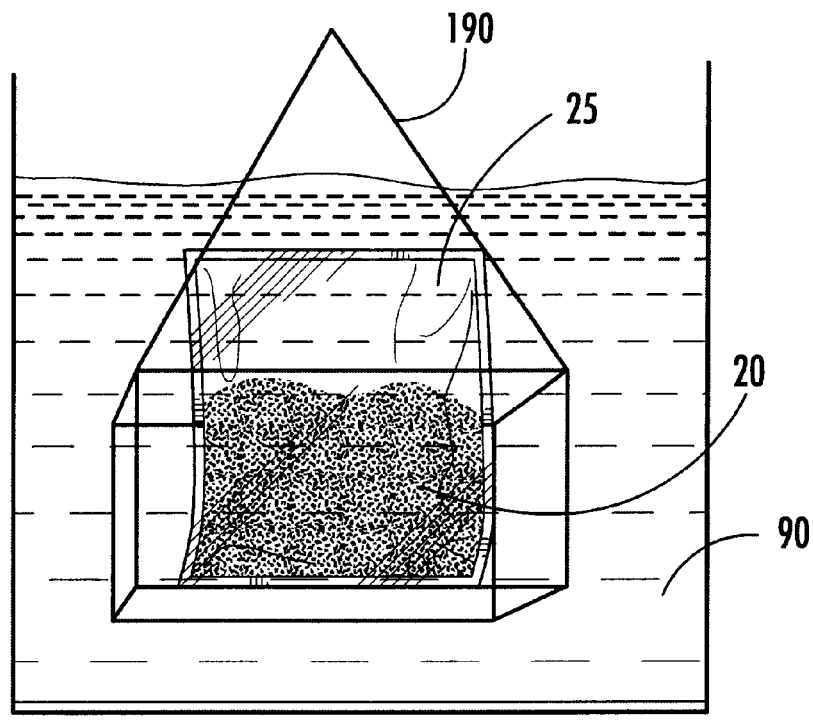
FIG. 23B is a front view of the sealed sample of FIG. 23A which is lowered into a water reservoir according to the present invention.
Figure 23C:
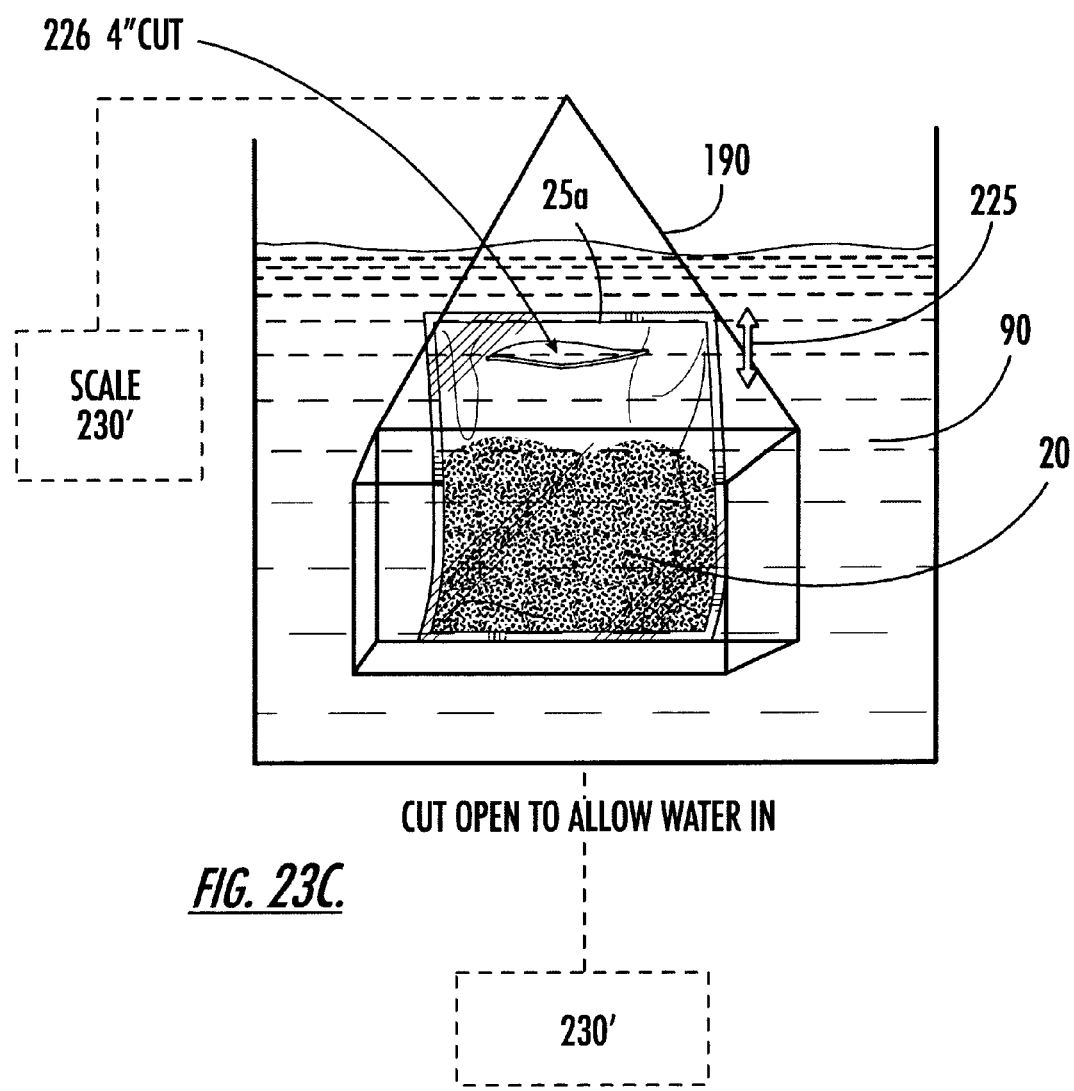
FIG. 23C is a front view of an incision or cut made into the sealed bag of FIG. 23A after it is immersed in the water reservoir shown in FIG. 23B according to the present invention.

Turning now to FIGS. 23A–23C, an additional embodiment of the present invention is illustrated. This embodiment includes water displacement analysis methods which can be used as an alternative to the Rice Gravity Test methodology discussed above. Conventionally, depending on the service time on the pump, the equipment set-up, and/or the vibration technique used during the Rice Test, the results of the Rice Test can vary from lab to lab. In contrast, the test methods and systems proposed by the present invention, as an alternative to the Rice Test, can reduce this variability from lab to lab and can provide consistency across labs. In addition, vibration and agitation are not required during the vacuum process. As shown in FIG. 23A, the material specimen 20 is a material sample which includes one or more, or a mixture of uncompacted or loose aggregates, uncompacted or loose bituminous materials, and uncompacted or loose soil materials. The material sample can also be virgin aggregates (not having been exposed to liquid asphalt). In a preferred embodiment, the material sample is a bituminous paving mixture. As will be appreciated by those of skill in the art, the bituminous paving mixtures typically comprise a blend of aggregates (sizes and types) and a certain amount of tar or asphalt or other like ingredient(s) which are mixed together. When obtaining an appropriately sized sample, the sample may contain loose individual aggregates as well as clumps of the mixed bituminous paving mixture. Thus, during or after obtaining a desired quantity of the material sample 20, the sample may need to be separated or broken down to spread out or "de-clump" the mixture, particularly to break-up the larger-sized clumps. This can be done in a number of ways, but is preferably done by hand by gently throwing or dropping the mixture (or a desired portion of the mixture) against a surface (i.e., onto a table top), or by kneading, rubbing, chopping, or otherwise manipulating the sample. Warming the paving mixture in a flat pan in an oven can facilitate the separation, but, again, care should be taken to reduce reheating effects for the subsequent drying operation (combining the efforts into substantially a single concurrent operation). See e.g. ASTM D2041, p. 179.

In any event, the material sample 20 is heated and a dry sample weight is obtained by conventional procedures. Generally stated, the conventional procedures call for oven-drying the paving mixture in the loose condition. The dry sample weight is recorded or input into a computer, either by a user, or automatically if the scale is set up to input the measured value of the weight directly into a computer operably associated therewith. The sample is then allowed to cool. Preferably, the sample is allowed to cool to approximately 110° F. (or less) before it is then disposed in a sealable bag 25 such as shown in FIG. 23A.

It is also preferred that a sufficient quantity of material sample be used to provide a representative sample for the analysis. Preferably, the sample quantity is from about 500–2500 grams, depending on the particular state, federal, or national specification.

After cooling, the sample 20 is then generally spread within the sealable bag 25. The bag 25 can be any number of sizes. For example, for a sample size which is between about 1000–1500 grams, a 10 inch by 14 inch bag can be used, while a 14 inch by 14 inch bag can be used for samples of about 1500–2500 grams. Suitable bags identified as CoreLok™ bags can be obtained from InstroTek, Inc., of Raleigh, N.C.

The material sample 20 undergoing analysis is preferably at least somewhat evenly distributed within the bag 25 while leaving an empty space 225 (a space without sample materials) adjacent one edge portion of the bag. This space 225 should be where an opening 226 (FIG. 23C) or cut is introduced or inserted into the bag 25 later in the process as will be discussed further below. Preferably, the sample 20 is substantially evenly distributed about a major portion of the bag 25 leaving the portion adjacent the sealed edge 25a empty. Preferably, the material sample is positioned in the bag 25 such that the empty space 225 includes at least the upper two inches of the bag-end adjacent the sealing edge 25a. The two inches can allow the bag seal to extend inwardly about 1 inch from the outer perimeter edge and still leave an open free space of at least about one inch from the sample. Of course, a larger free space can also be used depending on the bag 25 size and the material quantity. The distribution can facilitate the removal of air from the bag and aggregates and/or (preferably bituminous) materials (as well as from their pores) during the evacuation process.

As discussed above for other material specimens 20, the loose material sample 20 in the bag 25 is positioned, as shown in FIG. 1A, in the vacuum chamber 13 of the vacuum apparatus 12. The bag open edge is aligned with the sealing means 35 so that the bag 25 can be sealed at the appropriate time in the cycle. A suitable vacuum setting, rate, and time are selected to evacuate the bag and reintroduce air into the chamber 13. That is, the air is reintroduced after the bag is evacuated and sealed with the material sample held encased therein to collapse the bag against the sample. For example, a pressure of about 28–30 in Hg, and preferably about 29 in Hg, can be used for a typical sample. The vacuum is activated for about 45 seconds to about 1 minute. The vacuum pump/chamber operates to remove the air from the bag and the sample. An exhaust time of about 1.5 minutes is used to control the re-entry of air into the chamber 13 to bring the pressure gradually back to atmospheric condition and collapse the sealed bag 25 against the material sample 20. In this configuration, the bag conforms around the rough or coarse surfaces of the sample. However, due to variable contour of the sample components or constituents, there will be briding of the plastic bag where voids are created between the sample and the bag. These voids are under vacuum, and thus, contain virtually no air. The sealed material sample 20 in the bag 25 is weighed. The weight is recorded, similar to the dry sample weight noted above.

Next, as shown in FIG. 23B, the sealed sample in the bag 25 is immersed in the water bath 90 to a depth sufficient to assure that the entire bag 20 and its contents are submerged. As with conventional water displacement tests, the temperature of the water bath is at a known temperature. Mass determinations in the water bath at temperatures above or below a standard temperature may need to be adjusted or corrected to reflect the actual bath temperature used (a standard bath temperature for calculations is typically 25° C.+/−1°).

Preferably, as shown in FIG. 23B, a holder 190 is used to position the sealed sample in the water bath 90. Typically, the holder 190 is already positioned within the water bath 90. Of course, the holder 190 may be suspended with the sealed bag sample. The suspended holder 190 is preferably operably associated with a scale 230' as schematically shown in FIG. 23C. As shown, the scale 230' can be configured to weigh the sample in the bath either as it is suspended from above, or by other water bath/scale configurations which can be used to measure the sample volume in the water bath.

In one exemplary alternative configuration, a known volume of water can be weighed in a calibrated container on top of the scale 230. Once the weight of the water in the container is measured, the water container can be emptied and the sample placed in the container. Next, the container with the sample is filled typically to a set and calibrated level (above the sample). Measuring the weight will allow the measurement of the sample volume. It is also possible to introduce a quantity of water in a graduated and calibrated container to measure the water level change in the container after placement of the sample in the container.

The holder 190 is configured with a skeletal or mesh body (to allow water to substantially freely enter therein) and to be devoid of sharp edges and materials, particularly on bag contacting surfaces. As necessary, depending on the configuration of the scale 230', the holder 190, and the water bath 90, the weight of the holder 190 can be included as an offset in mass measurements taken with the bag held therein.

Next, as shown in FIG. 23C, after the bag is immersed, an opening 226 is inserted into the empty space 225 portion of the bag 25. Preferably a sharp implement such as scalpel or knife, razor blade, scissors, or the like, is used to slice open or puncture the bag under the seal joint 25a to allow water to enter the bag 25. Care should be taken when inserting the opening to not dislodge or disturb the sample in the bag and to not position the opening 226 too close to the sample to reduce the likelihood that any components of the sample will travel out therefrom. The opening 226 is preferably sized at about 2–6 inches long, and more preferably at about 4 inches long. The opening 226 is preferably positioned about 1–4 inches below the sealing edge 25a of the bag and at least about 1–4 inches above the material sample. The size of the opening 226 will affect the time it takes for water to enter and fill the bag in a manner whereby substantially all of the void spaces are filled. Typically, for a 4 inch opening 226 the bag 25 will be filled and the water displacement measurement obtained within about 5–9 minutes. Of course, although not preferred, a plurality of smaller openings can be employed. Given that the sample is under vacuum in the bag, the insertion of the opening will cause the water to rush into all available voids in the sample and the bag. After the scales stabilize, the volume of water displaced is due to the solid material in the bag. This, in turn, allows for the calculation of the material maximum density, after the appropriate correction for the bag density.

In operation, the water enters and fills the bag 25 and all void spaces in the bag 25 and in the material sample. The maximum volume of the sample displaces water from the water bath 90. The movement of the water into the bag 25 may cause the associated scale 230' to fluctuate in its reading. Accordingly, once the scale 230' is stabilized, the weight of the sample in water can be obtained and recorded as noted above (the density calculations can adjust for the weight of the bag). When placed in water and the sealed bag opened, surface tension on the aggregates coated with asphalt can act to protect the water from penetrating into the aggregates in the short testing time needed to reach stability on the scales. The sample density is determined based on a mathematical relationship including (a) the dry weight of the sample, alone, in air (b) the weight of the sample sealed in the bag, in air, and (c) the weight of the bag (opened) with the sample immersed in water (after the scales have stabilized as noted above). The apparent density of the bag can be offset from the calculated density of the material sample. The apparent bag density can be determined at a production site remote from the laboratory testing facility. The bag density is preferably determined for each production or shipment lot (for each different size bag) as the bags are preferably precision produced to reduce variability of same. Of course, the bags can be individually measured as well. The test provides a repeatable maximum specific gravity measurement.

After the opening is formed in the bag 25, an operator may, if desirable, with the bag still immersed, insert his or hand or a device into the water bath 90 and gently squeeze, agitate, shake and/or vibrate the bag 25 to facilitate the release of any potential bubbles due to outgassing of the bag 25 and/or to release bubbles that may be trapped between sample particles in the sample 20.

Alternatively, the sealed sample 20 can be independently dropped into the water bath 90 without the assistance of a holder 190. An operator can insert the opening 226 in the bag while the bag is submerged in the bath. The water bath 90 can be configured with or operably associated with an automatic gentle agitation means which can be preset to rotate or translate at desired frequencies and/or speeds and times. As before, the water weight measurement can then be obtained once the associated scales have stabilized. For each weight in water, as with conventional procedures, the liquid bath temperature is maintained at a known temperature so that calculations based on the measurements associated with same can be corrected for temperatures beyond the standardized parameters (typically 25° C.+/−1°).

During the handling of the sample or the bag, such as when spreading the coarse mixture in the bag, (typically small) holes can be created in the bag before it is immersed in the water. Unfortunately, these holes can allow air to enter into the bag, and when immersed or placed in the liquid tank, and before cutting the bag, the weight on the scales will continue to change, with a generally slow upward movement of weight indicated on the scales (responsive to water entering the bag). Thus, if water enters a bag because its integrity has been compromised, the scales will not stabilize until after the (immersed) bag is filled with water or liquid. Inadvertent holes in the bag can introduce errors into the test measurements (and can even defeat the purpose of evacuating the sample from air and sealing it in the bag). Generally, if a hole exists in the bag, it will prevent the scales from stabilizing within the first two to three minutes or so after immersion. The instant invention recognizes this operational transient condition and uses it to alert the operator of a potential problem.

Accordingly, in a preferred embodiment, the sealed bag with the sample therein is submerged completely in the liquid displacement bath and the scales are allowed to stabilize before the bag is cut open and while the bag is held immersed or submerged in the liquid. If holes have been inadvertently introduced prior to this step (sometimes occurring because the specimens are coarse and can puncture the bag during handling as noted above), the scales will tend not to stabilize during the first few minutes as water is seeping into the bag until the bag if filled and itself stabilized. If the scales stabilize during the first two to three minutes or so, this affirms that the integrity of the bag is maintained and the procedure can continue. If, on the other hand, the scales fail to stabilize after a predetermined time (typically after more than two to four minutes) after the bag is positioned (submerged) in the tank, a leak in the bag is indicated. The non-stabilized scales can alert the operator to abort the test and reinitiate the test with a new sealed bag (taking care to assure that the specimen is dried), or risk compromised data.

This non-stabilized detection can be based on an operator visual or on a computer monitored feedback system that provides a control feature to block continued testing without operator override when the weight on the scales continue to fluctuate beyond established norms and/or beyond a predetermined time after the bag is submerged and before the desired opening is introduced into the bag. As such, the results can be printed out and included with the test analysis to affirm the bag integrity was not compromised before the intended opening was introduced by the operator during the test procedure.

The water displacement test of the instant invention then calls for the calculation of the maximum specific gravity of the material or mixture using the values established for the dry weight, the dry sealed weight, and the immersed weight in the open bag. The method can be used as an alternative to the Rice Gravity Test and takes approximately 5–9 minutes to complete (excluding the separation, oven drying, and dry weight steps, and depending, inter alia, on the size of the opening, the size of the sample, and the size of the bag).

Figure 25A:
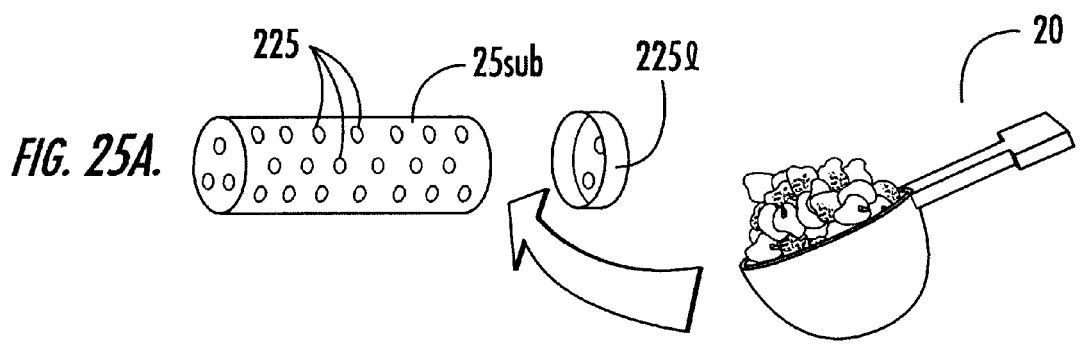
FIG. 25A is a side view of a sub-container used to hold loose, uncompacted material samples which is then encaseable in a sealant according to the present invention.
Figure 25B:
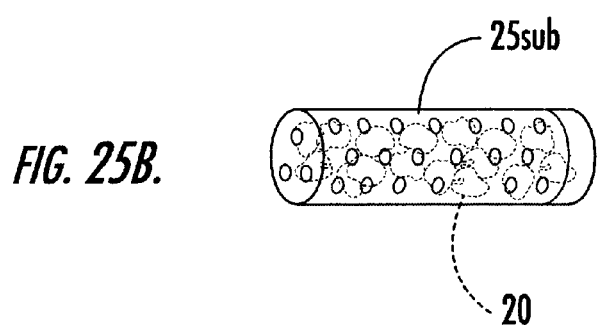
FIG. 25B is a side view of the sub-container of FIG. 25A illustrating the sub-container holding a loose material specimen undergoing analysis.
Figure 25C:
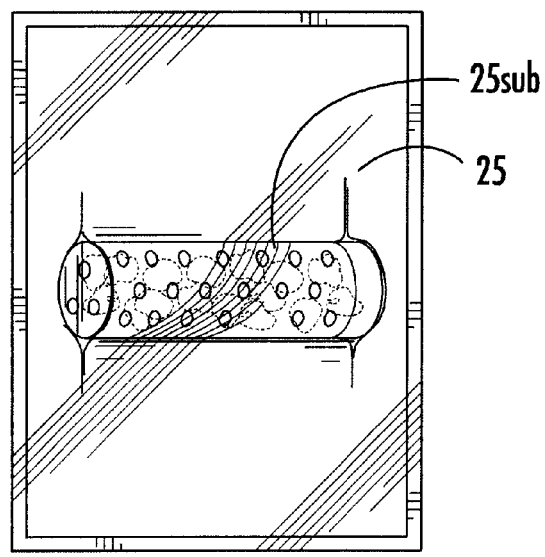
FIG. 25C is a top view of the sub-container with the loose material specimen of FIG. 25B encased in a sealant (shown as a sealed bag) according to the present invention.

In another embodiment, as shown in FIGS. 25A–25C, a sub-container $25_{sub}$ is configured to hold the loose or uncompacted sample or specimen 20 therein. As shown, the sub-container $25_{sub}$ is configured with a plurality of apertures 225 which, in operation, allow liquid to enter therein when the sealed bag is opened and held immersed in the liquid displacement tank as discussed above. That is, as shown in FIG. 25C, the bag 25 encases the sub-container $25_{sub}$ which holds the loose specimen mixture 20 therein. Preferably, the apertures 225 are sized to allow liquid to enter therein when immersed as discussed above and to inhibit the loose mixture from migrating out of the sub-container. The apertures 225 can be positioned on a single surface or portion of a surface or on all surfaces (top, bottom and sides), the number (and size) of apertures will influence the time it takes for the water to fill the bag during testing. The sub-container $25_{sub}$ can, as shown in FIG. 25A, include a removable lid 225l which allows for easy filling and closure of the subcontainer $25_{sub}$ during analysis. Of course, other means of entry such as, but not limited to, a pivotable door, sliding window, or the like can also be used to fill the sub-container $25_{sub}$.

In operation, after the loose or uncompacted specimen or sample is positioned in the sub-container $25_{sub}$, a sealant is positioned over the sub-container $25_{sub}$. Preferably, as shown in FIG. 25C, the sub-container $25_{sub}$ is inserted into the bag 25. The bag 25 holding the sub-container $25_{sub}$ which holds the material specimen 20 is vacuum-sealed as discussed above. The bag walls then collapse against and encase the loose specimen and the sub-container $25_{sub}$ therein. As the bag or sealant collapses against the sub-container $25_{sub}$, it is preferred that the sub-container $25_{sub}$ be configured with a smooth contour. Although shown as generally cylindrical in shape in FIG. 25A, the sub-container $25_{sub}$ can have any number of suitable configurations such as, but not limited to rectangular, square, disc, donut, spherical, elliptical, and the like (see, e.g. FIGS. 25D–25F). It is preferred that sharp edges be avoided or its edges radiused to inhibit punctures during vacuum sealing operations or handling. In addition, the sub-container $25_{sub}$ is preferably structurally self-supporting (able to maintain its shape during evacuation as the bag or sealant covers same) and can be formed from any number of suitable materials, preferably from non-absorbent materials such as composites, polyvinylchloride ("PVC"), metals, and the like. The sub-container $25_{sub}$ can be formed with solid container walls with one or more openings formed therethrough, or as a mesh-like body, the mesh chosen to limit or prevent the migration of the loose or uncompacted sample therethrough. As shown, the material specimen 20 is sized so as to substantially fill the sub-container $25_{sub}$. In operation, material specimens 20 sized to substantially fill the sub-container $25_{sub}$ can facilitate the immersion of the sealed sample in the liquid displacement bath and reduce the likelihood that the vacuum-sealed specimen will float to the top of the liquid bath. Alternatively, or in addition to this relative correspondence in sizing, weights or mass can be added to the bottom of the sub-container $25_{sub}$ (or integrated into same) to counter the buoyant force and help submerge the sealed specimen.

Figure 25D:
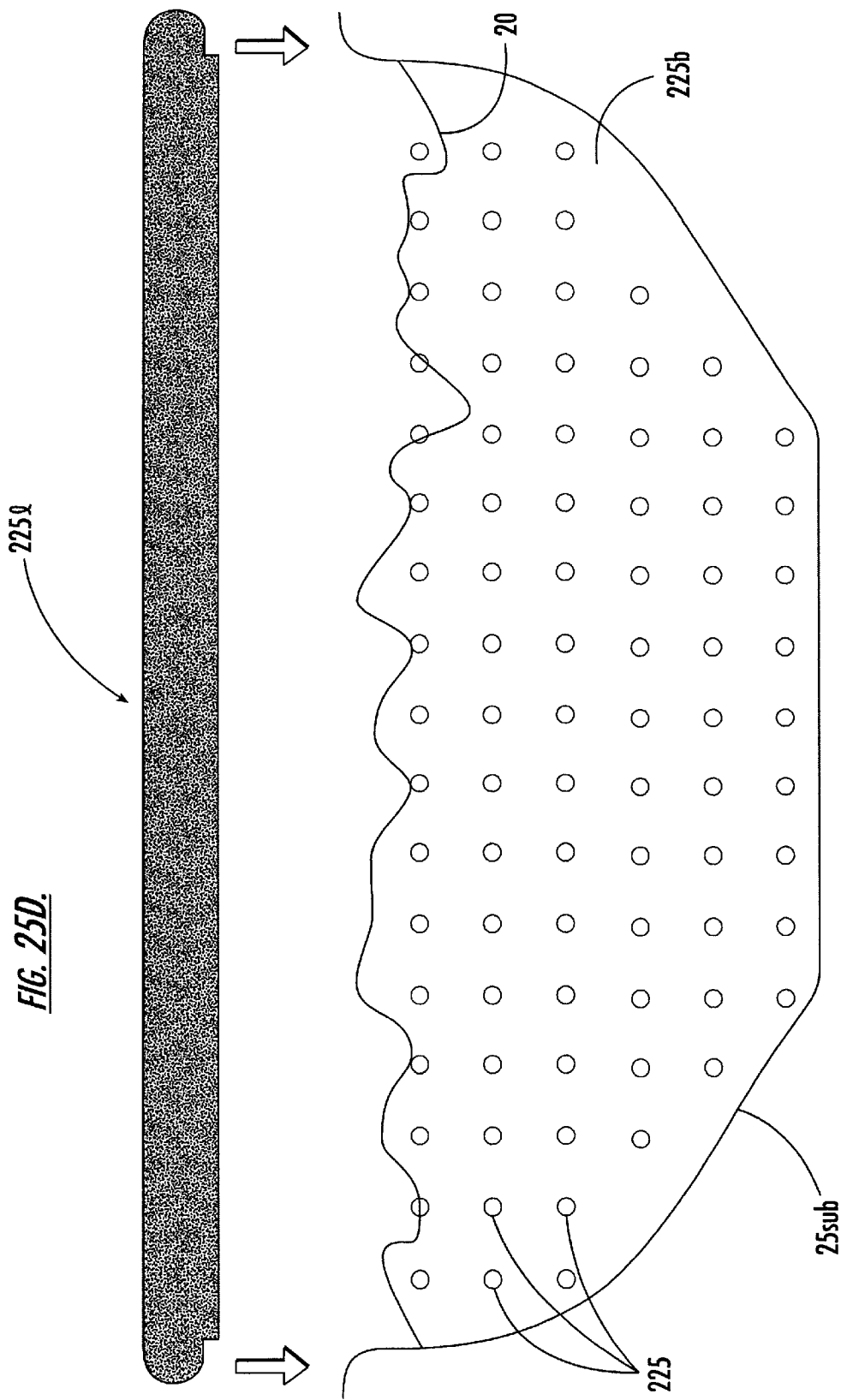
FIG. 25D is a side view of an alternative embodiment of a sub-container holding a material sample.
Figure 25E:
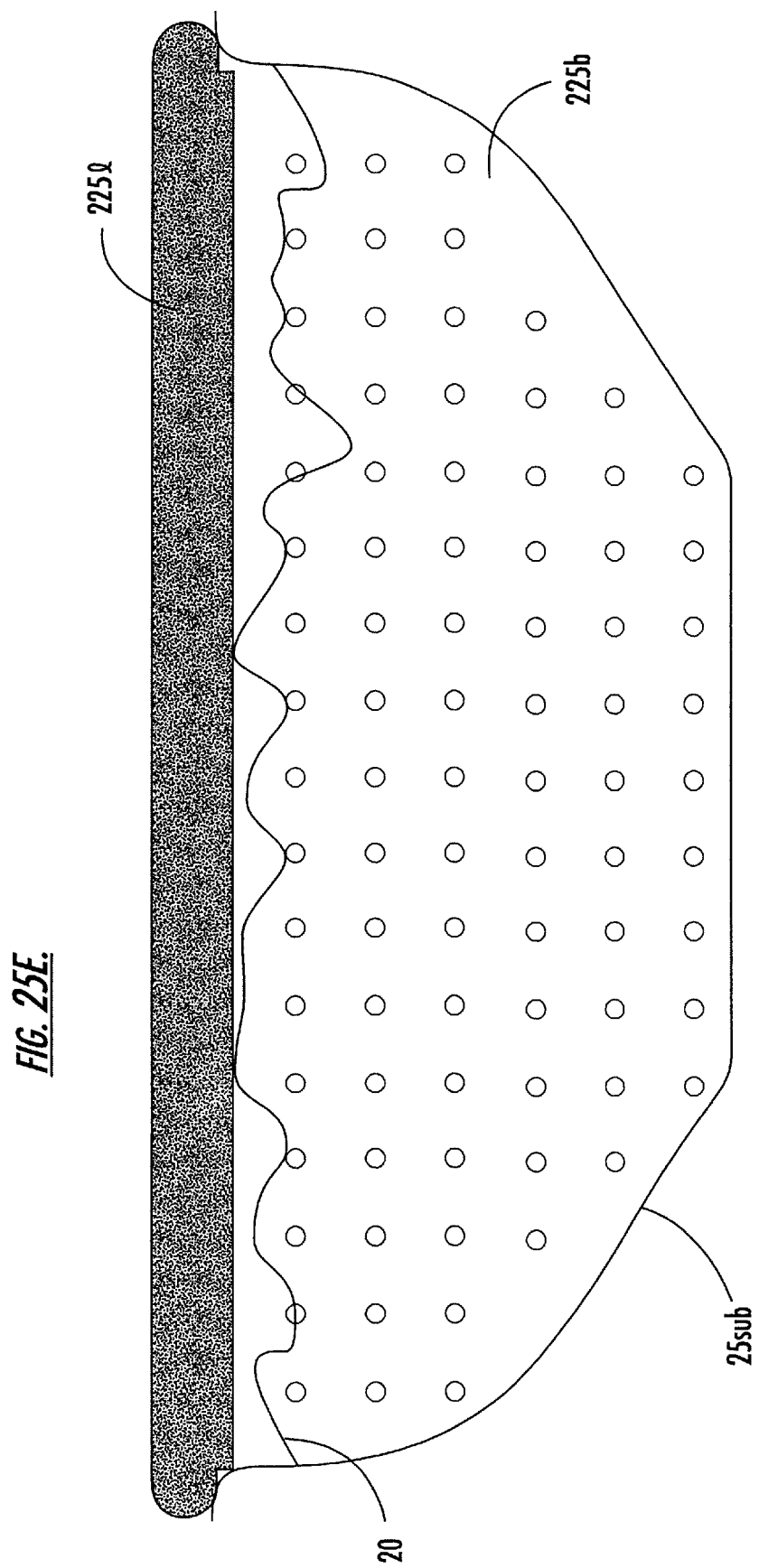
FIG. 25E is a side view of the embodiment shown in FIG. 25D with the lid in position on the sub-container.
Figure 25F:
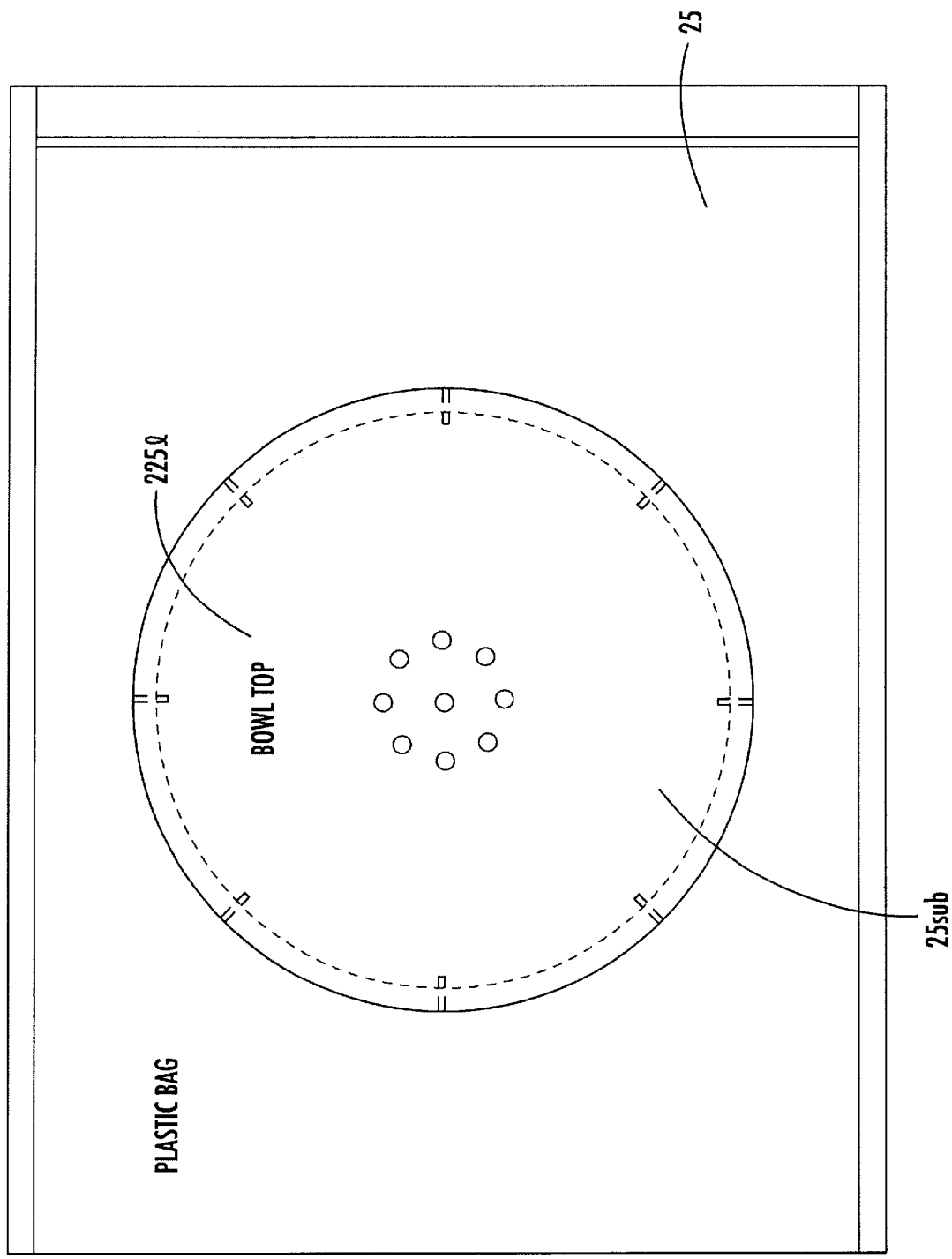
FIG. 25F is a top view of the embodiment shown in FIG. 25E with the sub-container encased in a sealant.

FIGS. 25D–25F illustrate another embodiment of a sub-container $25_{sub}$. As shown, the sub-container $25_{sub}$ is configured as a bowl 225b with a lid 225l configured to overlay the top to enclose the body of the bowl 225b. As shown in FIG. 25D, the sample 20 is preferably sized to substantially fill the bowl 225b. Although the sample is not required to be selected so as to substantially fill the bowl 225b, in operation, as discussed above, material samples or specimens 20 sized in this manner can facilitate the sealed or encased sample immersion in the liquid bath.

As shown in FIG. 25D, the lid 225l of the sub-container $25_{sub}$ is sized to snugly abut the top of the sub-container $25_{sub}$ and preferably to securely attach to the top portion of the bowl 225b via suitable attaching means. Examples of suitable attaching means include but are not limited to, adhesives, threaded configurations, frictional engagement type configurations and the like. Preferably, the assembled profile or contour of the sub-container $25_{sub}$ is such that it will inhibit the likelihood that the sealant will be punctured during evacuation or handling (i.e., a smooth contour with radiused or rounded edges).

One example of a configuration used for liquid displacement evaluation is a three-quart stainless steel bowl 225b with a nylon lid 225l which is sized to hold the loose sample 20 to a level as generally shown in FIG. 25D. The bowl 225b and the lid 225l contain plurality of openings 225 to allow for penetration of water into the bowl and to aid in the escape of remaining residual air out of the bowl. The sub-container $25_{sub}$ weight and size is configured to contain a sufficient sample 20 weight for complete submersion of the sealed sub-container into the water tank during liquid displacement analysis. As noted above, care should be taken to reduce the amount of free space within the bowl to reduce the chance that the sub-container $25_{sub}$ and the sample 20 will float during the water displacement density analysis. If floating occurs, the sub-container $25_{sub}$ is preferably physically held under water before and after cutting the bag 25 to allow the water weight to fully submerge the sub-container with the sample held therein. The sample can be analyzed after the sub-container $25_{sub}$ containing the sample 20 is fully immersed.

Preferably, to facilitate a slow seepage of water into the sub-container $25_{sub}$ after the opening is introduced into the sealant or bag 25, one can cut the bag 25 and not force the cut open (the cut edges remain proximate the other). This can allow the water to enter the sub-container $25_{sub}$ in a relatively slow manner to allow any residual air voids to be pushed out. If water rushes in fast from all sides, air may be potentially trapped in the sub-container $25_{sub}$. This slow or seeping water entry may be important when agitation is not used.

As discussed above, the density of the sub-container $25_{sub}$ is calculated so that its contribution to the density of the combined bag, reference sample, and sub-container $25_{sub}$ can be offset therefrom.

FIG. 24 illustrates a typical data collection sheet with sample data which can be employed to establish the sample density (typically referred to as "sample core density") according to the present invention. Of course, in lieu of a data sheet, the numbers can be input into a computer for automatic calculation from a computer program. In addition, one or more scales can be operably associated with the computer to relay the measured values directly thereto. In any event, as shown, a sample is obtained and an identification number established (shown as sample A). After the sample is separated, as necessary, and oven dried. The dry weight of the sample is obtained in air (identified as parameter "A"). The sample is then sealed in the bag 25 and the weight of the sealed sample in the bag is measured (identified as parameter "B"). The sealed sample in the bag is then immersed in the water bath and the bag cut to allow water to enter therein while the bag is held under water. The sample weight in the opened bag in the water is obtained (identified as parameter "C"). A value identified as parameter "D" is calculated by taking the difference between the weight in air and the weight in water (B–C) divided by 0.997 (the density of water at 25 C.). A value identified as parameter "E" is next calculated by taking the difference between the sealed air weight and the weight of the sample in air (B–A) divided by the apparent bag density (shown here as calculated with the given small bag number). The apparent bag density values are preferably provided for each production and/or shipment lot for each size bag as noted on the bottom of the data sheet. A corrected parameter F is calculated by taking the difference between the values established for parameters D and E (D–E). Next parameter "G" the core density is determined based on the core weight in air and the corrected weight of the sample established by the relationship "A/F". The maximum theoretical specific gravity can be established from this value according to conventional calculations.

In addition, the methods of the instant invention can be used for establishing the percent compaction of bituminous samples. For example, obtaining the uncompacted bituminous paving mixture material sample and determining the theoretical maximum specific gravity and density as described above can provide a baseline value. For discussion purposes, a typical maximum specific gravity can be stated to be about 150 lb/ft$^3$. A second liquid displacement analysis can be subsequently performed from a compacted sample of the bituminous material, preferably as compacted at a field site. This second liquid displacement analysis can be performed with a Corelok™ bag and vacuum system according to the bulk specific gravity test methods for compacted materials described above. For discussion purposes, a typical compaction value can be stated to be about 145 lb/ft$^3$. The ratio of the compacted bulk specific gravity measurement to the theoretical maximum specific gravity and density measurement can provide the % compaction. For the example numbers stated here, the compaction percent is (145/150)×100 or 96.67%.

In addition, the present invention recognizes that there is a correlation between air void content of the uncompacted mixture and the permeability of asphalt and uses this correlation to obtain an asphalt permeability measurement. "Permeability" can be described as the rate of liquid infiltration through the material sample. Similar to the maximum specific density test method described above, the permeability measurement can be based upon the difference of or a comparison of the submerged weight of the dry sample submerged in the sealed bag in the water tank and the immersed sealed sample after it is opened to allow the water into all available voids within the sample. The difference between the two derived density measurements is a representative measure of sample void volume which can be correlated to permeability of compacted material.

In summary, the instant invention allows for a reliable method to seal a porous uncompacted or compacted material specimen which can provide accurate measurement results for density measurements using water or liquid displacement tests. Advantageously, the apparatus, system and methods of the instant invention can reduce the variation attributed to operators by making the method essentially independent of operator material trimming and custom application. The sealing method is consistent across specimens and similar bags are configured to displace the same volume of water. Further, the sealed sample is easily removed from the seal and the specimen can undergo further evaluation because it's material properties remain intact. Still further, the instant invention can be used across a plurality of specimen composite mixes without requiring standard reference block density correction factors at the laboratory for each compacted specimen evaluated.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining an apparent density of a sealant used to encase a material specimen during liquid displacement evaluations, comprising the steps of:

providing a plurality of material reference samples in an assortment of dimensional ranges and geometrical shapes;

obtaining a sealant used to encase material specimens undergoing liquid displacement evaluations; and establishing a plurality of apparent density values for the sealant, one apparent density value for each of the plurality of reference samples identified in said providing step.

2. A method according to claim 1, further comprising the steps of:

preparing a bituminous material specimen having a shape and size for density evaluation including encasing the specimen in a sealant;

selecting an apparent density value from the apparent density values defined by said establishing steps, wherein the selected apparent density value corresponds to the selected reference sample; and calculating the material density of the material specimen using the apparent density value identified in said selecting step.

3. A method according to claim 1, wherein the plurality of material specimens comprises material specimens having air voids formed on at least one outer surface thereof.

4. A method according to claim 1, wherein the plurality of material specimens comprises at least one material specimen comprising a plurality of loose non-absorbent articles.

5. A material reference sample used for determaining the apparent density of a sealant used to encase a bituminous material specimen during liquid displacement evaluations, the material reference comprising:

a cylinder with an outer perimeter including an outer wall and opposing top and bottom surface; and a plurality of air voids positioned on a portion of said outer perimeter, wherein said cylinder is a solid core cylinder, and wherein said plurality of air voids are positioned on said top surface, and wherein said plurality of air voids are configured and sized to represent about 0.5–3.2% air void content in said sample.

6. A material reference sample according to claim 5, wherein said cylinder is formed of compacted asphalt having a size and shape and an air void content.

7. A method for determining the apparent density of a sealant used to encase a bituminous material specimen during liquid displacement evaluations;

providing at least one material reference cylinder with an outer perimeter including an outer wall and opposing top and bottom surfaces with a plurality of air voids positioned on a portion of said outer perimeter;

placing the material reference in a sealant bag having an unknowm apparent density; immersing the material reference in the sealant bag in a liquid displacement bath; and calculating the apparent density of the sealant bag.

8. A method for determining the apparent density of a sealant used to encase a loose or uncompacted paving mixture material specimen during liquid displacement evaluations, comprising:

providing a material reference comprising a plurality of loose non-absorbent articles;

placing the loose articles in a sealant bag having an unknown apparent density;

immersing the loose articles in the sealant bag in a liquid displacement bath; and calculating the apparent density of the sealant bag.

9. A method according to claim 8, wherein said plurality of loose non-absorbent articles is a plurality of spherical solid material balls.

* * * * *

UNITED STATES PATENT AND TRADEMARK OFFICE
CERTIFICATE OF CORRECTION

PATENT NO. : 6,817,243 B2
DATED : November 16, 2004
INVENTOR(S) : Regimand et al.

It is certified that error appears in the above-identified patent and that said Letters Patent is hereby corrected as shown below:

Title page,
Item [60], Related U.S. Application Data, should read -- Second division of application No. 09/580,792, filed on May 30, 2000, now Pat. No. 6,668,647 which is a continuation-in-part of application No. 09/340,105, filed on Jun. 25, 1999, now Pat. No. 6,321,589. Application No. 10/196,650, filed on Jul. 16, 2002, now Pat. No. 6,629,459 is the first divison of Pat. No. 6,668,647. --

Signed and Sealed this

Fifteenth Day of March, 2005

JON W. DUDAS
*Director of the United States Patent and Trademark Office*